United States Patent
Sawada et al.

(10) Patent No.: US 11,419,512 B2
(45) Date of Patent: Aug. 23, 2022

(54) FLOW VOLUME MEASURING DEVICE, FLOW VOLUME MEASURING METHOD, PRESSURE MEASURING DEVICE, AND PRESSURE MEASURING METHOD

(71) Applicant: KYUSHU UNIVERSITY, NATIONAL UNIVERSITY CORPORATION, Fukuoka (JP)

(72) Inventors: Renshi Sawada, Fukuoka (JP); Hirofumi Nogami, Fukuoka (JP); Tomohito Sekiguchi, Fukuoka (JP); Yuma Hayashida, Fukuoka (JP); Ryo Inoue, Fukuoka (JP); Ryuta Shiraishi, Fukuoka (JP)

(73) Assignee: KYUSHU UNIVERSITY, NATIONAL UNIVERSITY CORPORATION

( * ) Notice: Subject to any disclaimer, the term of this patent is extended or adjusted under 35 U.S.C. 154(b) by 907 days.

(21) Appl. No.: 16/305,658

(22) PCT Filed: Apr. 13, 2017

(86) PCT No.: PCT/JP2017/015203
§ 371 (c)(1),
(2) Date: Nov. 29, 2018

(87) PCT Pub. No.: WO2017/208645
PCT Pub. Date: Dec. 7, 2017

(65) Prior Publication Data
US 2020/0323438 A1    Oct. 15, 2020

(30) Foreign Application Priority Data

May 31, 2016 (JP) .............................. JP2016-109557

(51) Int. Cl.
*A61B 5/026* (2006.01)
*A61B 5/029* (2006.01)
(Continued)

(52) U.S. Cl.
CPC ............ *A61B 5/0261* (2013.01); *A61B 5/029* (2013.01); *A61B 5/0295* (2013.01);
(Continued)

(58) Field of Classification Search
CPC ....... A61B 5/026; A61B 5/6826; A61B 5/029; A61B 5/6843; A61B 5/7278;
(Continued)

(56) References Cited

U.S. PATENT DOCUMENTS 4,566,463 A * 1/1986 Taniguchi .......... A61B 5/02255
600/479
5,778,879 A * 7/1998 Ota ........................ A61B 5/022
600/310
(Continued)

FOREIGN PATENT DOCUMENTS

EP       2837327 A1    2/2015
JP    2005-058766 A    3/2005
(Continued)

OTHER PUBLICATIONS

Japanese Office Action for corresponding Application No. 2018-520702 dated Mar. 23, 2021 with English translation (8 Pages).
(Continued)

*Primary Examiner* — Oommen Jacob
(74) *Attorney, Agent, or Firm* — Harness, Dickey & Pierce, P.L.C.

(57) ABSTRACT

It is possible to improve a measurement accuracy of a liquid flow volume, thereby improving reproducibility of a measured value. Provided is a flow volume measuring device including a light source which emits light to a measuring-
(Continued)

target region; a light receiving element which receives light scattered at the measuring-target region from the light emitted from the light source; a contact member having translucency with respect to a wavelength of the emitted light and a wavelength of the scattered light, the contact member including a surface which faces the measuring-target region and with which the measuring-target region is contactable over the entire surface; and a flow volume measuring unit which measures a flow volume of liquid flowing through the measuring-target region based upon the scattered light.

14 Claims, 35 Drawing Sheets

(51) Int. Cl.
  *A61B 5/0295* (2006.01)
  *A61B 5/00* (2006.01)
  *G01L 1/22* (2006.01)
(52) U.S. Cl.
  CPC .......... *A61B 5/4875* (2013.01); *A61B 5/6843* (2013.01); *A61B 5/7278* (2013.01); *G01L 1/22* (2013.01); *A61B 2562/0238* (2013.01)
(58) Field of Classification Search
  CPC ... A61B 5/0261; A61B 5/0295; A61B 5/6898; A61B 5/4875; A61B 5/6838; A61B 2562/0238; A61B 2562/0261; A61B 2562/0252; A61B 2562/0233; A61B 8/065; G01F 1/00; G01F 1/66; G01L 1/22; G01L 1/04
  See application file for complete search history.

(56) References Cited

U.S. PATENT DOCUMENTS

| | | | | |
|---|---|---|---|---|
| 6,221,025 | B1* | 4/2001 | Skoletsky | A61B 5/026 600/549 |
| 7,407,486 | B2* | 8/2008 | Huiku | A61B 5/4821 600/481 |
| 8,306,593 | B2* | 11/2012 | Hwang | A61B 5/6838 600/335 |
| 8,352,004 | B2* | 1/2013 | Mannheimer | A61B 5/14552 600/310 |
| 9,226,671 | B2* | 1/2016 | Cho | A61B 5/6843 |
| 9,289,177 | B2* | 3/2016 | Kassim | A61B 5/6898 |
| 10,813,561 | B2* | 10/2020 | Kwon | A61B 5/7278 |
| 2002/0158134 | A1* | 10/2002 | Goto | G06K 7/10881 235/462.45 |
| 2003/0109791 | A1* | 6/2003 | Kondo | A61B 5/021 600/500 |
| 2004/0236233 | A1* | 11/2004 | Kosuda | A61B 5/02416 600/485 |
| 2005/0038349 | A1 | 2/2005 | Choi et al. | |
| 2005/0107710 | A1* | 5/2005 | Nakayama | A61B 5/02125 600/500 |
| 2005/0225529 | A1* | 10/2005 | Shinokura | G06F 3/03548 345/156 |
| 2006/0104824 | A1* | 5/2006 | Schnall | A61B 5/02 417/53 |
| 2007/0161914 | A1* | 7/2007 | Zdeblick | A61B 5/02158 600/486 |
| 2007/0167844 | A1* | 7/2007 | Asada | A61B 5/022 600/490 |
| 2008/0067132 | A1* | 3/2008 | Ross | A61M 1/341 210/739 |
| 2008/0097172 | A1 | 4/2008 | Sawada et al. | |
| 2008/0221419 | A1 | 9/2008 | Furman | |
| 2008/0249379 | A1* | 10/2008 | Furman | A61B 5/0031 600/301 |
| 2008/0275321 | A1 | 11/2008 | Furman | |
| 2008/0287800 | A1 | 11/2008 | Furman | |
| 2009/0048518 | A1 | 2/2009 | Furman | |
| 2009/0221882 | A1 | 9/2009 | Furman | |
| 2010/0168585 | A1* | 7/2010 | Fujii | A61B 5/1172 600/476 |
| 2012/0016245 | A1* | 1/2012 | Niwa | A61B 5/02007 600/476 |
| 2012/0059245 | A1* | 3/2012 | Buschmann | A61B 5/02241 600/490 |
| 2012/0190944 | A1* | 7/2012 | Thaveeprungsriporn | A61B 5/1455 600/310 |
| 2013/0137994 | A1 | 5/2013 | Sawada et al. | |
| 2013/0261468 | A1* | 10/2013 | Semler | A61B 5/0261 600/473 |
| 2013/0289366 | A1 | 10/2013 | Chua et al. | |
| 2013/0296665 | A1 | 11/2013 | Kassim et al. | |
| 2013/0296666 | A1 | 11/2013 | Kumar et al. | |
| 2013/0296673 | A1* | 11/2013 | Thaveeprungsriporn | A61B 5/0295 600/323 |
| 2013/0296714 | A1* | 11/2013 | Kassim | G01N 21/3151 600/479 |
| 2015/0051500 | A1* | 2/2015 | Elliott | G01K 13/20 600/480 |
| 2016/0106326 | A1* | 4/2016 | Bajaj | A61B 8/06 600/504 |
| 2017/0020399 | A1* | 1/2017 | Shemesh | A61B 5/0205 |
| 2017/0251935 | A1* | 9/2017 | Yuen | A61B 5/0261 |
| 2017/0319081 | A1 | 11/2017 | Sawada et al. | |
| 2020/0323438 | A1* | 10/2020 | Sawada | A61B 5/0295 |

FOREIGN PATENT DOCUMENTS

| | | |
|---|---|---|
| JP | 2008-054890 A | 3/2008 |
| JP | 4061409 B2 | 3/2008 |
| JP | 2011-526498 A | 10/2011 |
| JP | 2014-507209 A | 3/2014 |
| JP | 2016-077735 A | 5/2016 |
| WO | WO-2013-153664 A1 | 10/2013 |
| WO | WO-2015-199159 A1 | 12/2015 |

OTHER PUBLICATIONS

International Search Report for PCT/JP2017/015203, dated Jun. 20, 2017 (5 pages).
Written Opinion for PCT/JP2017/015203, dated Jun. 20, 2017 (15 pages).
Japanese Office Action for Japanese Application No. 2016-109557, dated Apr. 4, 2017 (6 pages).
Notice of Reasons for Refusal for corresponding Japanese Application No. 2018-520702 dated Dec. 14, 2021, with English translation (3 Pages).

* cited by examiner

FIG.12A
| PARAMETER | SYMBOL | NUMERICAL VALUE | UNIT |
|---|---|---|---|
| TOTAL LOAD | P | 1.00 | [N] |
| LENGTH OF BEAM | l | 29.5 | [mm] |
| CONTACT PORTION LENGTH | a | VARIABLE | [mm] |
| DEPTH OF BEAM | b | 10.0 | [mm] |
| HEIGHT OF BEAM | h | 0.8 | [mm] |
| YOUNG'S MODULUS | E | 3.14 | [Gpa] |
| SECONDARY MOMENT OF CROSS SECTION | I | 0.427 | [mm$^4$] |
FIG.12B
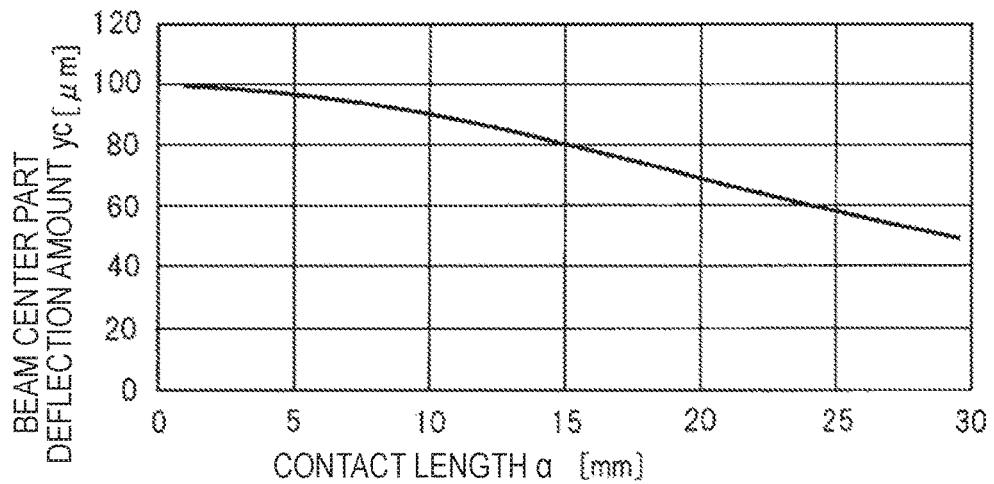
FIG.12C
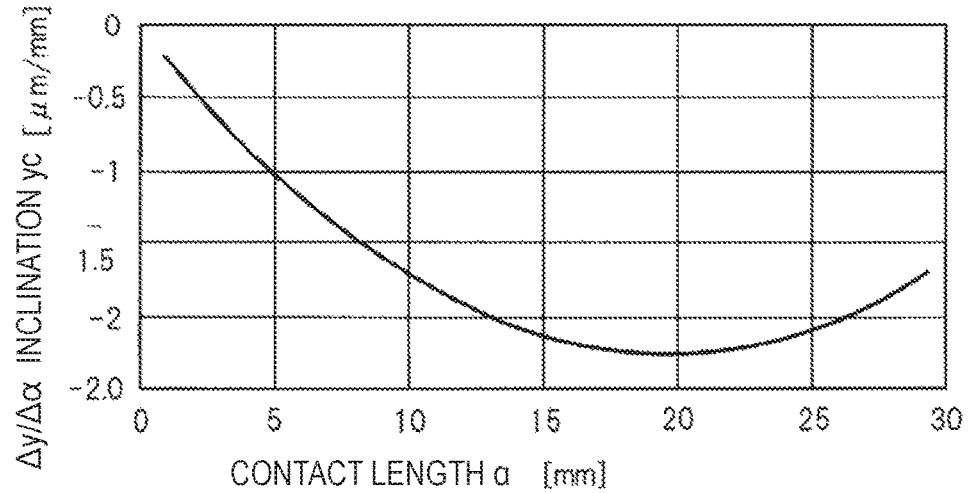

FIG.14

| PARAMETER | SYMBOL | NUMERICAL VALUE | UNIT | CONDITIONS |
|---|---|---|---|---|
| TOTAL LOAD | P | 0.81 | [N] | NONE IN PARTICULAR |
| LENGTH OF BEAM | l | 4 | [mm] | $l \geq \alpha$ |
| CONTACT PORTION LENGTH | $\alpha$ | 3 | [mm] | $\alpha \leq 5 [mm]$ |
| DEPTH OF BEAM | b | 3 | [mm] | NONE IN PARTICULAR |
| HEIGHT OF BEAM | h | 400 | [$\mu$m] | NONE IN PARTICULAR |
| YOUNG'S MODULUS | E | 3.14 | [Gpa] | 2.2~3.14[Gpa] |
| SECONDARY MOMENT OF CROSS SECTION | I | 0.016 | [mm$^4$] | (bh^3)/12 |

FIG.19

| LOAD PATTERN | BEAM CENTER PART | | MAXIMUM DISPLACEMENT PORTION | | |
|---|---|---|---|---|---|
| | DEFLECTION AMOUNT | INCLINATION | DEFLECTION AMOUNT | INCLINATION | COORDINATES [mm] |
| A | 3.484835 | 0 | 3.484835 | 0 | 0 |
| B | 3.484835 | 0.141794 | 5.231335 | −0.03402 | +0.05 |
| C | 3.484835 | 0.404626 | 3.487556 | 0.069634 | +0.1 |

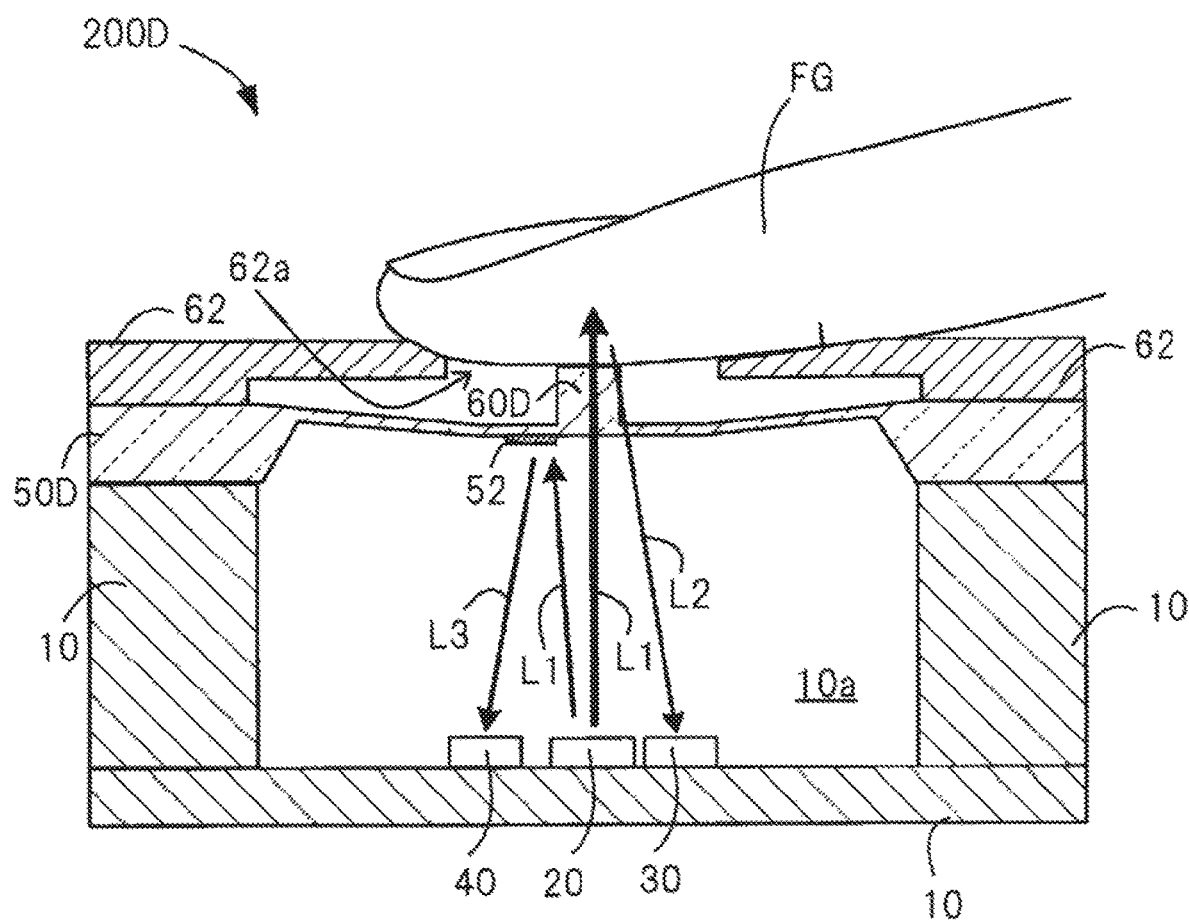

| PARAMETER | SYMBOL | NUMERICAL VALUE | UNIT | CONDITIONS |
|---|---|---|---|---|
| TOTAL LOAD | P | 1 | [N] | NONE IN PARTICULAR |
| DISK DIAMETER | l | 5 | [mm] | $l \geq \alpha$ |
| CONTACT PORTION DIAMETER | $\alpha$ | 3 | [mm] | $\alpha \leq 5$ [mm] |
| THICKNESS OF DISK | h | 400 | [$\mu$m] | NONE IN PARTICULAR |
| YOUNG'S MODULUS | E | 3.14 | [Gpa] | 2.2~3.14[Gpa] |
| POISSON'S RATIO | v | 0.3 | [-] | $-1 < v < 0.5$ |
| POISSON NUMBER | m | 3.33333 | [-] | $1/v$ |
| DEFLECTION STRENGTH | D | 18.40293 | [N·mm] | $(m^2 \times E \times h^3)/12(m^2-1)$ |

FLOW VOLUME MEASURING DEVICE, FLOW VOLUME MEASURING METHOD, PRESSURE MEASURING DEVICE, AND PRESSURE MEASURING METHOD

TECHNICAL FIELD

The present disclosure relates to a flow volume measuring device, a flow volume measuring method, a pressure measuring device, and a pressure measuring method.

RELATED ART

In the related art, there is known a biosensor in which light emitted from a light emitting part is emitted toward an external biological tissue, and scattered light from the biological tissue is received at a light receiving part, thereby measuring a value concerning a liquid substance existing in the biological tissue (refer to Japanese Patent No. 4061409). The biosensor is, for example, a blood flow volume measuring device.

In the blood flow volume measuring device, a measurement value of a blood flow volume is affected by pressure (contact pressure) to be applied to an object measuring unit. In addition, there is known a blood flow volume measuring device which measures a blood flow volume of a measuring-target region when contact pressure against the measuring measuring-target region of a subject is detected, and the contact pressure against the measuring measuring-target region becomes a preset contact pressure (refer to WO 2015/199159 A).

A blood flow volume measuring device in the related art takes into consideration of contact pressure against the blood flow volume measuring device, but does not take into consideration of a contact place and a contact area of the blood flow volume measuring device. Therefore, a measured value of a blood flow volume may fluctuate depending on the contact place and the contact area, thereby resulting in deterioration of measurement accuracy.

The present disclosure has been made in consideration of the above-mentioned circumstances, and provides a flow volume measuring device, a flow volume measuring method, a pressure measuring device, and a pressure measuring method capable of improving a measurement accuracy of a liquid flow volume, thereby improving the reproducibility of a measured value.

SUMMARY OF THE INVENTION

A flow volume measuring device according to the present disclosure includes a light source which emits light to a measuring-target region; a light receiving element which receives light scattered at the measuring-target region from the light emitted from the light source; a contact member having translucency with respect to a wavelength of the emitted light and a wavelength of the scattered light, the contact member including a surface which faces the measuring-target region and with which the measuring-target region is contactable over the entire surface; and a flow volume measuring unit which measures a flow volume of liquid flowing through the measuring-target region based upon the scattered light.

A flow volume measuring device according to the present disclosure includes a light source which emits light to a measuring-target region; a light receiving element which receives light scattered at the measuring-target region from the light emitted from the light source; a translucent member having translucency with respect to a wavelength of the emitted light and a wavelength of the scattered light; a pressure sensor embedded in the translucent member, and including a surface which faces the measuring-target region and with which the measuring-target region is contactable over the entire surface, the pressure sensor detecting contact pressure caused by contact with the measuring-target region; and a flow volume measuring unit which measures a flow volume of liquid flowing through the measuring-target region based upon the scattered light.

A pressure measuring device according to the present disclosure includes a light source which emits light to a measuring-target region; a light receiving element which receives light scattered at the measuring-target region from the light emitted from the light source; a contact member having translucency with respect to a wavelength of the emitted light and a wavelength of the scattered light, and including a surface which faces the measuring-target region and with which the measuring-target region is contactable over the entire surface; a flow volume measuring unit which measures a flow volume of liquid flowing through the measuring-target region based upon the scattered light; and a pressure measuring unit which measures pressure of the liquid flowing through the measuring-target region based upon pulse wave amplitude of the flow volume of the measuring-target region.

A flow volume measuring method according to the present disclosure is a flow volume measuring method in a flow volume measuring device, the method including: emitting light to a measuring-target region; receiving light scattered at the measuring-target region from the emitted light; and measuring a flow volume of liquid flowing through the measuring-target region based upon the scattered light. A contact member may have translucency with respect to a wavelength of the emitted light and a wavelength of the scattered light, and may include a surface which faces the measuring-target region and with which the measuring-target region is contactable over the entire surface.

A pressure measuring method of the present disclosure is a pressure measuring method in a pressure measuring device, the method including: emitting light to a measuring-target region; receiving light scattered at the measuring-target region from the emitted light; measuring a flow volume of liquid flowing through the measuring-target region based upon the scattered light; and measuring pressure of the liquid flowing through the measuring-target region based upon pulse wave amplitude of the flow volume of the measuring-target region. A contact member may have translucency with respect to a wavelength of the emitted light and a wavelength of the scattered light, and may include a surface which faces the measuring-target region and with which the measuring-target region is contactable over the entire surface.

Advantageous Effects of Invention

According to the present disclosure, it is possible to improve the measurement accuracy of a liquid flow volume, thereby improving the reproducibility of a measured value.

BRIEF DESCRIPTION OF THE DRAWINGS

FIG. 12A is a schematic diagram illustrating one example of a parameter used for a first simulation, FIG. 12B is a graph illustrating one example of a relationship between a deflection amount at a beam center part and a contact length, and FIG. 12C is a graph illustrating one example of an influence of a change (an inclination) of the contact length.

FIG. 14 is a schematic diagram illustrating one example of a first parameter used for a second simulation.

FIG. 19 is a schematic diagram illustrating a deflection amount and an inclination of a doubly supported beam at a beam center part and a maximum displacement portion in each load pattern.

FIG. 26 is a cross-sectional view illustrating a configuration example of a blood flow volume sensor according to a fifth embodiment.

DETAILED DESCRIPTION OF THE PREFERRED EMBODIMENTS

Hereinafter, embodiments of the present disclosure will be described with reference to the drawings.

First Embodiment

Figure 1A:
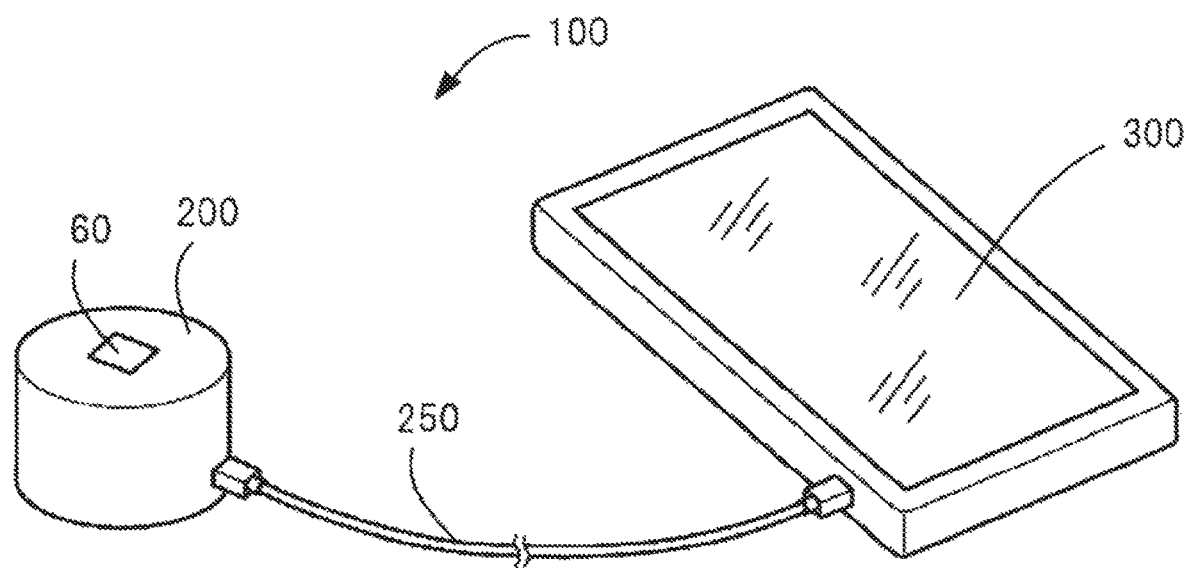
FIGS. 1A and 1B are schematic diagrams illustrating a first configuration example of a blood flow volume measuring device including a blood flow volume sensor and electronic equipment.
Figure 1B:
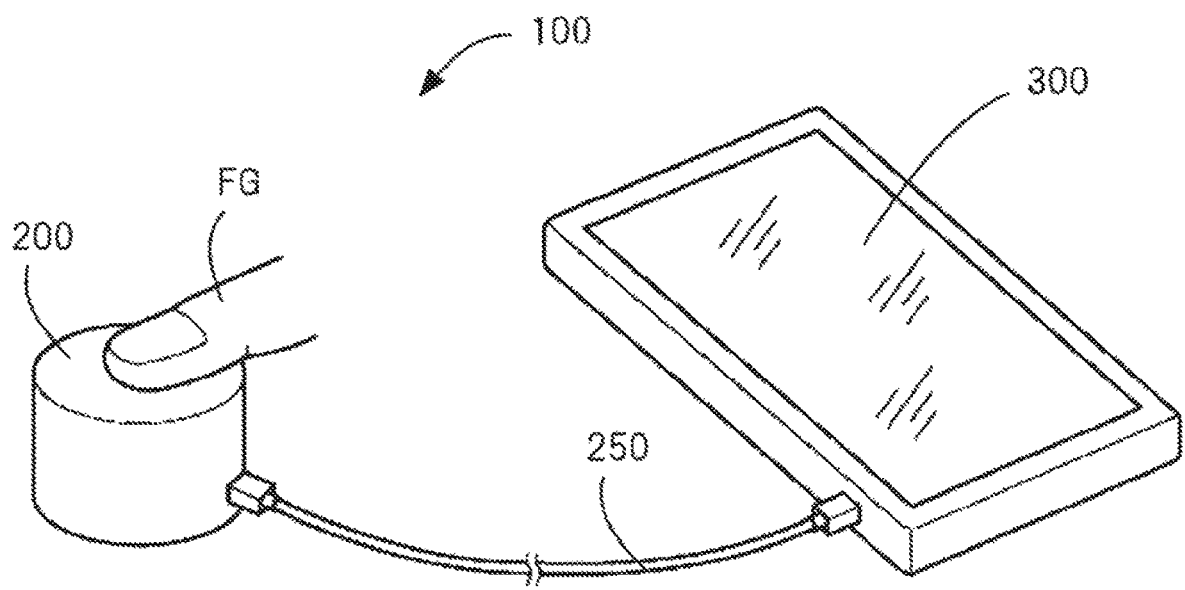

FIGS. 1A and 1B are perspective views illustrating a first configuration example of a blood flow volume measuring device 100 according to a first embodiment. The blood flow volume measuring device 100 includes a blood flow volume sensor 200 and electronic equipment 300. The electronic equipment 300 includes, for example, a mobile terminal device, a smart phone, a mobile phone, a tablet terminal, and other electronic equipment.

The blood flow volume sensor 200 comes into contact with a measuring-target region (for example, a finger FG of a person), emits light from a light source to the measuring-target region, and receives light scattered at the measuring-target region. The electronic equipment 300 acquires information on a light receiving amount obtained by the blood flow volume sensor 200, and measures a flow volume of liquid (for example, blood) flowing through the measuring-target region based upon the information on the light receiving amount.

In the blood flow volume measuring device 100 illustrated in FIGS. 1A and 1n, the blood flow volume sensor 200 and the electronic equipment 300 are separately provided. The blood flow volume sensor 200 and the electronic equipment 300 are connected to each other through a wire or wirelessly, and information on the light receiving amount measured by the blood flow volume sensor 200 is transmitted to the electronic equipment 300. In FIGS. 1A and 1B, the blood flow volume sensor 200 and the electronic equipment 300 are connected to each other by a micro USB (Universal Serial Bus) 250. In FIG. 1B, a finger FG is in contact with a protrusion 60 provided on the blood flow volume sensor 200 for measuring a blood flow volume.

Figure 2A:
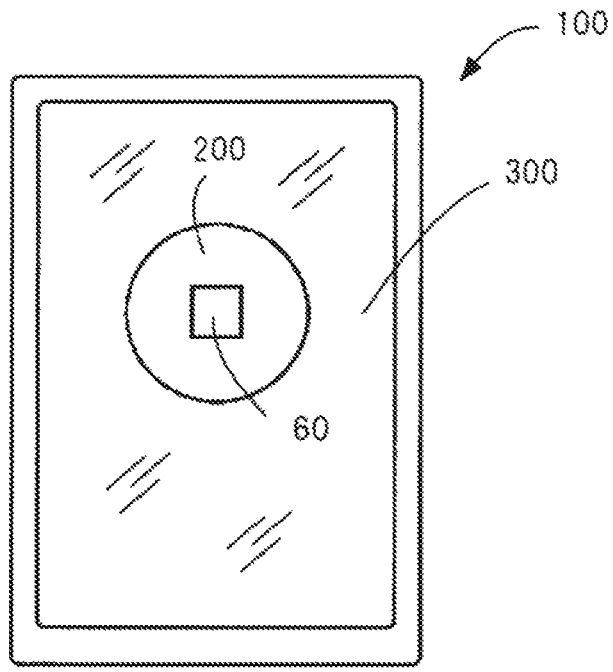
FIGS. 2A and 2B are schematic diagrams illustrating a second configuration example of a blood flow volume measuring device including a blood flow volume sensor and electronic equipment.
Figure 2B:
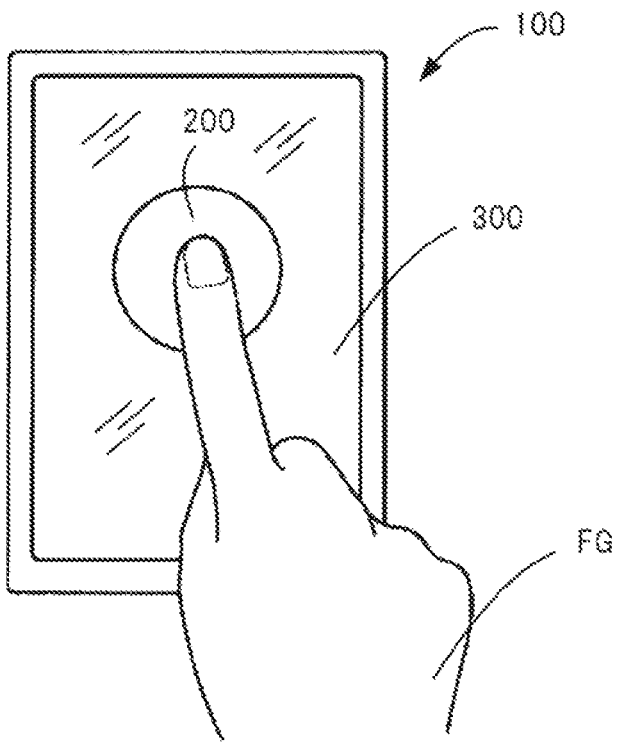

FIGS. 2A and 2B are perspective views illustrating a second configuration example of the blood flow volume measuring device 100. The blood flow volume measuring device 100 includes the blood flow volume sensor 200 and the electronic equipment 300. In FIGS. 2A and 2B, the blood flow volume sensor 200 is built in the electronic equipment 300. In this way, the blood flow volume sensor 200 and the electronic equipment 300 are integrally formed. In FIG. 2B, the finger FG is in contact with the protrusion 60 provided on the blood flow volume sensor 200 for measuring a blood flow volume.

Figure 3:
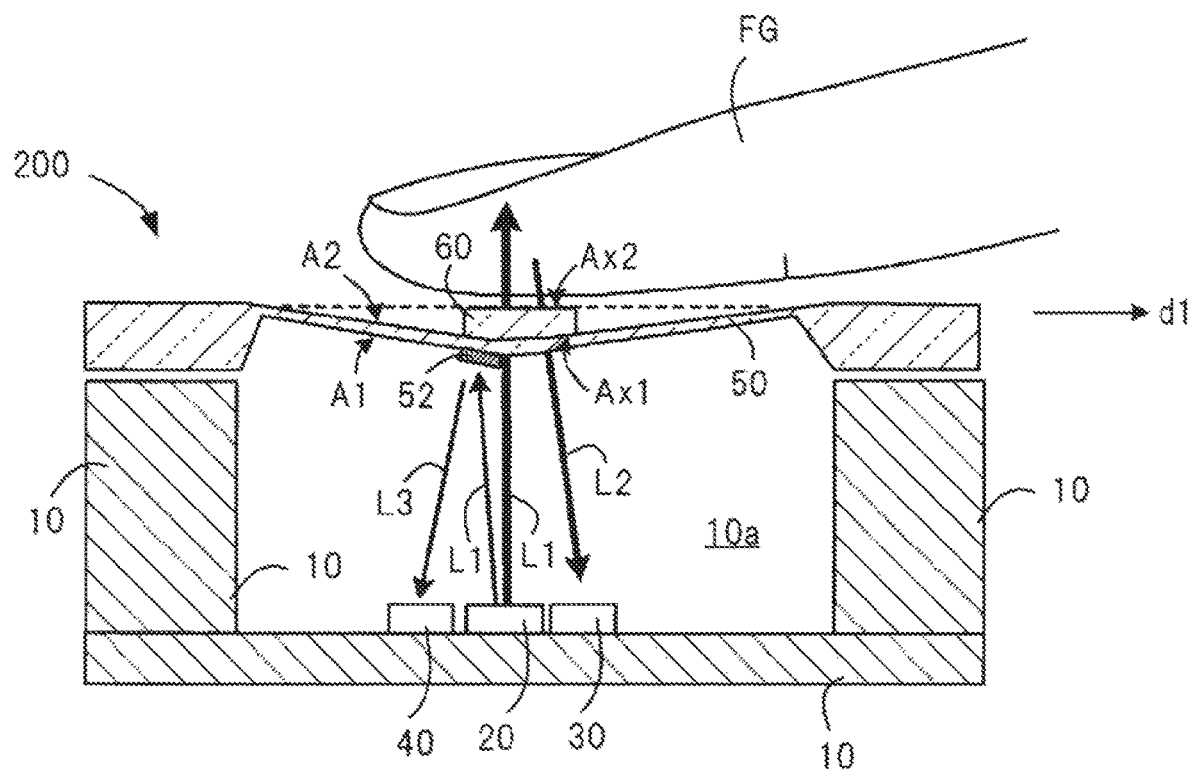
FIG. 3 is a cross-sectional view illustrating a first configuration example of a blood flow volume sensor according to a first embodiment.

FIG. 3 is a cross-sectional view illustrating a configuration example of the blood flow volume sensor 200 according to the first embodiment. The blood flow volume sensor 200 is provided with a base 10, a VCSEL 20, a first photodiode 30 and a second photodiode 40, an acrylic plate 50, and the protrusion 60.

The base 10 is formed to include silicon and ceramics, and accommodates each member (for example, the VCSEL 20, the first photodiode 30, and the second photodiode 40) of the blood flow volume sensor 200 thereinside. Further, the protrusion 60 is not accommodated inside the base 10. In the base 10, an upper part of the base 10 is covered with the acrylic plate 50. An upper end part of the base 10 fixes both end parts of the acrylic plate 50. Accordingly, an accommodation space 10a is formed inside of the base 10.

The VCSEL (Vertical Cavity Surface Emitting Laser) 20 emits light. At least part of light L1 emitted from the VCSEL 20 is directed toward the finger FG through the acrylic plate 50 and the protrusion 60. A wavelength of the emitted light L1 is, for example, a wavelength of near infrared light, and the wavelength thereof is, for example, 850 nm to 1300 nm. The emitted light L1 is reflected and scattered (hereinafter collectively and simply referred to as "scattering") by the finger FG, and becomes scattered light L2. The VCSEL 20 is one example of a light source Further, part of the emitted light L1 is reflected by a mirror 52 and becomes reflected light L3. The mirror 52 is adhered to a first surface A1 of the acrylic plate 50 facing the VCSEL 20.

The emitted light L1 is propagated in an approximately hemispherical shape while repeatedly being scattered or reflected by a blood cell or tissue in a capillary vessel in the measuring-target region (for example, the finger FG) in a biological tissue of a user. The scattered light L2 which is reflected or scattered by the finger FG from the emitted light L1 is received in the first photo diode 30.

The first photodiode 30 is a photodiode for a blood flow volume sensor (for measuring a blood flow volume). The first photodiode 30 receives the scattered light L2 from the finger FG. The first photodiode 30 photoelectrically converts the scattered light L2 to generate a light detection signal corresponding to the intensity of the scattered light L2. The light detection signal may be amplified by an amplifier (not illustrated). The first photodiode 30 is one example of a light receiving element.

The second photodiode 40 is a photodiode for detecting displacement. The second photodiode 40 receives the reflected light L3. The second photodiode 40 photoelectrically converts the reflected light L3 to generate a light detection signal corresponding to the intensity of the reflected light L3. The light detection signal may be amplified by an amplifier (not illustrated). The second photodiode 40 is one example of a pressure sensor.

Further, as described later, a deflection amount and an inclination of the acrylic plate 50, contact pressure and load distribution with respect to the protrusion 60 are derived based upon a detected value (the intensity of reflected light L3) by the second photodiode 40. The deflection amount of the acrylic plate 50 corresponds to a deflection amount y which will be described later. The inclination of the acrylic plate 50 corresponds to a change rate (dy/dx) and an inclination θ which will be described later.

The acrylic plate 50 has translucency with respect to the wavelengths of the emitted light L1 and the scattered light L2. That is, the acrylic plate 50 is disposed between the VCSEL 20 and the finger FG, and between the first photodiode 30 and the finger FG, thereby allowing the emitted light L1 and the scattered light L2 to pass through the acrylic plate 50. Additionally, in FIG. 3, in the acrylic plate 50, both ends of the acrylic plate 50 are fixed to the upper end of the base 10. Therefore, the acrylic plate 50 is formed as a doubly supported beam (a beam fixed at both ends). The acrylic plate 50 is one example of a translucent member.

The protrusion 60 is disposed on a second surface A2 of the acrylic plate 50 facing the finger FG. The protrusion 60 is disposed, for example, at a center part of the acrylic plate 50. The protrusion 60 has translucency with respect to the wavelengths of the emitted light L1 and the scattered light L2. That is, the protrusion 60 is disposed between the VCSEL 20 and the finger FG, and between the first photodiode 30 and the finger FG, thereby allowing the emitted light L1 and the scattered light L2 to pass through the protrusion 60.

The protrusion 60 is formed, for example, by an acrylic material. In this case, the material thereof is the same as the acrylic plate 50, such that a refractive index difference at a boundary between the acrylic plate 50 and the protrusion 60 becomes small, and thus the light permeability becomes high. Further, the protrusion 60 may be formed of a member having translucency other than the acrylic material.

Further, a first surface Ax1 contacting with the acrylic plate 50 of the protrusion 60 is smaller than a second surface Ax2 of the acrylic plate 50 (an area is small). Further, the finger FG can contact with a whole surface of the second surface Ax2 contacting with the finger FG of the protrusion 60. That is, the second surface Ax2 of the protrusion 60 is smaller than the finger FG contacting with the protrusion 60. Therefore, when the protrusion 60 is pressed by the finger FG, the finger FG contacts with the whole surface of the second surface Ax2 of the protrusion 60, such that the contact pressure per a unit area of the protrusion 60 easily becomes constant. The protrusion 60 is one example of a contact member.

Figure 4:
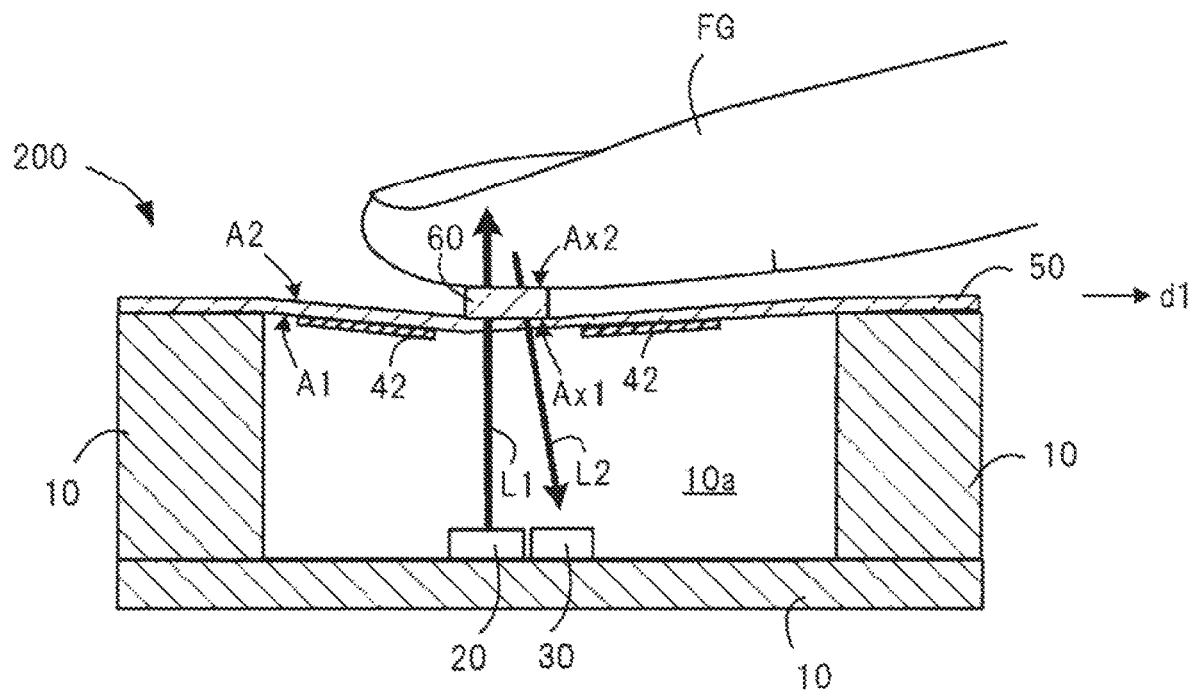
FIG. 4 is a cross-sectional view illustrating a second configuration example of a blood flow volume sensor according to a second embodiment.

FIG. 4 is a cross-sectional view illustrating a second configuration example of the blood flow volume sensor 200. In FIG. 4, the blood flow volume sensor 200 is provided with the base 10, the VCSEL 20, the first photodiode 30, and a strain gauge 42, the acrylic plate 50, and the protrusion 60. That is, in FIG. 4, in comparison with FIG. 3, the blood flow volume measuring device 100 is not provided with the second photodiode 40 and the mirror 52 but is provided with the strain gauge 42.

In FIG. 4, with respect to the same components as those of FIG. 3, the same reference sings are denoted thereto, and descriptions thereof will be omitted or will be simply described.

The strain gauge 42 is, for example, attached on the acrylic plate 50, thereby being mounted on the first surface A1. Further, a plurality of (for example, two strain gages) the strain gauges 42 are provided. The strain gauge 42 includes, for example, a metal foil disposed in a zigzag shape on an insulator, and electrical resistance thereof is changed by deformation. Additionally, as described later, the deflection amount of the acrylic plate 50 and the inclination thereof, and the contact pressure against the protrusion 60 and the load distribution thereto are derived based upon a measured value (a change in the electrical resistance) by the strain gauge 42.

Next, a load applying method with respect to the protrusion 60 will be described. For example, as the load applying method, the following first to third load applying methods will be considered.

As illustrated in FIGS. 3 and 4, the first load applying method is a method in which the finger FG is moved to contact with the protrusion 60, and the load is applied thereto.

The second load applying method is a method in which the finger FG is fixed and the blood flow volume sensor 200 including the protrusion 60 is moved, after which the finger FG and the protrusion 60 are brought into contact with each other and the load is applied thereto.

Figure 5:
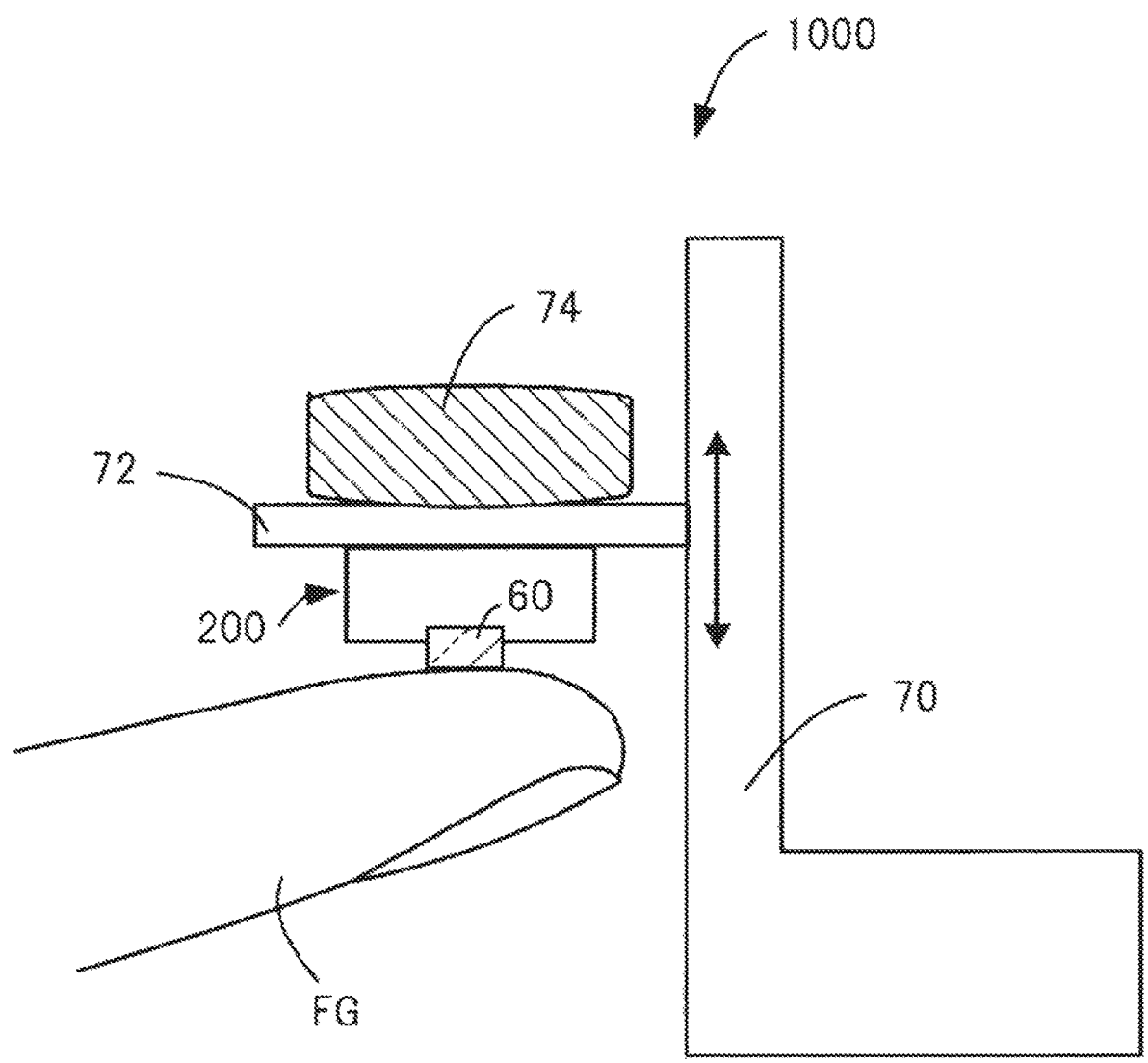
FIG. 5 is a cross-sectional view illustrating a configuration example of a blood flow volume measuring system that applies a load by a second load applying method.

FIG. 5 is a cross-sectional view illustrating a configuration example of a blood flow volume measuring system 1000 that applies the load by the second load applying method. In FIG. 5, applying the load is performed by using a guide rail 70 and a weight 74. In FIG. 5, with respect to the same components as those of FIGS. 3 and 4, the same reference sings are denoted thereto, and descriptions thereof will be omitted or will be simply described.

The blood flow volume measuring system 1000 includes the blood flow volume sensor 200 including the protrusion 60, the electronic equipment 300 (not illustrated), the guide rail 70, a base 72, and the weight 74. The configuration of the blood flow volume sensor 200 may be the same as those of FIGS. 3 and 4. In the second load applying method, the blood flow volume sensor 200 is installed in a direction opposite to a vertical direction of the first load applying method. In the blood flow volume sensor 200, the protrusion 60 is disposed at an end part in a vertically downward direction.

The guide rail 70 is, for example, formed in an L-shape and the base 72 is connected to a preset connection range. The base 72 is slidable in an up-and-down direction along a vertical direction of the guide rail 70. The weight 74 is placed on an upper surface of the base 72. An arbitrary load is applied downward in the vertical direction by the weight 74. The blood flow volume sensor 200 is fixed to a lower surface of the base 72.

The finger FG is fixedly positioned to face the protrusion 60 under the blood flow sensor 200. That is, in the first load applying method, the finger FG is moved to allow the finger FG to contact with the protrusion 60. However, in the second load applying method, the finger FG is fixed, and the base 72 is moved to allow the protrusion 60 to contact with the finger FG.

According to the second load applying measuring method, even when the load is applied by using the guide rail 70 and the weight 74, the blood flow volume measuring system 1000 can appropriately apply the load to the protrusion 60 by the finger FG. Further, since the finger FG is fixed, it is possible to prevent an error of applying the load caused by the movement of the finger FG, and to prevent a variation in the measured value, thereby improving reproducibility of a measurement result.

The third load applying measuring method is a method in which the finger FG is sandwiched and held by clips, and the finger FG and the protrusion 60 are brought into contact with each other, thereby applying the load thereto.

Figure 6A:
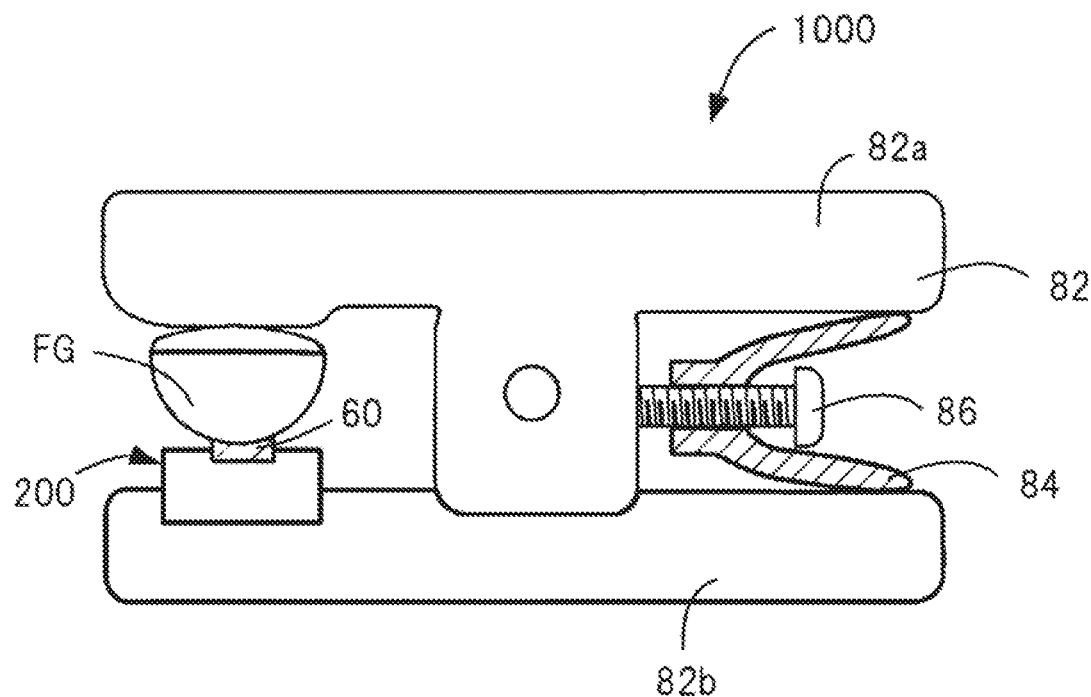
FIGS. 6A and 6B are cross-sectional views illustrating a configuration example of a blood flow volume measuring system that applies a load by a third load applying method.
Figure 6B:
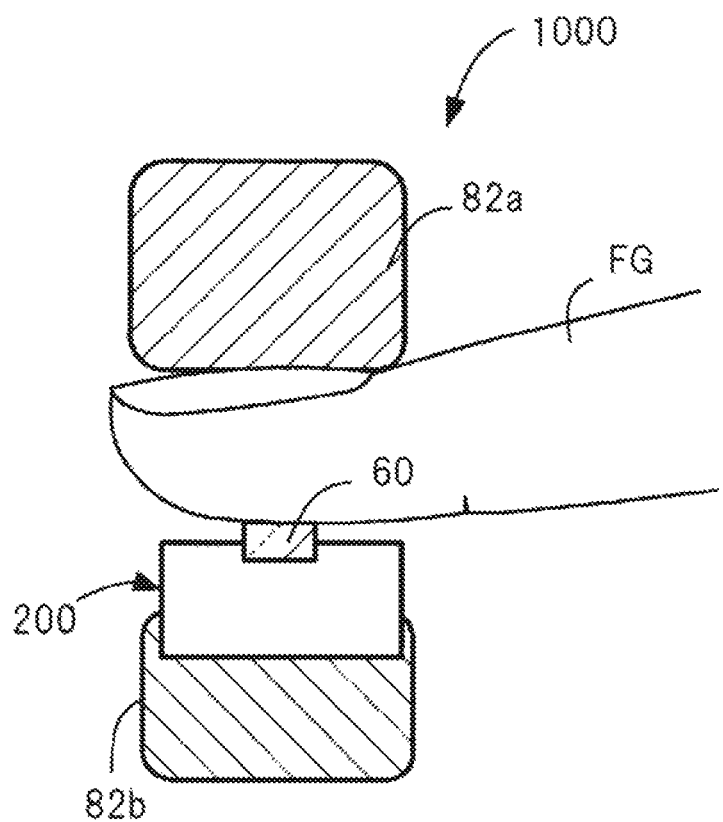

FIGS. 6A and 6B are cross-sectional views illustrating a configuration example of the blood flow volume measuring system 1000 that applies the load by the third load applying method. The blood flow volume measuring system 1000 includes the blood flow volume sensor 200 including the protrusion 60, the electronic equipment 300 (not illustrated), a clip 82, a leaf spring 84, and a screw 86. The configuration of the blood flow volume sensor 200 may be the same as those of FIGS. 3 and 4.

The clip 82 includes a clip upper part 82a and a clip lower part 82b. The blood flow volume sensor 200 is mounted on the clip lower part 82b at a preset position, and the protrusion 60 protrudes to a space (a measurement space) sandwiched between the clip upper part 82a and the clip lower part 82b. When measuring the blood flow volume, the finger FG is inserted into the measurement space. The clip 82 holds the finger FG in a state where the finger FG is in contact with the protrusion 60.

The leaf spring 84 urges the clip upper part 82a and the clip lower part 82b in a direction separating from each other. An urging force of the leaf spring 84 is adjusted by a screwed state of the screw 86. The screw 86 screws the leaf spring 84 into the clip 82. A distance between the clip upper part 82a and the clip lower part 82b is varied by the leaf spring 84 by turning the screw 86, whereby the load applied on the protrusion 60 by the finger FG is varied.

Further, for convenience herein, the clip upper part 82a and the clip lower part 82b are used, however, the clip upper part 82a may not be necessarily required to be disposed on the upper side in the vertical direction and the clip lower part 82a may not be necessarily required to be disposed on the lower side in the vertical direction.

Next, an electrical configuration of the blood flow volume measuring device 100 will be described.

Figure 7:
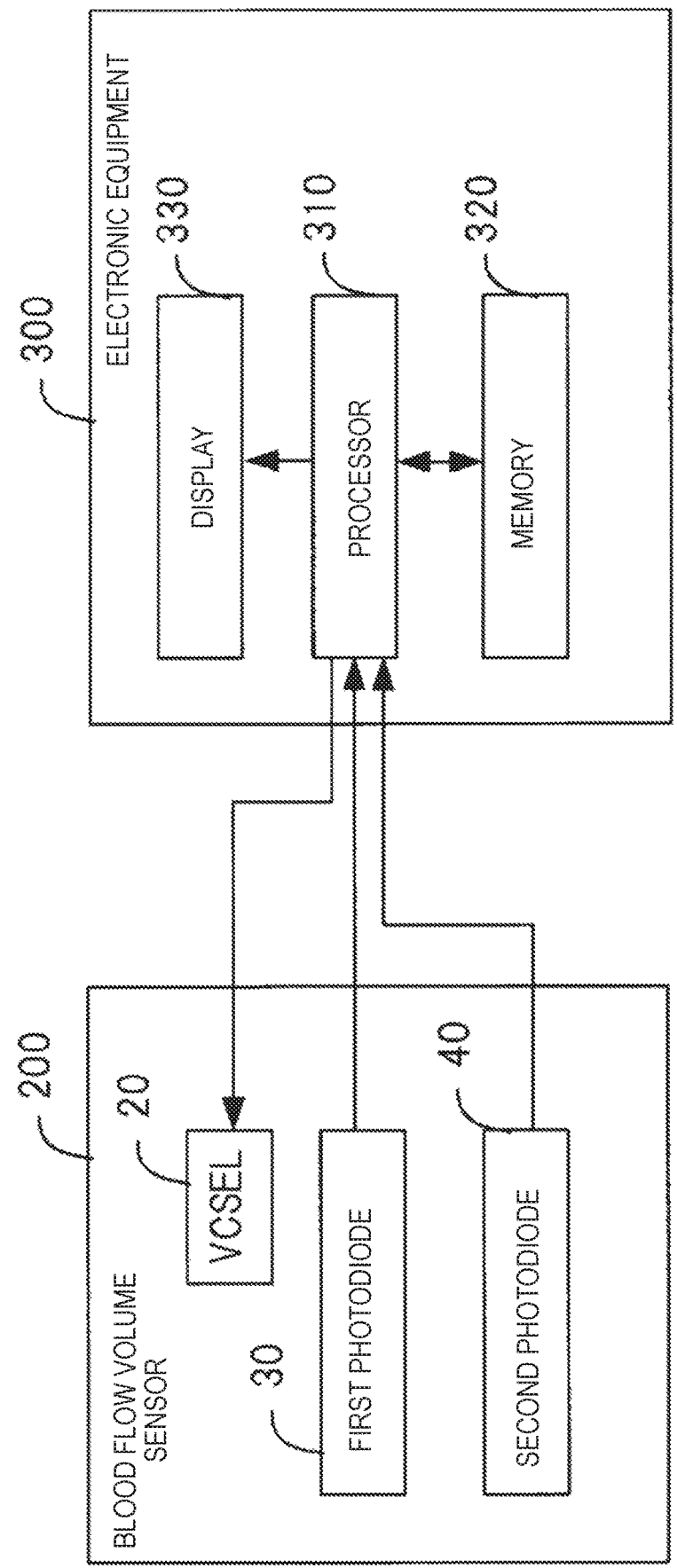
FIG. 7 is a block diagram illustrating an electrical configuration example of the blood flow volume measuring device.

FIG. 7 illustrates a block diagram illustrating one example of the electrical configuration of the blood flow volume measuring device 100. Here, as illustrated in FIG. 3, an example in which the second photodiode 40 is provided is illustrated.

The blood flow volume sensor 200 is provided with the VCSEL 20, the first photodiode 30, and the second photodiode 40. The electronic equipment 300 is provided with a processor 310, a memory 320, and a display 330.

In the blood flow volume sensor 200, the VCSEL 20 emits the emitted light L1 by driving a laser driving circuit (not illustrated). Driving of the laser driving circuit may be performed according to a control signal from the electronic equipment 300. Further, the VCSEL 20 may transmit information relating to the emitted light L1 (information on an amount of light emission of the emitted light L1 and a wavelength thereof) to the electronic equipment 300.

The first photodiode 30 transmits the light detection signal including information (detection information) on the light receiving amount of the scattered light L2 and light receiving intensity thereof to the electronic equipment 300.

The second photodiode 40 transmits the light detection signal including information (detection information) on the light receiving amount of the reflected light L3 and light receiving intensity thereof to the electronic equipment 300.

Further, when the blood flow volume sensor 200 is provided with the strain gauge 42, a detected value (detection information) detected by the strain gauge 42 is transmitted to the electronic equipment 300.

In the electronic equipment 300, the processor 310 acquires (for example, receives) the detection information from the blood flow volume sensor 200. The processor 310 may transmit the control signal to the blood flow volume sensor 200.

The processor 310 includes, for example, an MPU (Micro Processing Unit), and a CPU (Central Processing Unit), or a DSP (Digital Signal Processor).

The processor 310 executes a program held in the memory 320, thereby performing various kinds of processing. The various kinds of processing include, for example, a computation relating to blood flow volume measurement, and warning information display. Details of the various kinds of processing executed by the processor 310 will be described later.

The memory 320 includes, for example, a primary storage device such as a ROM (Read Only Memory), a RAM (Random Access Memory), and the like. Further, the memory 320 may also include a secondary storage device such as an SD card, and the like. The memory 320 holds various kinds of data and programs. The memory 320 may be embedded in the processor 310.

The display 330 includes, for example, an LCD (Liquid Crystal Display), thereby displaying various kinds of data. The display 330 displays an image, a character, a symbol, a figure, or data of any combination in which two or more thereof are combined with each other. For example, the display 330 displays the warning information relating to the blood flow volume measurement.

Accordingly, the blood flow volume measuring device 100 can urge a user so that, for example, the contact of the finger FG with the protrusion 60 becomes equal load distribution, that is, the contact pressure per unit area becomes constant.

Next, a processing example executed by the processor 310 will be described.

The processor 310 computes the deflection amount and the inclination of the acrylic plate 50 based upon the detection information (for example, an intensity change of the reflected light L3) from the second photodiode 40. The inclination of the acrylic plate 50 is indicated by an inclination with respect to a reference direction, for example, (here, an extending direction dl of the acrylic plate 50 when no load is applied thereto, and a horizontal direction in FIGS. 3 and 4). Further, the processor 310 computes the contact pressure against the protrusion 60 caused by the finger FG based upon the deflection amount and the inclination of the acrylic plate 50, thereby estimating the load distribution on the protrusion 60.

In the same manner, when the blood flow volume sensor 200 is provided with the strain gauge 42, the processor 310 computes the deflection amount and the inclination of the acrylic plate 50 based upon the detection information of the strain gauge 42. Further, the processor 310 computes the contact pressure against the protrusion 60 caused by the finger FG based upon the deflection amount and the inclination of the acrylic plate 50, thereby estimating the load distribution on the protrusion 60.

Further, the processor 310 computes the blood flow volume based upon the detection information by the first photodiode 30 by using Doppler shift. The computation of the blood flow volume may be started at an arbitrary timing. Further, the processor 310 computes (measures) the contact pressure against the protrusion 60 (that is, the contact pressure against the acrylic plate 50), and detects that the contact pressure against the protrusion 60 is a preset contact pressure (for example, 80 mmHg), after which the computation of the blood flow volume may be started. Further, the computation of the blood flow volume may be performed while sequentially changing the contact pressure against the protrusion 60. The processor 310 has a function as a flow volume measuring unit.

For example, in the scattered light L2 scattered by a blood cell moving in the capillary of the finger FG, a frequency shift is generated by the Doppler effect proportional to a moving speed of the blood cell. In the scattered light L2 from a stationary tissue and the scattered light L2 from the moving blood cell, a frequency difference (shift) therebetween is distributed in the band of about several hundreds of Hz to several tens of kHz.

Therefore, in a power spectrum of a beat signal (beat signal) generated by interference between the two scattered lights L2, the frequency shifted by the Doppler effect corresponds to the speed of the blood cell, and power corresponds to an amount of the blood cell. A blood flow volume is the sum of products of the speed of each blood cell and the number of blood cells. Therefore, the processor 310 can compute the blood flow volume by multiplying the power spectrum of the above-mentioned beat signal by the frequency and integrating the resultant value.

The processor 310 performs frequency analysis on an interference component of the scattered light L2 (for example, FFT (Fast Fourier Transform) computation) with respect to the detection information from the first photodiode 30. The processor 310 derives (computes) a spectral sequence of the beat signal by the frequency analysis, and multiplies each spectral sequence by the corresponding frequency and integrates it, thereby deriving (computing) the blood flow volume of the finger FG. Further, the processor 310 may display the information relating to the blood flow volume as a measurement result through the display 330.

Figure 8:
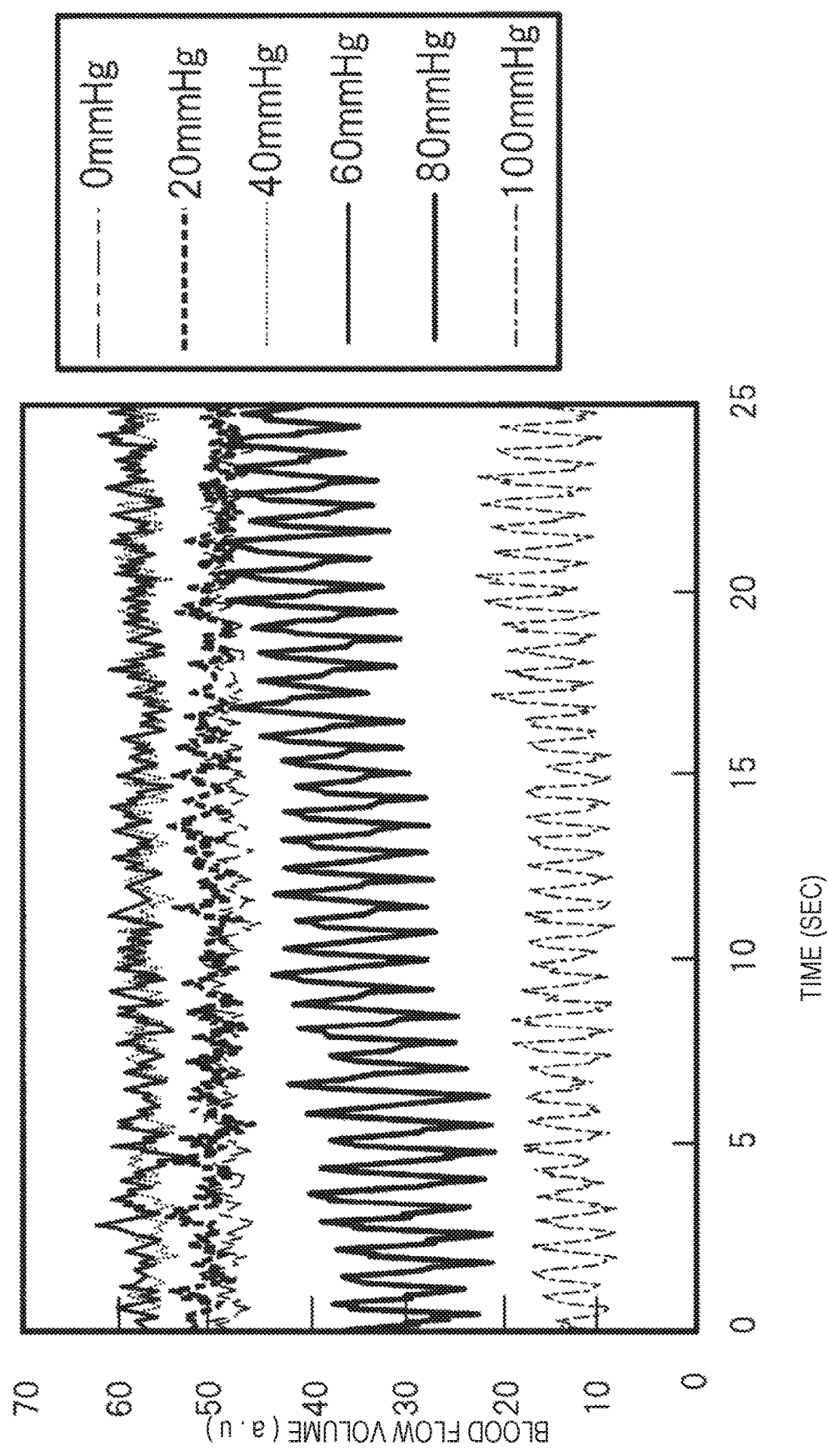
FIG. 8 is a schematic diagram illustrating an example of a change in a blood flow volume depending on contact pressure.

Next, a change in the blood flow volume caused by the contact pressure will be considered. FIG. 8 is a schematic diagram illustrating an example of a change in the blood flow volume depending on the contact pressure against the finger FG.

FIG. 8 illustrates a temporal change of the blood flow volume (unit: a, u) at each pressure of 0, 20, 40, 60, 80, and 100 (unit: mmHg). Referring to FIG. 8, it can be understood that amplitude (pulse wave amplitude) of a blood flow volume waveform is relatively small at the contact pressure of 0, 20, 40, and 60 (mmHg), and the pulse wave amplitude is relatively large at the contact pressure of 80 and 100 (mmHg). Further, it can be understood that the pulse wave amplitude becomes large when, particularly, the contact pressure is 80 (mmHg). Additionally, the pulse wave amplitude is also related to blood pressure measurement.

In the blood flow volume measurement using the Doppler shift of the scattered light L2 scattered by the finger FG, the blood flow volume measurement can be stably performed when the amplitude of the blood flow volume waveform is large, such that the reproducibility thereof is high. Therefore, it is desirable that the blood flow volume is measured in a state where the finger FG maintains a constant contact pressure (for example, 80 (mmHg)) against the blood flow volume sensor 200.

On the other hand, even in the case of 80 (mmHg) and 60 (mmHg) where the contact pressure does not change so much, it can be understood that the amplitude of the blood flow volume waveform is significantly reduced. Accordingly, it means that the measured value of the blood flow volume significantly changes depending on increasing or decreasing of a pressing force at the time of sensitive contact with the blood flow volume sensor 200.

In the embodiment, the blood flow volume measuring device 100 may measure the blood flow volume when the contact pressure against the protrusion 60 is a preset contact pressure (for example, 80 (mmHg)). That is, when the contact pressure against the protrusion 60 is the preset contact pressure (for example, 80 (mmHg)), emission of the emitted light L1 and reception of the scattered light L2 relating to the blood flow volume measurement may be performed. The contact pressure may be derived, for example, based upon the deflection amount detected by the second photodiode 40 or the strain gauge 42, or may be detected by being provided with another pressure sensor.

Next, the distribution of contact pressure at a finger FG will be considered.

Figure 9A:
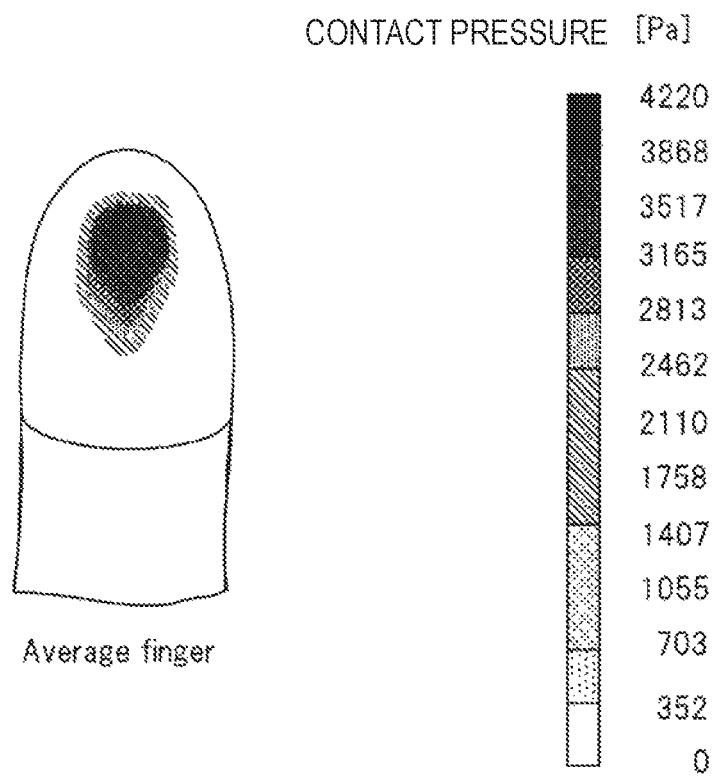
FIG. 9A is a schematic diagram illustrating a distribution example of contact pressure at a fingertip portion.
Figure 9B:
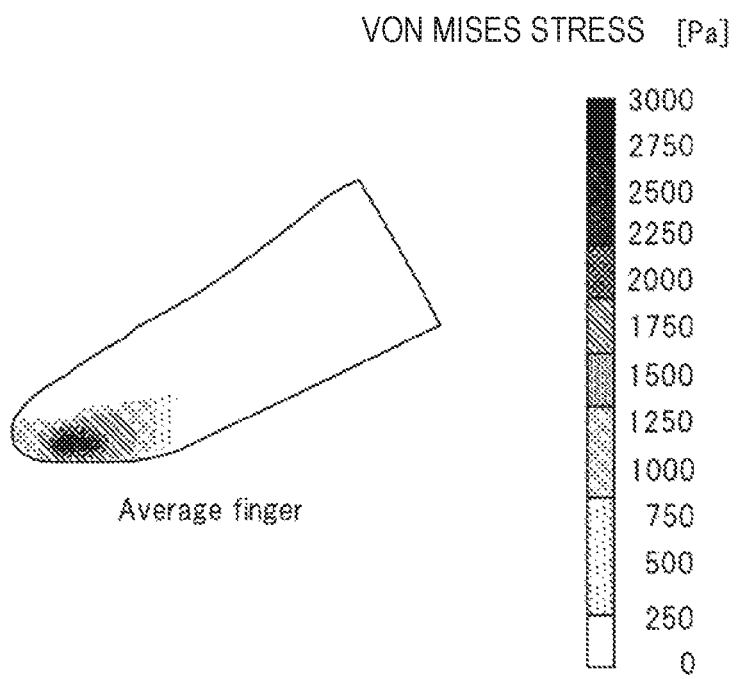
FIG. 9B is a schematic diagram illustrating a distribution example of Von Mises stress at the fingertip portion.

FIG. 9A is a schematic diagram illustrating one example of contact pressure distribution of the finger FG (a fingertip of a user). FIG. 9B is a schematic diagram illustrating one example of Von Mises stress distribution at the finger FG (the fingertip of the user).

As illustrated in FIGS. 9A and 9B, it can be understood that a range in which the contact pressure and the Von Mises stress are equal to each other is narrow, and the contact pressure and the Von Mises stress change depending on a contact portion even in a narrow range as that of the fingertip. Accordingly, it means that the measured value of the blood flow volume largely changes depending on a contact position in the finger FG with respect to the blood flow volume sensor 200.

Therefore, in the embodiment, the blood flow volume measuring device 100 is provided with the protrusion 60 so that a whole surface thereof is easily pressed down by the finger FG as the measuring-target region. Accordingly, it is possible to prevent the measured value of the blood flow volume from being largely changed depending on the contact position of the finger FG.

Next, the contact pressure of every load distribution in the doubly supported beam will be considered.

First, a case in which the load distribution is equal load distribution will be described.

Figure 10A:
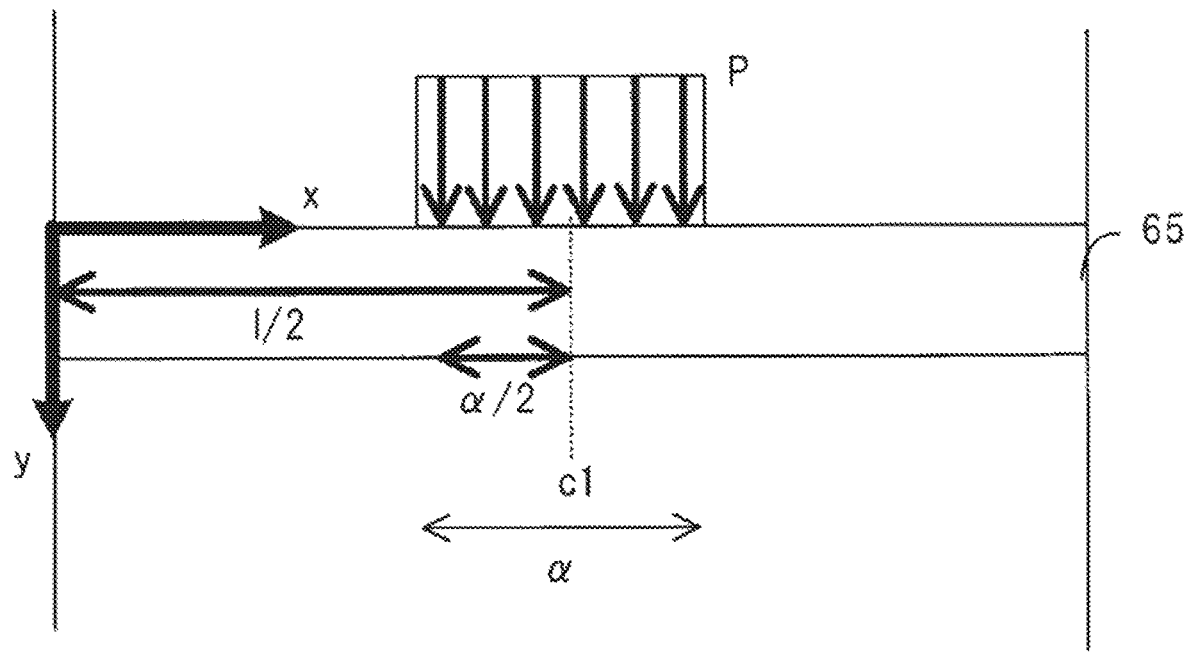
FIGS. 10A and 10B are schematic diagrams illustrating one example of a state of equal load distribution in a doubly supported beam.
Figure 10B:
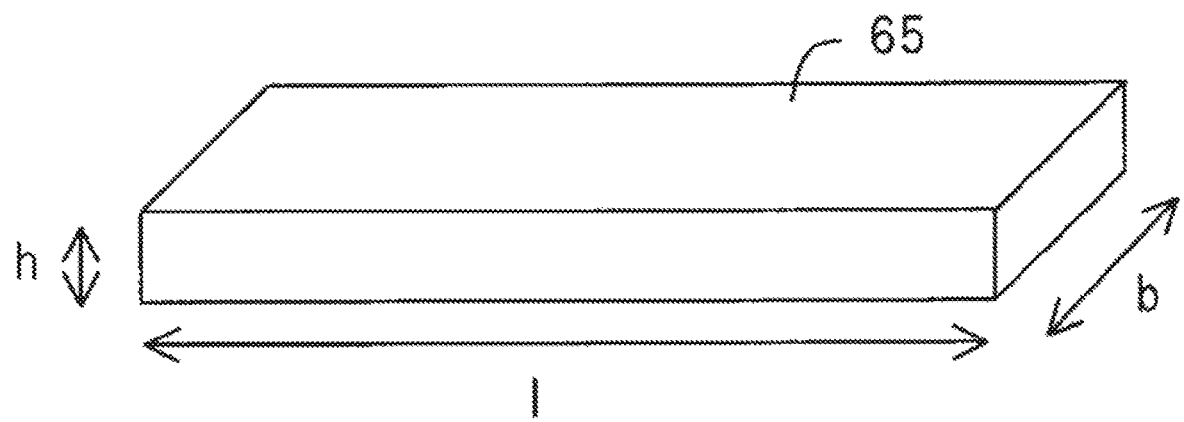

FIGS. 10A and 10B are schematic diagrams illustrating one example of the equal load distribution in a doubly supported beam 65 (simply, referred to as a "beam"). In the embodiment, each parameter is represented as follows:

"P": total load to the doubly supported beam 65

"α": length of the contact portion where the doubly supported beam 65 and the measuring-target region contact with each other "l": length of the doubly supported beam 65 in a longitudinal direction "b": length in a depth direction (a short-hand direction) of the doubly supported beams 65

"h": height of the doubly supported beam 65

"E": Young's modulus of the doubly supported beam 65

"I": secondary moment of a cross section of the doubly supported beam 65

A position in the longitudinal direction of the doubly supported beam 65 (a distance from a base point (a left end of the doubly supported beam 65 in FIG. 10A)) is represented by a variable x. A position in the height direction of the doubly supported beam 65 (a distance from a base point (an upper end of the doubly supported beam 65 in FIG. 10A)) is represented by a variable y. The variable y corresponds to the deflection amount of the doubly supported beam 65.

For example, the deflection amount (y) of the doubly supported beam 65 is represented by Equation 1 as follows:

Equation 1

$$y = \frac{P\{-4lx^3 + (3l^2 - \alpha^2)x^2\}}{48EIl} + \frac{P\left(x - \frac{l-\alpha}{2}\right)^4}{24EI\alpha} \qquad \text{(Equation 1)}$$

Accordingly, for example, the deflection amount (y(x=½)) at a center part (a beam center part c1) (x=½) of the doubly supported beam 65 is represented by Equation 2 as follows:

Equation 2

$$y\left(x = \frac{l}{2}\right) = \frac{P(2l^3 - 2l\alpha^2 + \alpha^3)}{384EI} \quad \text{(Equation 2)}$$

Accordingly, for example, a change rate (dy/dx) of the deflection amount (y) at each position in the longitudinal direction of the doubly supported beam 65 is represented by Equation 3. The change rate corresponds to a change in the deflection amount with respect to a minute change in the position in the longitudinal direction of the doubly supported beams 65.

Equation 3

$$\frac{dy}{dx} = \frac{P\{-6lx^2 + (3l^2 - \alpha^2)x\}}{24EIl} + \frac{P\left(x - \frac{l-\alpha}{2}\right)^3}{6EI\alpha} \quad \text{(Equation 3)}$$

Accordingly, for example, in the case of the equal load distribution, a change rate (dy/dx(x=½)) of the deflection amount (y) at the beam center part c1 is represented by Equation 4 as follows:

Equation 4

$$\frac{dy}{dx}\left(x = \frac{l}{2}\right) = 0 \quad \text{(Equation 4)}$$

Next, a case in which the load distribution is wedge load distribution will be described.

Figure 11:
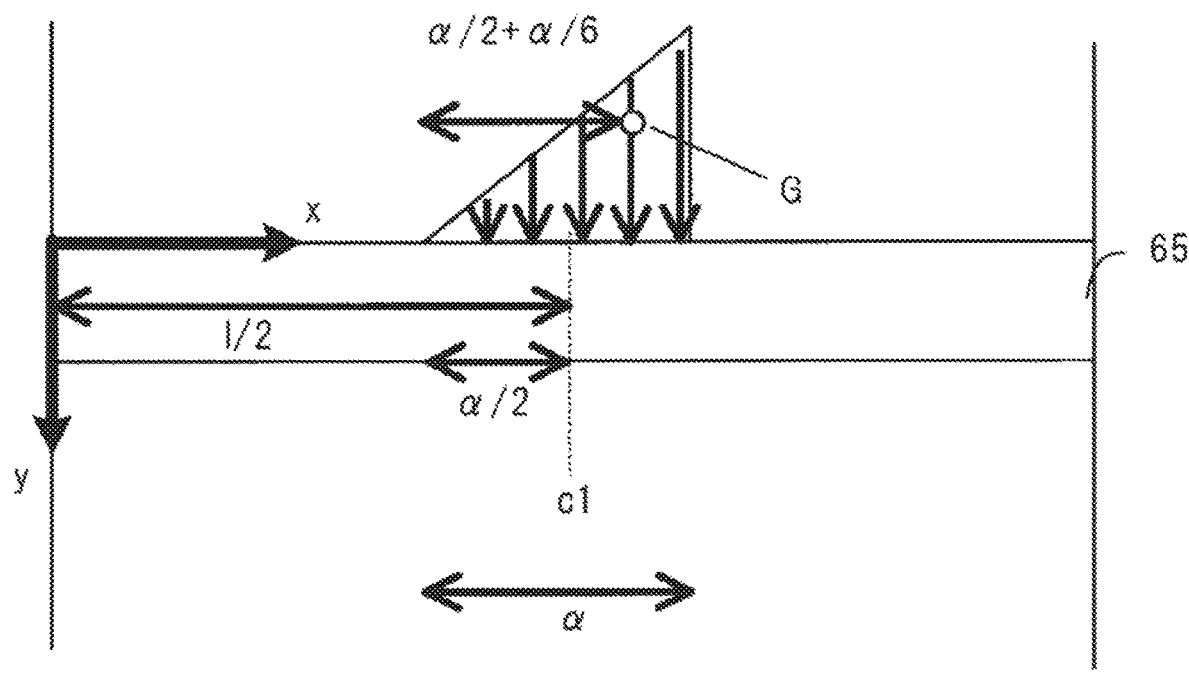
FIG. 11 is a schematic diagram illustrating one example of a state of wedge load distribution in the doubly supported beam.

FIG. 11 is a schematic diagram illustrating one example of wedge load distribution in the doubly supported beam 65. In the wedge load distribution illustrated in FIG. 11, the load gradually becomes large along the longitudinal direction of the doubly supported beam 65.

For example, the deflection amount (y) of the doubly supported beam 65 is represented by Equation 5 as follows:

Equation 5

$$y = \frac{P\left\{\begin{array}{l}-2(10l^3 - 5l^2\alpha + \alpha^3)x^3 + \\ (15l^3 - 5l^2\alpha - 5l^2\alpha - 5l\alpha^2 - 3\alpha^2)lx^2\end{array}\right\}}{240EIl^3} + \frac{P\left(x - \frac{l-\alpha}{2}\right)^3}{60EI\alpha^2} \quad \text{(Equation 5)}$$

Accordingly, for example, the deflection amount (y(x=½)) at the beam center part c1 (x=½) is represented by Equation 6 as follows:

Equation 6

$$y\left(x = \frac{l}{2}\right) = \frac{P\{2l^3 - 2l\alpha^2 + \alpha^3\}}{384EI} \quad \text{(Equation 6)}$$

Accordingly, for example, in the case of the wedge load distribution, the change rate (dy/dx(x=½)) of the deflection amount (y) at the beam center part c1 is represented by Equation 7 as follows:

Equation 7

$$\frac{dy}{dx}\left(x = \frac{l}{2}\right) = \frac{P\{10l^2\alpha - 15l\alpha^2 + 6\alpha^3\}}{960EI} \quad \text{(Equation 7)}$$

Further, the deflection amount (y) at a preset position (x=½+α/6) on the side opposite to the base end rather than the beam center part c1 is represented by Equation 8 as follows:

Equation 8

$$y\left(x = \frac{l}{2} + \frac{\alpha}{6}\right) = \quad \text{(Equation 8)}$$

$$\frac{P\left\{9(3l + \alpha)^2\left(\begin{array}{l}15l^4 - 10l^3\alpha - \\ 10l^2\alpha^2 + 6l\alpha^3 - \alpha^4\end{array}\right) + 512\alpha^3l^3\right\}}{233280EIl^3}$$

Accordingly, for example, in the case of the wedge load distribution, the change rate (dy/dx(x=½)) of the deflection amount (y) at the preset position (x=½+α/6) on the side opposite to the base end rather than the beam center part c1 is represented by Equation 9 as follows:

Equation 9

$$\frac{dy}{dx}\left(x = \frac{l}{2} + \frac{\alpha}{6}\right) = \quad \text{(Equation 9)}$$

$$\frac{P\left\{27(3l + \alpha)\left(\begin{array}{l}-5l^3\alpha - 5l^2\alpha^2 + \\ 3l\alpha^3 - \alpha^4\end{array}\right) + 640\alpha^2l^3\right\}}{38880EIl^3}$$

Accordingly, as illustrated in Equations 2 and 6, even in the case of the equal load distribution and the wedge load distribution, a value of the deflection amount y (x=½), that is, the deflection amount y of the beam center part c1 is propositional to the cube of the contact portion length a. Therefore, when the contact portion length a changes and thus the contact area changes, the deflection amount of the doubly supported beam 65 largely changes.

In the embodiment, the blood flow volume sensor 200 is provided with the protrusion 60, such that the contact area can be easily kept constant, and the contact portion length a can be easily kept constant, thereby making it possible to easily keep the deflection amount of the acrylic plate 50 constant.

Next, an influence of changes in the deflection amount y of the beam center part c1 and the contact length a will be considered. In this consideration, a first simulation is performed.

FIG. 12A is a schematic diagram illustrating one example of a parameter used for the first simulation. FIG. 12B is a graph illustrating one example of a relationship between the deflection amount y at the beam center part c1 and the contact length a. FIG. 12C is a graph illustrating one example of an influence of a change (an inclination) of the contact length with respect to the doubly supported beam 65.

According to FIG. 12B, it can be understood that as the contact length a becomes longer, the deflection amount y of the beam center part c1 gradually becomes smaller.

According to FIG. 12C, it can be understood that when the contact length a is short, a value of dy/dα approaches zero. That is, it understood that the change of the deflection amount y with respect to a minute change in the contact length a approaches zero, and the influence on the deflection amount y caused by the change in the contact length a is small.

Further, when the contact length a is about 20 mm, the value of dy/dα becomes minimum, on the other hand, the value of dy/dα becomes large as the contact length a becomes longer than 20 mm. This is because, here, it is set that the length 1 of the doubly supported beam 65=29.5 mm, and as the contact length a approaches the length 1, it becomes difficult to be deflected.

Accordingly, it can be said that even when a contact state of the finger FG with the blood flow volume sensor 200 slightly changes, the change in the deflection amount y of the doubly supported beam 65 is small. On the other hand, in a case where the contact length a is large, when the contact state of the finger FG with the blood flow volume sensor 200 slightly changes, the change in the deflection amount y of the doubly supported beam 65 is large. Therefore, it is desirable that the finger contacts with the blood flow volume sensor 200 with the contact length a as small as possible, that is, with the contact area as small as possible.

In the embodiment, the blood flow volume sensor 200 is provided with the protrusion 60 so that the contact area to the acrylic plate 50 formed as the doubly supported beam 65 becomes as small as possible. The blood flow volume measuring device 100 measures the blood flow volume by pressing down the acrylic plate 50 by the finger FG through the protrusion 60. Accordingly, the user can keep a small contact area with respect to the acrylic plate 50 through the protrusion 60 constant.

Further, when the user unintentionally slightly presses the acrylic plate 50 beyond a contact surface of the protrusion 60, the contact area to the acrylic plate 50 becomes changed, however, in this case, it is possible to reduce the influence on the change in the deflection amount y of the acrylic plate 50. Accordingly, the measurement result of the blood flow volume measurement is stabilized.

Next, a relationship between the deflection amount y of the beam center part c1 and the contact length a when the doubly supported beam 65 is formed of the acrylic material will be considered.

Figure 13:
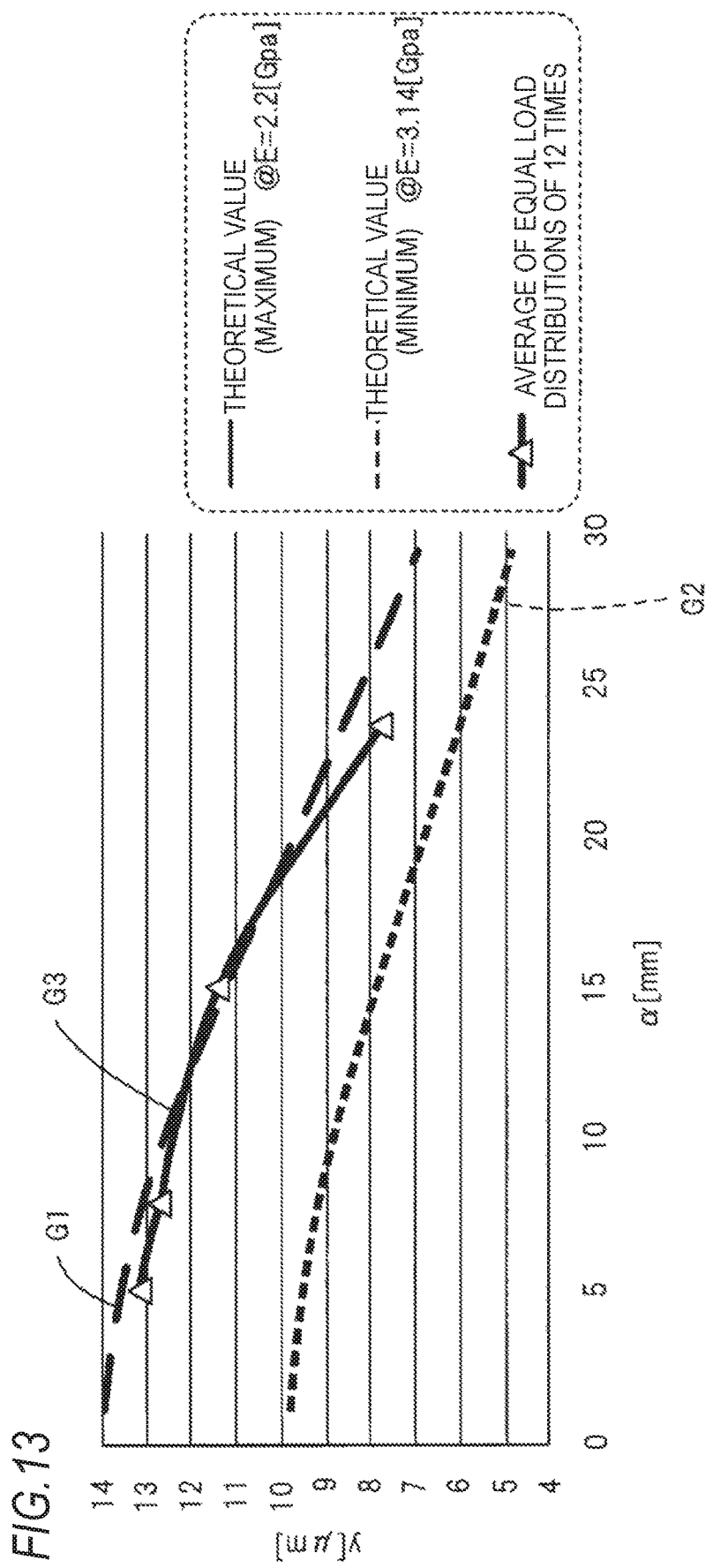
FIG. 13 is a graph illustrating one example of a relationship between a deflection amount at a center part of an acrylic beam and a contact length.

FIG. 13 is a graph illustrating a relationship between the deflection amount y of the beam center part C1 and the contact length a when the doubly supported beam 65 is formed of the acrylic material. FIG. 13 illustrates a graph G1 indicating a theoretical value of the deflection amount y with respect to the contact length a in the case of Young's modulus E=2.2 of the doubly supported beam 65. This theoretical value becomes the maximum value. Further, a graph G2 indicating a theoretical value of the deflection amount y with respect to the contact length a in the case of Young's modulus E=3.14 of the doubly supported beams 65. This theoretical value becomes the minimum value.

Further, FIG. 13 illustrates an average value of measurement results of the deflection amount y with respect to the contact length a when the load distribution is the equal load distribution. Here, the average value of the measurements of twelve times is indicated. According to FIG. 13, it can be understood that the actual measurement results are roughly included between the maximum theoretical value and the minimum theoretical value of the deflection amount y with respect to the contact length a. Further, the number of measurement times of the twelve times is one example, and the number of other measurement times may be used.

Next, the deflection amount y of the beam center part c1 and the inclination (dy/dx) for each load distribution will be considered. This consideration performs a second simulation.

FIG. 14 is a schematic diagram illustrating one example of a parameter used for the second simulation. In the second simulation, the deflection amount y and the inclination zero of the doubly supported beam 65 for each load distribution will be considered. Further, in FIG. 14, "bh^3" is indicated in a column of conditions of secondary moment of the cross section, and the like, which indicates "bh$^3$". That is, in each embodiment, "A^B" indicates "$A^B$" (A to the power of B).

Figure 15A:
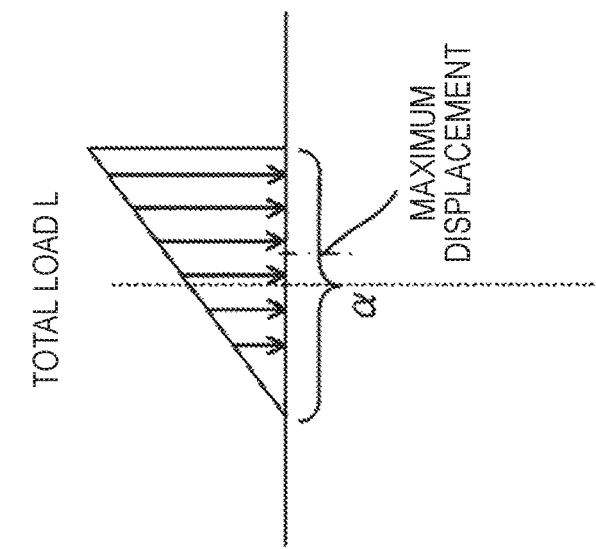
FIG. 15A is a schematic diagram illustrating one example of equal load distribution.
Figure 15B:
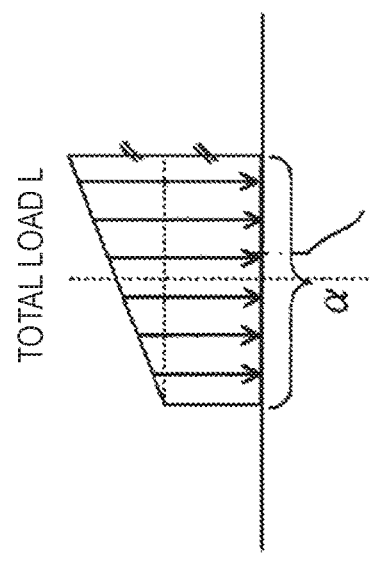
FIG. 15B is a schematic diagram illustrating one example of first wedge load distribution.
Figure 15C:
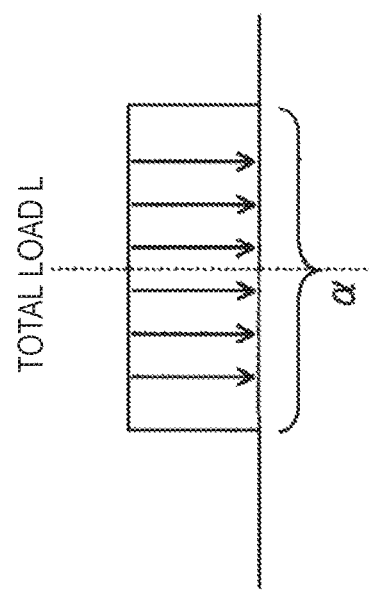
FIG. 15C is a schematic diagram illustrating one example of second wedge load distribution.

FIGS. 15A to 15C are schematic diagrams illustrating one example of the load distribution. FIG. 15A illustrates that a total load is L, and a load per unit area is the equal load distribution in which the load per unit area is constant over the whole body of the doubly supported beam 65. FIG. 15B illustrates that the total load having the same L is first wedge load distribution. FIG. 15C illustrates that the total load having the same L is second wedge load distribution.

In the first wedge load distribution illustrated in FIG. 15B, the minimum load position is a left end (referred to as an end part in a negative direction when viewed from the beam center part c1) of a contact portion with a measuring-target region of the doubly supported beam 65 in the drawing. The maximum load position is a right end (referred to as an end part in a positive direction when viewed from the beam center part c1) of the contact portion with the measuring-target region of the doubly supported beam 65 in the drawing. The load increases from the left end toward the right end by the same amount, and the load at the right end is two times larger than the load at the left end.

In the second wedge load distribution illustrated in FIG. 15C, the minimum load position is the left end of the contact portion with the measuring-target region of the doubly supported beam 65 in the drawing. The maximum load position is the right end of the contact portion with the measuring-target region of the doubly supported beam 65 in the drawing. The load increases from the left end toward the right end by the same amount, and a load value at the left end is zero.

Figure 16A:
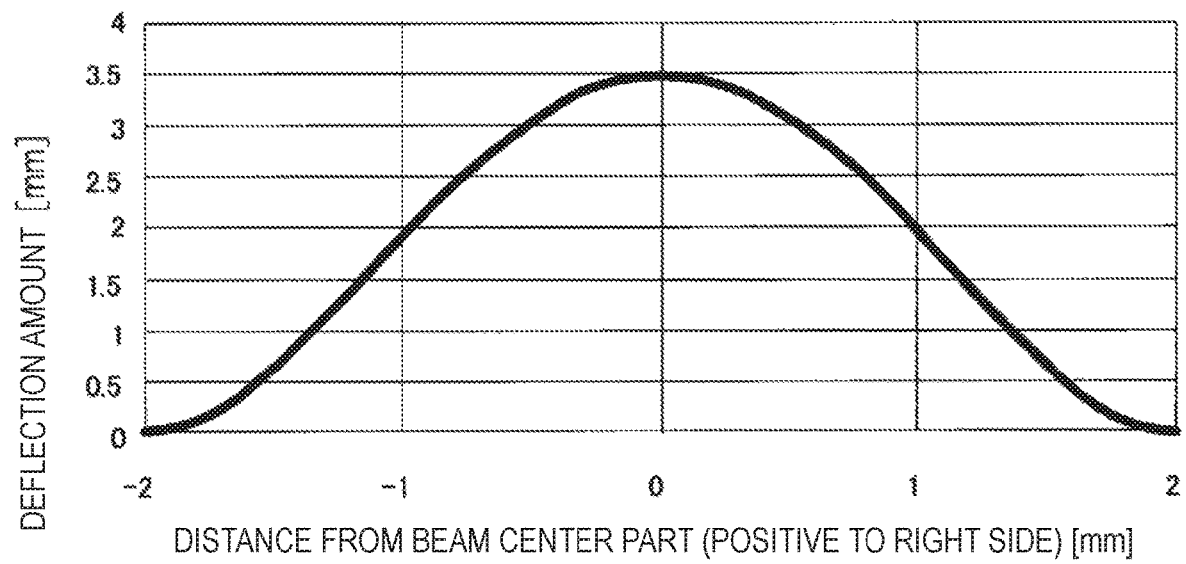
FIG. 16A is a graph illustrating one example of a relationship between a distance from a beam center part and a deflection amount of a doubly supported beam in equal load distribution.
Figure 16B:
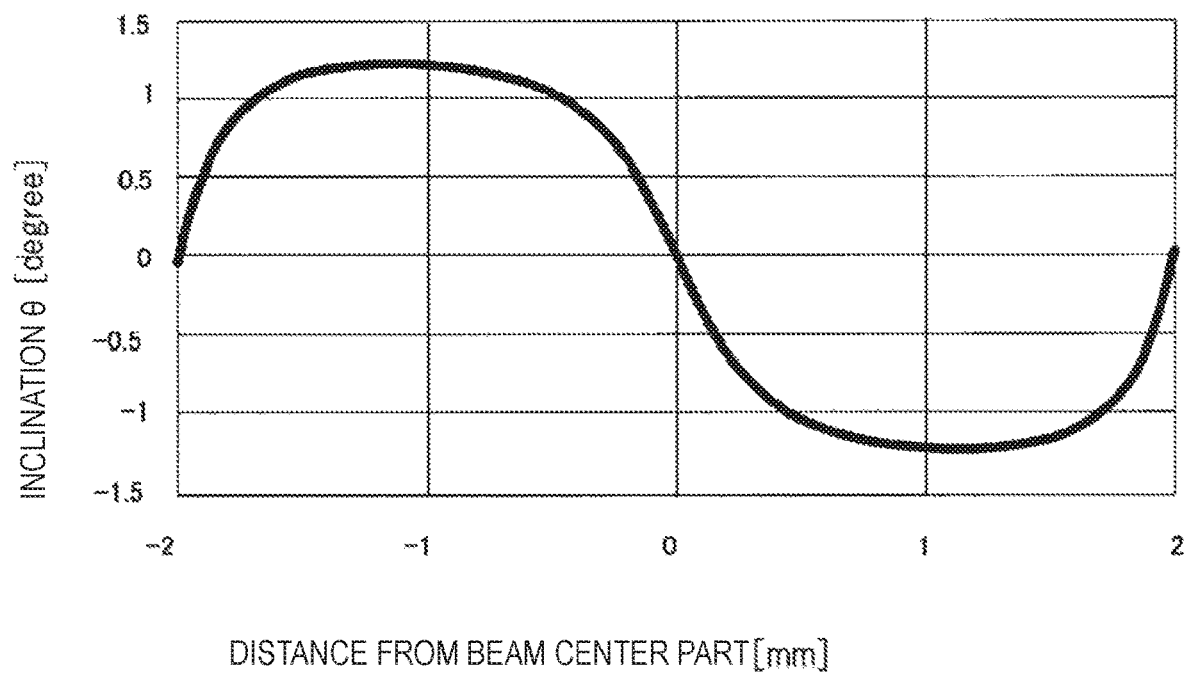
FIG. 16B is a graph illustrating one example of a relationship between the distance from the beam center part and an inclination of the doubly supported beam in the equal load distribution.

FIG. 16A is a graph illustrating one example of a relationship between a distance from the beam center part c1 in the equal load distribution and the deflection amount y of the doubly supported beam 65. FIG. 16B is a graph illustrating one example of a relationship between the distance from the beam center part c1 in the equal load distribution and an inclination θ of the doubly supported beam 65.

In the equal load distribution, the load is uniform at the contact portion with the measuring-target region of the doubly supported beam 65. Therefore, as illustrated in FIG. 16A, the deflection amount y at the beam center part c1 becomes maximum. Therefore, as illustrated in FIG. 16B, at the beam center part c1 where the deflection amount y is the largest, an extending direction of the doubly supported beam 65 when no load is applied to the doubly supported beam 65 becomes parallel thereto (for example, horizontal), whereby a value of the inclination θ becomes zero.

Further, the value of the inclination θ corresponds to the value of the change rate (dy/dx) of the deflection amount (y) at each position in the longitudinal direction of the doubly supported beam 65 (in a left-and-right direction in FIGS. 10 and 11).

Figure 17A:
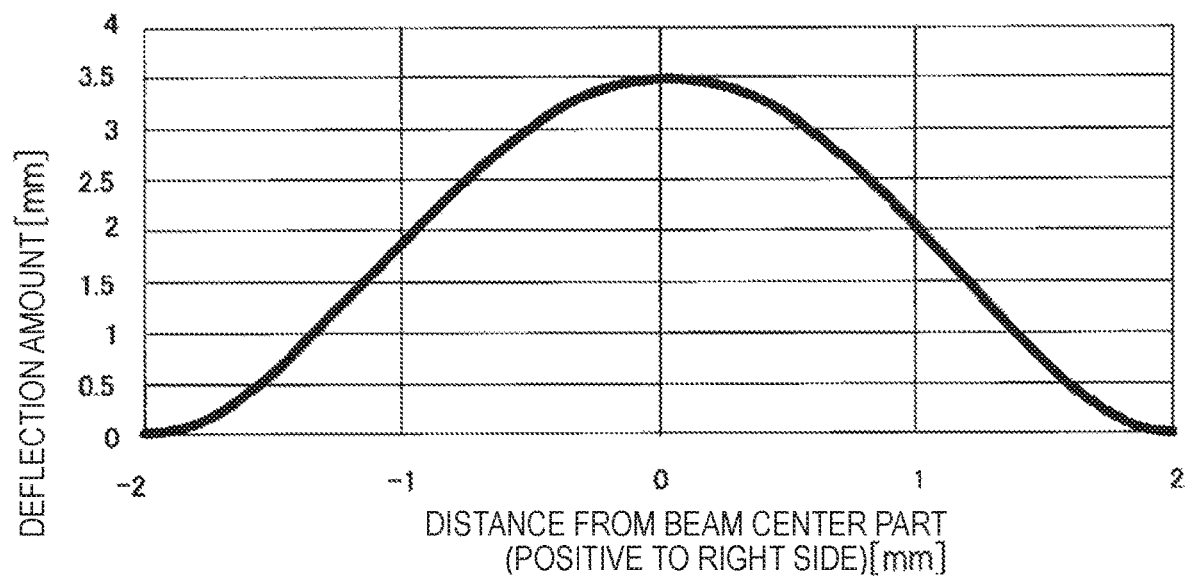
FIG. 17A is a graph illustrating one example of a relationship between a distance from a beam center part and a deflection amount of a doubly supported beam in first wedge load distribution.
Figure 17B:
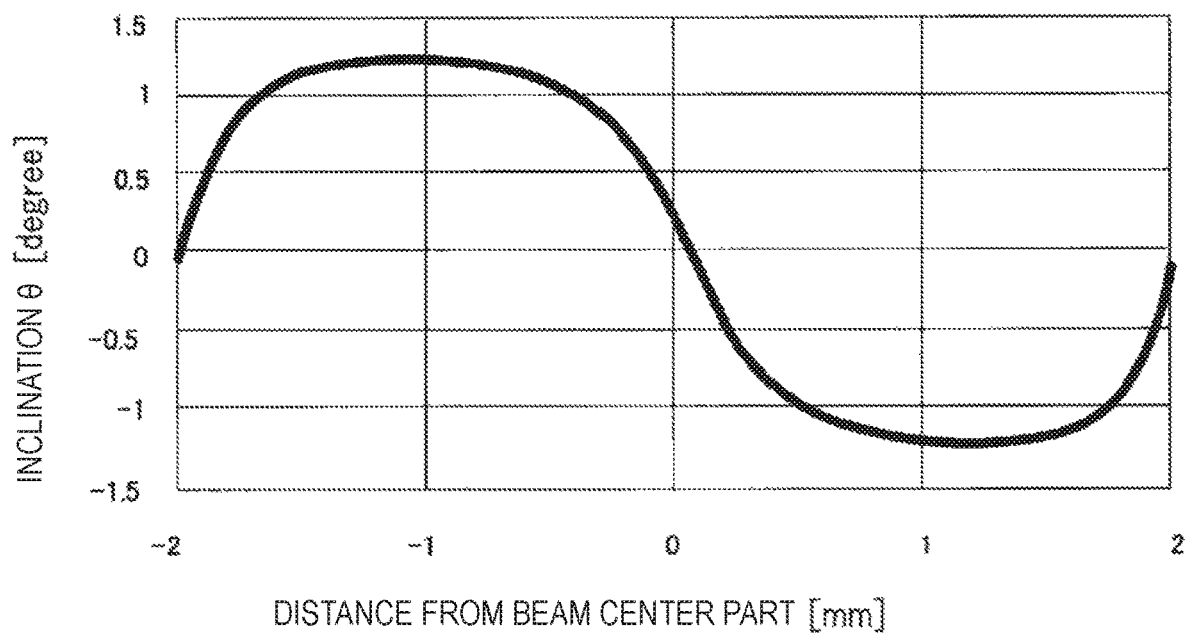
FIG. 17B is a graph illustrating one example of a relationship between the distance from the beam center part and an inclination of the doubly supported beam in the first wedge load distribution.

FIG. 17A is a graph illustrating one example of a relationship between a distance from the beam center part c1 in the first wedge load distribution and the deflection amount of the doubly supported beam 65. FIG. 17B is a graph illustrating one example of a relationship between the distance from the beam center part c1 in the first wedge load distribution and the inclination θ of the doubly supported beam 65.

In the first wedge load distribution, the load is not uniform at the contact portion with the measuring-target region of the doubly supported beam 65, and the load gradually becomes large as moving toward a positive direction from the beam center part c1. Therefore, as illustrated in FIG. 17A, the deflection amount y becomes maximum at a position slightly deviated in the positive direction from the beam center part c1 (here, a position of +0.05 from the beam center part c1).

Therefore, as illustrated in FIG. 17B, a position where the beam is parallel to the extending direction and the value of the inclination θ becomes zero is slightly deviated in the positive direction from the beam center part c1. In this case of the beam center part c1, the value of the inclination θ becomes about 0.14.

Figure 18A:
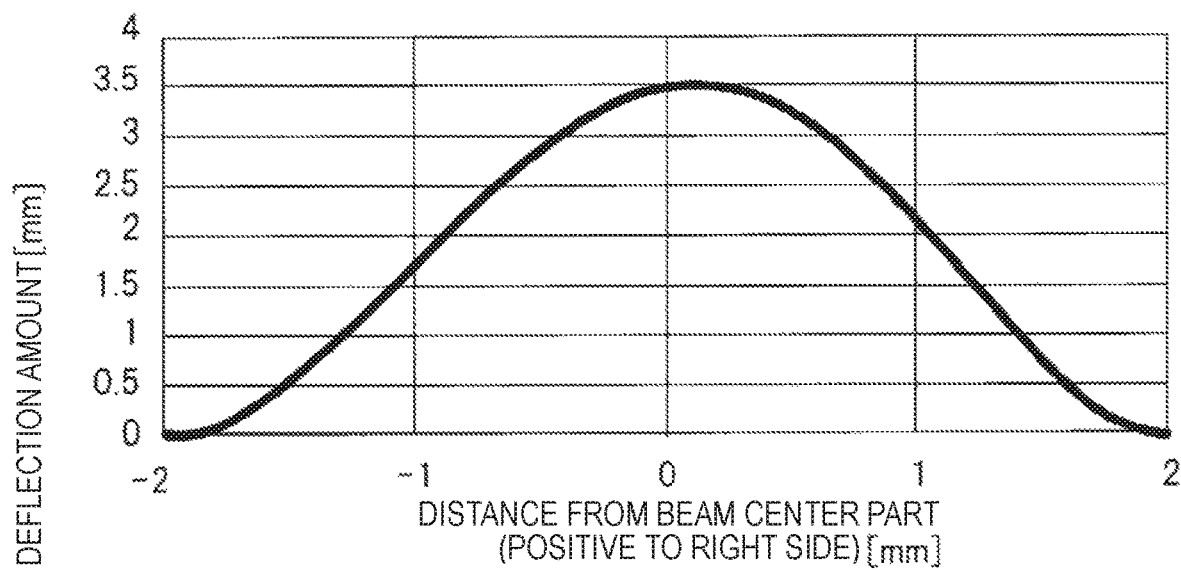
FIG. 18A is a graph illustrating one example of a relationship between a distance from a beam center part and a deflection amount of a doubly supported beam in second wedge load distribution.
Figure 18B:
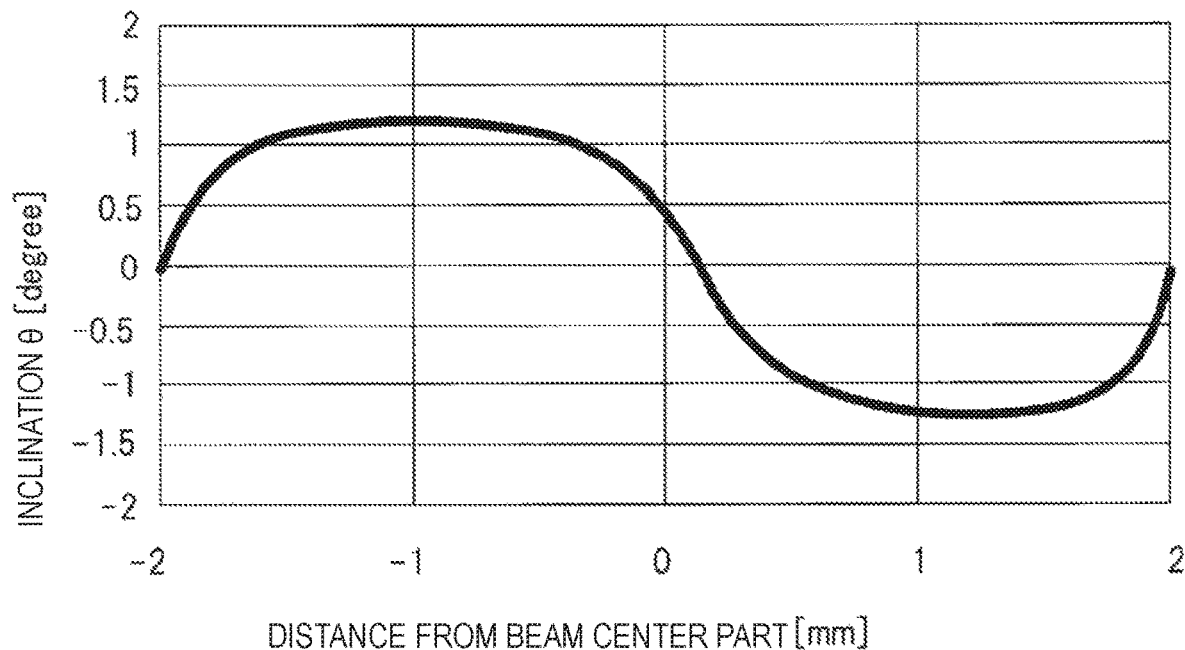
FIG. 18B is a graph illustrating one example of a relationship between the distance from the beam center part and an inclination of the doubly supported beam in the second wedge load distribution.

FIG. 18A is a graph illustrating one example of a relationship between a distance from the beam center part c1 in the second wedge load distribution and the deflection amount of the doubly supported beam 65. FIG. 18B is a graph illustrating one example of a relationship between the distance from the beam center part c1 in the second wedge load distribution and the inclination θ of the doubly supported beam 15.

In the second wedge load distribution, the load is not uniform at the contact portion with the measuring-target region of the doubly supported beam 65, and the load abruptly becomes larger than the first wedge load distribution as moving toward the positive direction from the beam center part c1. Therefore, as illustrated in FIG. 18A, the deflection amount y becomes maximum at a position deviated in the positive direction from the beam center part c1 (here, a position of +0.1 from the beam center part c1).

Therefore, as illustrated in FIG. 18B, a position where the beam is parallel to the extending direction and the value of the inclination θ becomes zero is deviated in the positive direction from the beam center part c1. The deviation in the positive direction is larger than the case of the first wedge load distribution. Further, in this case of the beam center part c1, the value of the inclination θ becomes about 0.40, and the inclination becomes larger than the case of the first wedge load distribution.

FIG. 19 is a schematic diagram illustrating the deflection amount y and the inclination θ of the doubly supported beam 65 at the beam center part 15 and the maximum displacement portion at each load pattern (each load distribution).

In FIG. 19, "A" indicates a load pattern A and indicates the equal load distribution. "B" indicates a load pattern B and indicates the first wedge load distribution. "C" indicates a load pattern C and indicates the second wedge load distribution.

As described above, according to the results of the second simulation, it can be understood that as the load applied to the contact portion with the measuring-target region of the doubly supported beam 65 approaches the equal load distribution, the deflection amount y at the beam center part c1 is small, and when the inclination θ approaches zero, the inclination θ is easy to be horizontal.

When the deflection amount y at the beam center part c1 becomes large and thus the inclination θ becomes large, the light receiving amounts of the scattered light L2 and the reflected light L3 by the first photodiode 30 and the second photodiode 40 are changed, whereby variations in the light receiving amounts thereof may occur. Therefore, the variation in the measurement result of the blood flow volume based upon the scatter light L2 occurs, such that there exists a possibility that reproducibility may deteriorate.

On the other hand, in the embodiment, the processor 310 derives the inclination θ of the protrusion 60 and the acrylic plate 50 in the extending direction dl of the protrusion 60 and the acrylic plate 50 at the beam center part c1, based upon the detection information by the second photodiode 40 and the strain gauge 42. According to the value of the inclination θ, the blood flow volume measuring device 100 can determine whether the load distribution is the equal load distribution or the wedge load distribution, and can determine a deviation degree of the load distribution, and the like.

Further, when the inclination θ is larger than a threshold value th, the display 330 displays warning information by the control of the processor 310. The threshold value th is, for example, zero. It is considered that the warning information is, for example, a message such as "please, press the middle".

Accordingly, the user can acquire information relating to a desirable method of pressing down the protrusion 60 and can intentionally bring the finger FG into contact with the center part of the protrusion 60. For example, it can be understood that even though the user intends to press down the protrusion 60 so as to achieve the equal load distribution, the wedge load distribution is achieved. Accordingly, the light receiving amount of the scattered light L2 by the first photodiode 30 is stabilized, and measurement accuracy of the blood flow volume measurement is improved, whereby the reproducibility of the blood flow volume measurement can be improved.

Further, in the embodiment, since the acrylic plate 50 contacts with the measuring-target region (for example, the finger FG) through the protrusion 60, the contact portion with the measuring-target region (for example, the finger FG) of the doubly supported beam 65 as the acrylic plate 50 becomes the contact portion with the protrusion 60.

Next, the reproducibility of the measurement result of the blood flow volume depending on the presence of the protrusion 60 of the blood flow volume measuring device 100 will be considered.

Here, even though the reproducibility of the measurement result of the blood flow volume is considered by using the tail of a rat, it is considered that the reproducibility using the human finger FG is also the same. Further, the reproducibility of the measurement result of the blood flow volume in the case of using the human finger FG will be described in a seventh embodiment which will be described later.

Figure 20A:
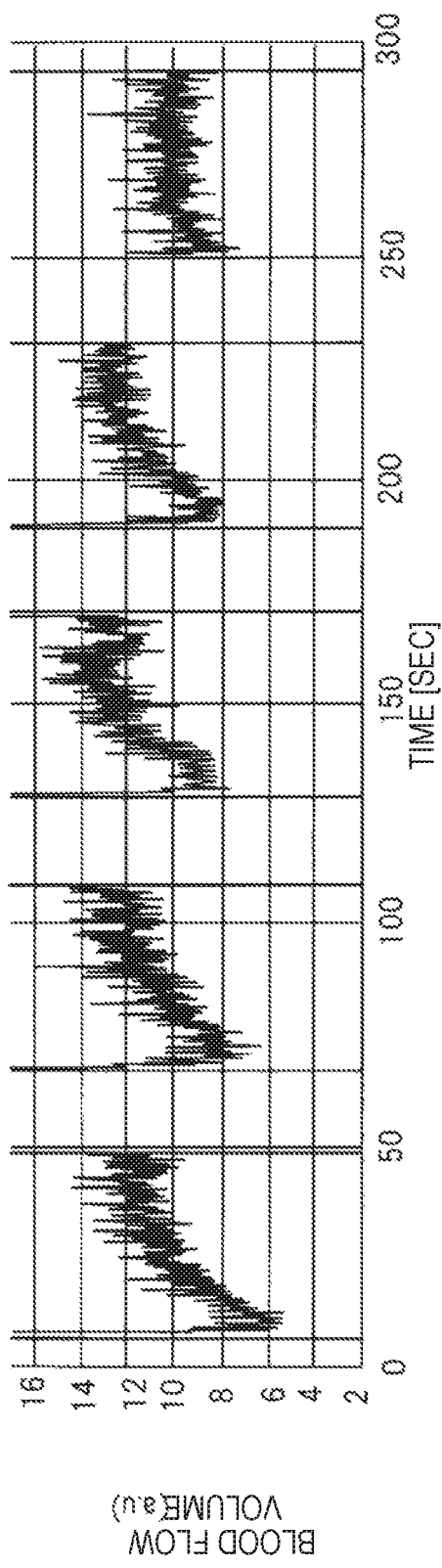
FIG. 20A is a graph illustrating a temporal change example of a blood flow volume of the tail of a rat measured by a blood flow volume measuring device not provided with a protrusion.

FIG. 20A is a graph illustrating a temporal change of the blood flow volume of the tail of a rat measured by the blood flow volume measuring device 100 not provided with the protrusion 60. A horizontal axis indicates time (sec), and a vertical axis indicates the blood flow volume (a.u.). FIG. 20A illustrates measurement results when 1% of anesthesia is administered to the tail of a rat and the load of 43 g is applied.

Figure 20B:
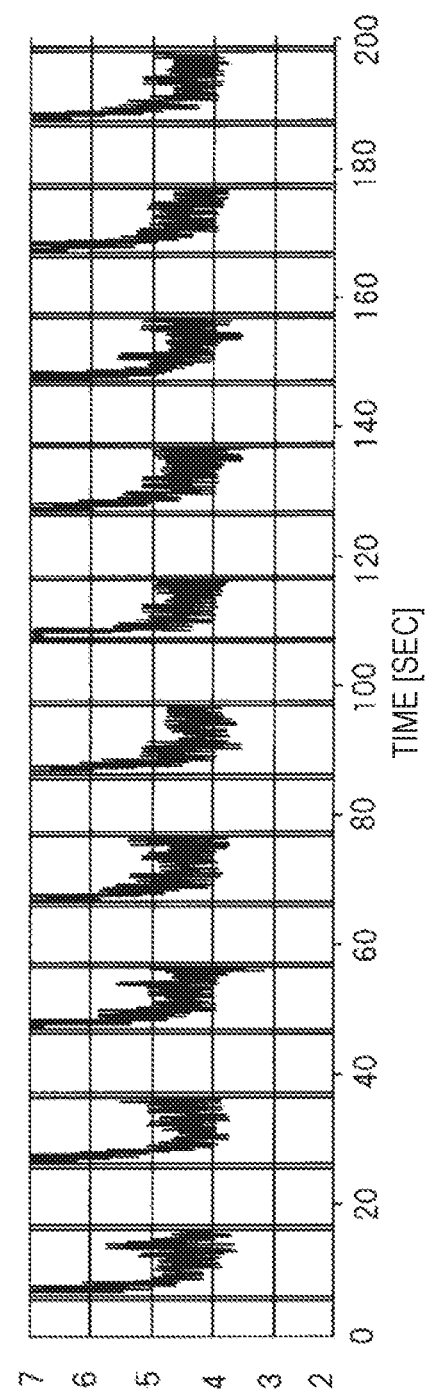
FIG. 20B is a graph illustrating a temporal change example of a blood flow volume of the tail of a rat measured by a blood flow volume measuring device provided with a protrusion.

FIG. 20B is a graph illustrating a temporal change of the blood flow volume of the tail of the rat measured by the blood flow volume measuring device 100 provided with the protrusion 60. A horizontal axis indicates time (sec), and a vertical axis indicates the blood flow volume (a.u.). FIG. 20B illustrates measurement results when 1% of the anesthesia is administered to the tail of the rat and the load of 43 g is applied. Here, as one example, a contact surface contacting with the tail of the rat, that is, the protrusion 60 in which a length of each side on a second surface Ax2 is 5 mm×4 mm and a height thereof is 2 mm is used.

In FIG. 20A, it can be understood that there exist the variations in the measurement results of the blood flow volume. It is considered that when the measurement of the blood flow volume of the tail of the rat is performed by using the blood flow volume measuring device 100, the variations in the measurement results may occur because a contact position, contact pressure, a contact area, and the like of the tail of the rat in contact with the blood flow volume sensor 200 (for example, the acrylic plate 50) are not constant. When the protrusion 60 is not provided, there exists no standard for the tail of the rat to contact with the blood flow volume sensor 200, and thus it is considered to be difficult for making the tail of the rat stably contact with the blood flow volume sensor 200.

On the other hand, in FIG. 20B, it can be understood that the variations in the measurement results of the blood flow volume are small, that is, the reproducibility is so good that the measurement is performed ten times. In FIG. 20B, it is considered that when the measurement of the blood flow volume of the tail of the rat is performed by using the blood flow volume measuring device 100, the contact position, the contact pressure, the contact area, and the like of the tail of the rat in contact with the blood flow volume sensor 200 (for example, the protrusion 60) are constant. It is considered that the protrusion 60 becomes the standard for the tail of the rat to contact with the blood flow volume sensor 200, thereby contributing to a stable contact with the blood flow volume sensor 200 and making it possible to obtain the blood flow volume measurement with good reproducibility.

Further, the height of the protrusion 60 is 2 mm as one example, and another value thereof may be used. When the finger FG contacts with the protrusion 60 during the blood flow volume measurement, it is desirable that the height of the protrusion 60 is such a height at which the finger FG does not contact with the acrylic plate 50 where the protrusion 60 is disposed.

Further, as one example, the length of each side on the second surface Ax2 of the protrusion 60 is 5 mm×4 mm, and another value thereof may be used. For example, when the length of each side on the second surface Ax2 of the protrusion 60 is 3 mm×3 mm, as described above, since the contact area contacting with the measuring-target region becomes small, it is possible to prevent a change in the deflection amount y of the acrylic plate 50 depending on the contact state of the measuring-target region. Accordingly, it is possible not only to increase the stability of the measurement results of the blood flow volume measurement, but also to improve the reproducibility.

Next, the blood flow volume before and after dehydration of the rat will be considered.

Here, as one example, in the same manner as the case of FIG. 20B, the protrusion 60, the length of which on the contact surface contacting with the tail of the rat is 5 mm×4 mm and the height of which thereon is 2 mm, is used.

Figure 21A:
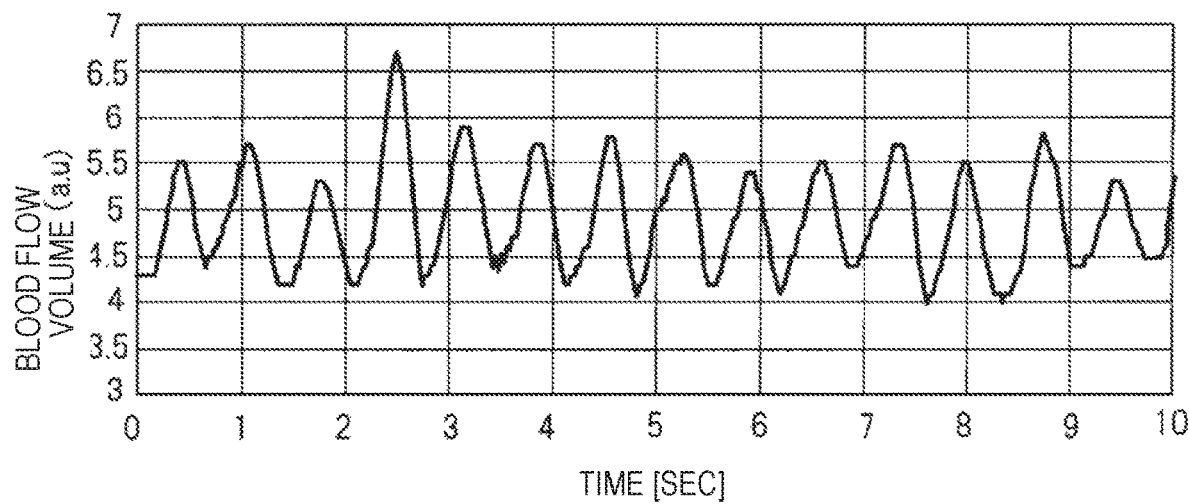
FIG. 21A is a graph illustrating a temporal change example of a blood flow volume of the tail of a healthy rat (a rat before dehydration)

FIG. 21A is a graph illustrating the temporal change of the blood flow volume of the tail of a healthy rat (a rat before dehydration). In FIG. 21A, the measurement result is illustrated when the protrusion 60 is provided in the blood flow volume sensor 200, a body temperature of the rat is 28.6° C., 1% of the anesthesia is administered, and the load of 43 g is applied.

Figure 21B:
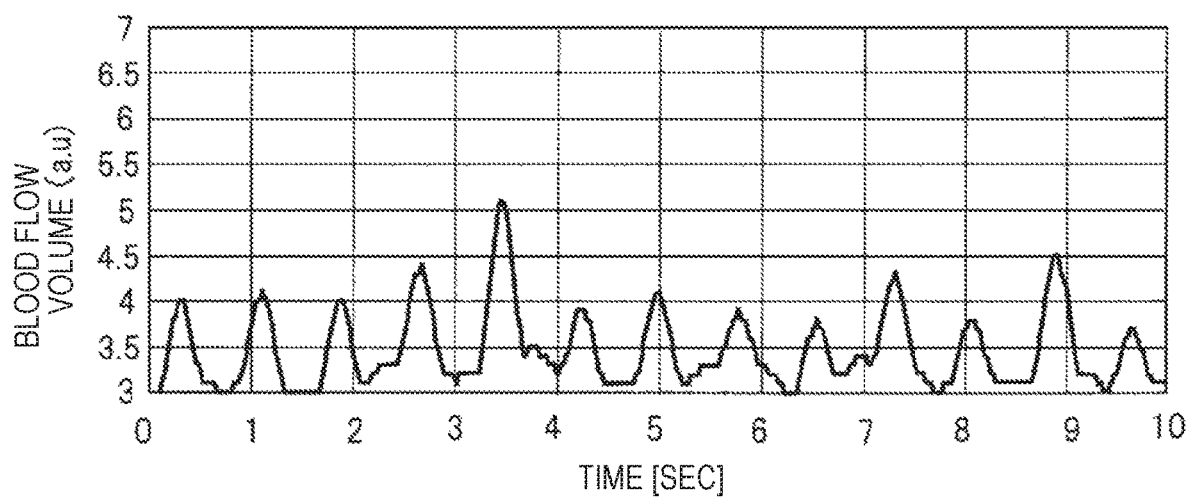
FIG. 21B is a graph illustrating a temporal change example of a blood flow volume of the tail of a rat in a dehydrated state.

FIG. 21B is a graph illustrating the temporal change of the blood flow volume of the tail of the rat in a dehydrated state. In FIG. 21B, the measurement result is illustrated when the protrusion 60 is provided in the blood flow volume sensor 200, the body temperature of the rat is 28.6° C., 1% of the anesthesia is administered, and the load of 43 g is applied.

In FIG. 21A, the blood flow volume of the tail of the rat is stable at a value of approximately 4.0 to 6.5. In FIG. 21B, the blood flow volume of the tail of the rat is stable at a value of approximately 3.0 to 5.0. Further, in the healthy rat corresponding to the FIG. 21A, an average blood flow volume is 4.98 (description of the unit is omitted. The same applies hereinafter), and average blood flow volume amplitude is 0.924, whereas in the dehydrated rat corresponding to FIG. 21B, an average blood flow volume is 3.54 and average blood flow volume amplitude is 0.642. Therefore, under the same rat (in other words, individual) and same measurement conditions, it is found out that the blood flow volume and the blood flow volume amplitude decrease as a state is changed from a healthy state to a dehydrated state. It is considered that the reasons why the blood flow volume decreases are that as the state is moved from the healthy state to the dehydrated state, the circulated blood volume decreases, and ratio of cellular components (for example, hematocrit) increases, for example, by reduction of water inside the body. It is considered that the reasons why the blood flow volume amplitude decreases are that as the state is moved from the healthy state to the dehydrated state, pulsation caused by the decrease in circulated blood volume deteriorates, and vasodilation of blood vessels caused by the dehydration deteriorates.

Therefore, according to the embodiment, the protrusion 60 is provided in the blood flow volume sensor 200, thereby performing the measurement of the blood flow volume with the good reproducibility, and as described above, since reliability of the measured blood flow volume is high, it is possible to estimate the dehydrated state with high accuracy according to the amount of the blood flow volume. Further, when the blood flow volume is high, for example, the hematocrit representing the ratio of the volume of the blood cells in the blood becomes higher than a normal range value (in other words, the blood becomes in the dehydrated state), or, for example, blood viscosity in the dehydrated state becomes higher than that in the healthy state. Therefore, it is considered that the identification of dehydration symptoms can be more easily made according to the amount of the blood flow volume.

Therefore, in the blood flow volume sensor 200 of the embodiment (for example, the processor 310 as one example of a dehydrated state identification unit), when the blood flow volume is larger than a preset value (for example, as illustrated in FIG. 21A, the state where the blood flow volume of the tail of the rat is stable at the value of approximately 4.0 to 6.5), it can be identified that the state is not the dehydration symptom. Here, the preset value is a threshold value for the blood flow volume sensor 200 to identify that the measuring-target region (for example, the rat tail or the finger FG of a person) is in the dehydrated state, and, for example, the preset value is defined during the operation of the processor 310.

On the other hand, in the blood flow volume sensor 200 of the embodiment (for example, the processor 310 as the example of the dehydrated state identification unit), when the blood flow volume is lower than the preset value (as illustrated in FIG. 21B, the state where the blood flow volume of the tail of the rat is stable at the value of approximately 3.0 to 5.0), it can be identified that the state is the dehydration symptom. In other words, it can be said that the blood flow volume sensor 200 of the embodiment is not only capable of simply measuring the blood flow volume of the blood flowing through the measuring-target region (for example, the finger FG of the person or the rat tail), but also capable of identifying the rat having the dehydration symptom with high accuracy.

Further, for example, as disclosed in the related WO 2015/199159 devised by some inventors of the present application, there is known a technique of detecting whether a subject suffers from the dehydration by making the subject raise a hand to lower the intravascular pressure of the subject. On the other hand, in the blood flow volume sensor 200 of the embodiment, the above-mentioned subject does not need to raise the hand and a preset contact pressure is applied to the protrusion 60, thereby relatively lowering the intravascular pressure of the subject. Therefore, it becomes possible to easily detect the dehydration with high accuracy, and configurations of the blood flow volume sensors of the respective embodiments, which will be hereinafter described, are the same.

Further, in the blood flow volume sensor 200 of the embodiment, the preset contact pressure is applied to the protrusion 60 instead of allowing the subject to raise the hand, thereby making it possible to detect scleroderma and alcohol intake as well as the dehydration, and the configurations of the blood flow volume sensor of the respective embodiments, which will be hereinafter described, are the same. In other words, in the blood flow volume sensor 200 of the embodiment in comparison with a method of the related art in which the blood flow volume is measured by raising the hand of the subject, according to the embodiment, the blood flow volume at the measuring-target region (for example the finger FG) of the subject is measured by applying the preset contact pressure to the protrusion 60, whereby it is possible to easily determine whether or not the subject suffers from symptoms such as the dehydration, the scleroderma, and the alcohol intake, that is, biological information (vital information) of the subject with high accuracy.

For example, even in the case of the same person, a standard of a contact place such as the protrusion 60 is absent in the blood flow volume sensor 200, it is difficult to contact with the blood flow volume sensor 200 at the same place and the same contact area. On the other hand, according to the blood flow volume measuring device 100 of the first embodiment, the protrusion 60 serves as the standard for the contact place by being provided with the protrusion 60, thereby making it possible to easily keep the contact area of the finger FG with respect to the blood flow volume measuring device 100 constant. Accordingly, the blood flow volume measuring device 100 makes it easy to keep the contact pressure per unit area constant, whereby it is possible not only to prevent the variation in the measured value of the blood flow volume measurement, but also to improve the reproducibility of the blood flow volume measurement.

Further, even in the case of the same contact area, when the load distribution applied to the protrusion 60 is not the equal load distribution, the warning information may be displayed by the display 330. Accordingly, the user can recognize what kind of the load distribution is in contact with the protrusion 60 and can press down the protrusion 60 so as to obtain the equal load distribution. Accordingly, since the contact state of the protrusion 60 can be corrected by the user, the blood flow volume measuring device 100 can prevent the variation in the measured value of the blood flow volume measurement, thereby improving the reproducibility of the blood flow volume measurement.

Further, the blood flow volume measuring device 100 may measure the blood pressure based upon the measurement result of the blood flow volume. Specifically, in the blood flow volume measuring device 100, the processor 310 may derive (compute) the average blood pressure of the finger FG based upon the pulse wave amplitude of the blood flow volume, which is derived as described above, with the high reproducibility and the low variation in the measured value. Further, the processor 310 may derive (compute) the highest blood pressure based upon the blood flow volume as a result of multiplying the pulse wave amplitude of the blood flow volume at the time when the average blood pressure is obtained by a preset first coefficient (for example, 0.5). Further, the processor 310 may derive (compute) the lowest blood pressure based upon the blood flow volume as a result of multiplying the pulse wave amplitude of the blood flow volume at the time when the average blood pressure is obtained by a preset second coefficient (for example, 0.4). A well-known method (for example, refer to WO 2015/199159 A) may be used as a method for deriving average blood pressure, maximum blood pressure, and maximum pressure based upon the pulse wave amplitude of the blood flow volume.

Accordingly, the blood flow volume measuring device 100 can derive the average blood pressure of the finger FG based upon the pulse wave amplitude of the blood flow volume with the high reproducibility. Therefore, the blood flow volume measuring device 100 can prevent the variation in the measured value of the blood pressure measurement even with respect to the blood pressure, thereby improving the reproducibility of the blood pressure measurement.

Modified Examples

Figure 22:
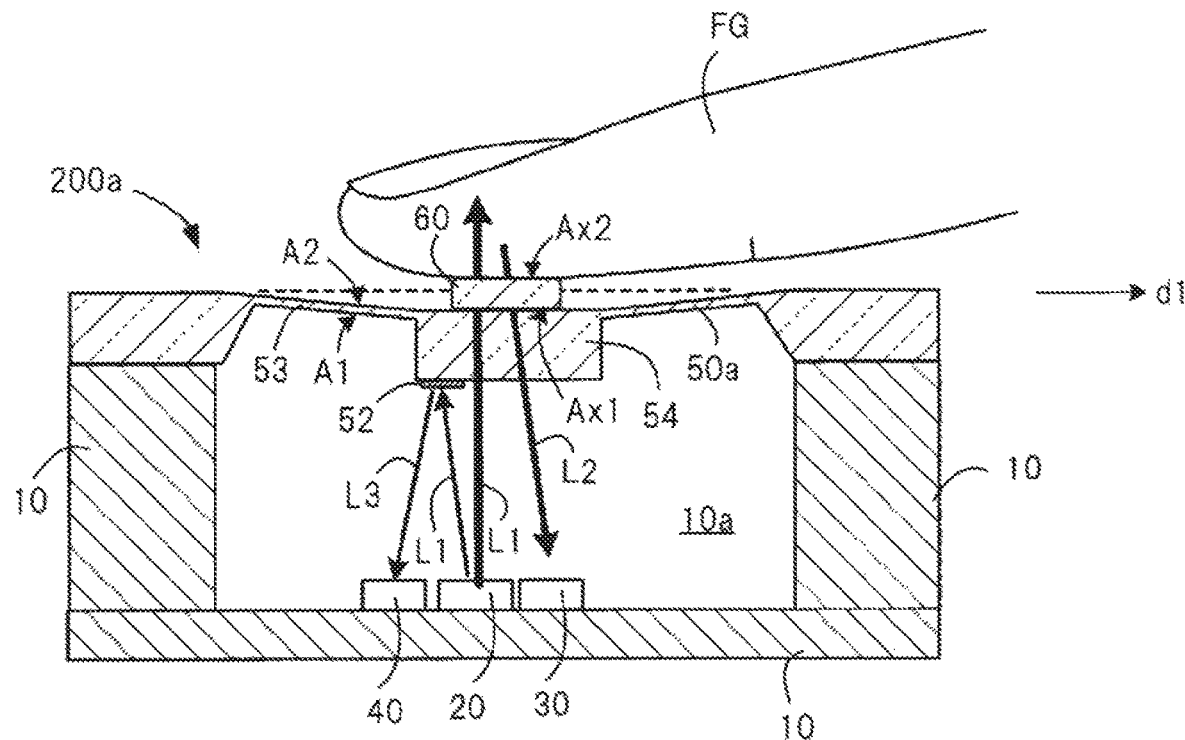
FIG. 22 is a cross-sectional view illustrating a configuration example of a blood flow volume sensor according to a modified example.

In a modified example, the configuration of the acrylic plate of the blood flow volume sensor is different in comparison with the configuration of FIGS. 3 and 4. FIG. 22 is a cross-sectional view illustrating the blood flow volume sensor according to the modified example. A blood flow volume sensor 200a in FIG. 22 is the same as the blood flow volume sensor 200 in FIGS. 3 and 4, however, an acrylic plate 50a is provided therein instead of the acrylic plate 50. In FIG. 22, with respect to the same components as those of FIG. 3, the same reference sings are denoted thereto, and descriptions thereof will be omitted or will be simply described.

In the acrylic plate 50a, a thick part 54 is formed in a preset range including a position of the acrylic plate 50a at which the protrusion 60 is disposed. In the acrylic plate 50a, a thin part 53 is formed in a range other than the thick part 54 of the acrylic plate 50a. The thick part 54 and the thin part 53 may be formed of different materials. Therefore, the thick part 54 includes a position facing the protrusion 60. The thin part 53 includes a position which does not face the protrusion 60.

In the preset range (that is, the preset range including the position of the acrylic plate 50a at which the protrusion 60 is disposed), a portion through which the emitted light L1 and the scattered light L2 pass is included. Further, the preset range means a range in which when the finger FG contacts with the protrusion 60, stress equal to or greater than a preset value is applied thereto, and deformation of the acrylic plate 50a is easy to occur. For example, the preset range becomes such a thickness at which the finger FG contacts with the protrusion 60 and does not contact with the thin part 53 when the finger FG pressurizes and contacts with the protrusion 60. For example, when measuring the blood flow volume by using the finger FG, it is assumed that the thickness of the thick part is less than 2 mm and the thickness of the thin part is 0.3 mm, however, the thicknesses thereof can be changed according to the measuring-target region and a size of the blood flow volume sensor 200. Further, for example, when the measuring-target region is the finger FG, a length of the thick part 54 is about 4.5 mm in diameter.

In the thick part 54, since rigidity thereof is high, the thick part 54 of the acrylic plate 50 is hardly deflected and is hardly inclined even though the load is applied to the protrusion 60 by the finger FG.

Here, a parameter "I" of Equation 1 representing a computation example of the deflection amount (y) of the doubly supported beam 65 is represented by Equation 10 in detail as follows:

Equation 10

$$I = \frac{bh^3}{12} \quad \text{(Equation 10)}$$

Accordingly, "I" represented in Equation 10 is proportional to "h", that is, the cube of a height (thickness) of the doubly supported beam 65. Therefore, according to Equation 1, it can be said that even though the height of the doubly supported beam 65 is slightly increased, the deflection amount of the doubly supported beam 65 is greatly reduced.

As described above, according to the blood flow volume measuring device 100 provided with the blood flow volume sensor 200a according to the modified example, the thick part 54 is formed at a place through which the emitted light L1 and the scattered light L2 pass in the acrylic plate 50a. Therefore, since the acrylic plate 50a becomes difficult to be deflected, the blood flow volume measuring device 100 can prevent an influence on the inclination of the acrylic plate 50a caused by the load distribution such as the equal load distribution, the wedge load distribution, and the like. Accordingly, the blood flow volume measuring device 100 stabilizes the light receiving amount by the scattered light L2 by the first photodiode 30 and improves the measurement accuracy of the blood flow volume measurement using the Doppler shift, thereby improving the reproducibility of the blood flow volume measurement.

Second Embodiment

In a second embodiment, the blood flow volume sensor in the blood flow volume measuring device is different from that of the first embodiment. In the first embodiment, the blood flow volume sensor provided with the protrusion 60 is described, however, in the second embodiment, the blood flow volume sensor not provided with the protrusion 60 will be described. Further, the blood flow volume sensor is a micro machine, a size of which is smaller than that of the first embodiment.

Figure 23:
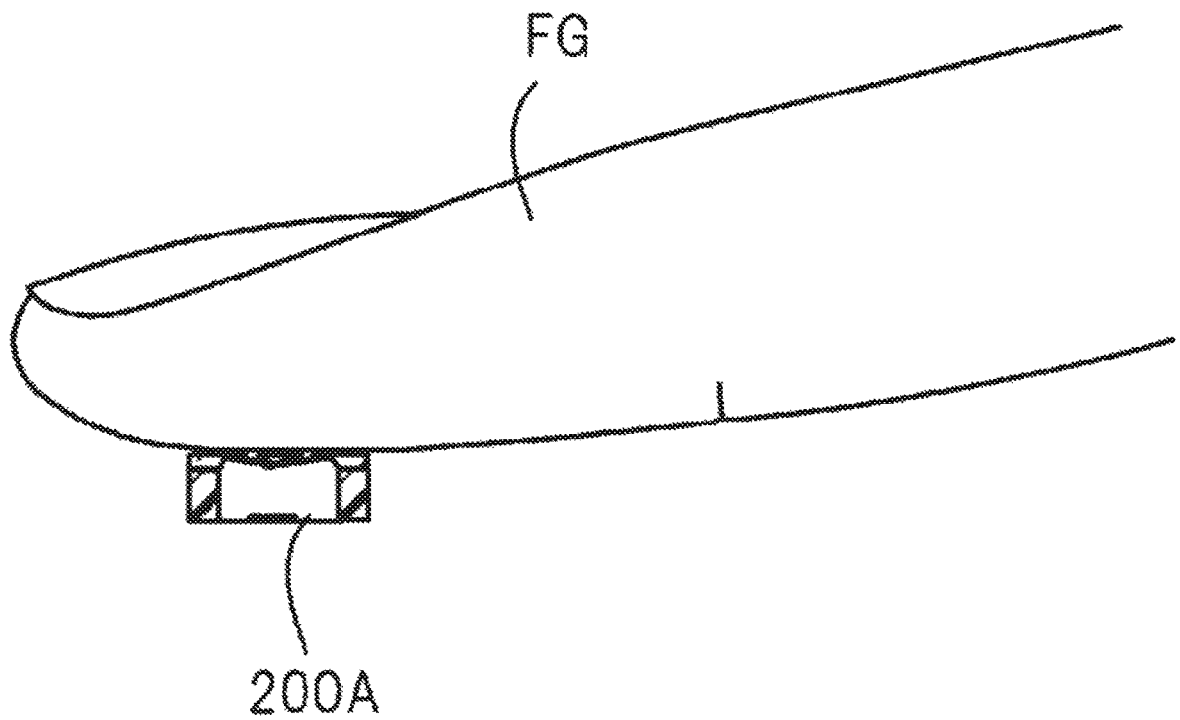
FIG. 23 is a cross-sectional view illustrating a configuration example of the blood flow volume sensor according to the second embodiment.

FIG. 23 is a cross-sectional view illustrating a configuration example of a blood flow volume sensor 200A according to the second embodiment. In FIG. 23, with respect to the same components as those of the first embodiment, the same reference sings are denoted thereto, and descriptions thereof will be omitted or will be simply described.

The blood flow volume sensor 200A is not illustrated in the drawing and is provided with the base 10, the VCSEL 20, the first photodiode 30, the second photodiode 40, and the acrylic plate 50. However, the blood flow volume sensor 200A is not provided with the protrusion on the second surface A2 of the acrylic plate 50 facing the finger FG.

The acrylic plate 50 contacts with the finger FG during the blood flow volume measurement, however, the whole surface of the second surface A2 can contact with the finger FG. That is, the contact area of the contact surface of the finger FG in contact with the acrylic plate 50 becomes equal to the area of the second surface A2 of the acrylic plate 50, such that the contact area becomes constant. Accordingly, the second surface A2 of the acrylic plate 50 is easily pressed by the equal load distribution, thereby improving the accuracy of blood flow volume measurement. In the embodiment, the acrylic plate 50 is one example of the contact member.

Further, even in the embodiment, the strain gauge 42 may be provided instead of the second photodiode 40.

As described above, according to the blood flow volume measuring device provided with the blood flow volume sensor 200A of the embodiment, even though the protrusion 60 is omitted, the finger FG can contact with the whole surface of the acrylic plate 50, thereby keeping the contact area constant. Therefore, the blood flow volume measuring device can be easily contacted with the equal load distribution and the accuracy of the blood flow volume measurement can be improved, whereby the reproducibility of the blood flow volume measurement becomes high.

Third Embodiment

In a third embodiment, the blood flow volume sensor in the blood flow volume measuring device is different from those of the first and second embodiments. In the third embodiment, the blood flow volume sensor is not provided with the protrusion in the same manner as that of the second embodiment. Further, in the third embodiment, the strain gauge is embedded in the acrylic plate, which is different from the second embodiment.

Figure 24:
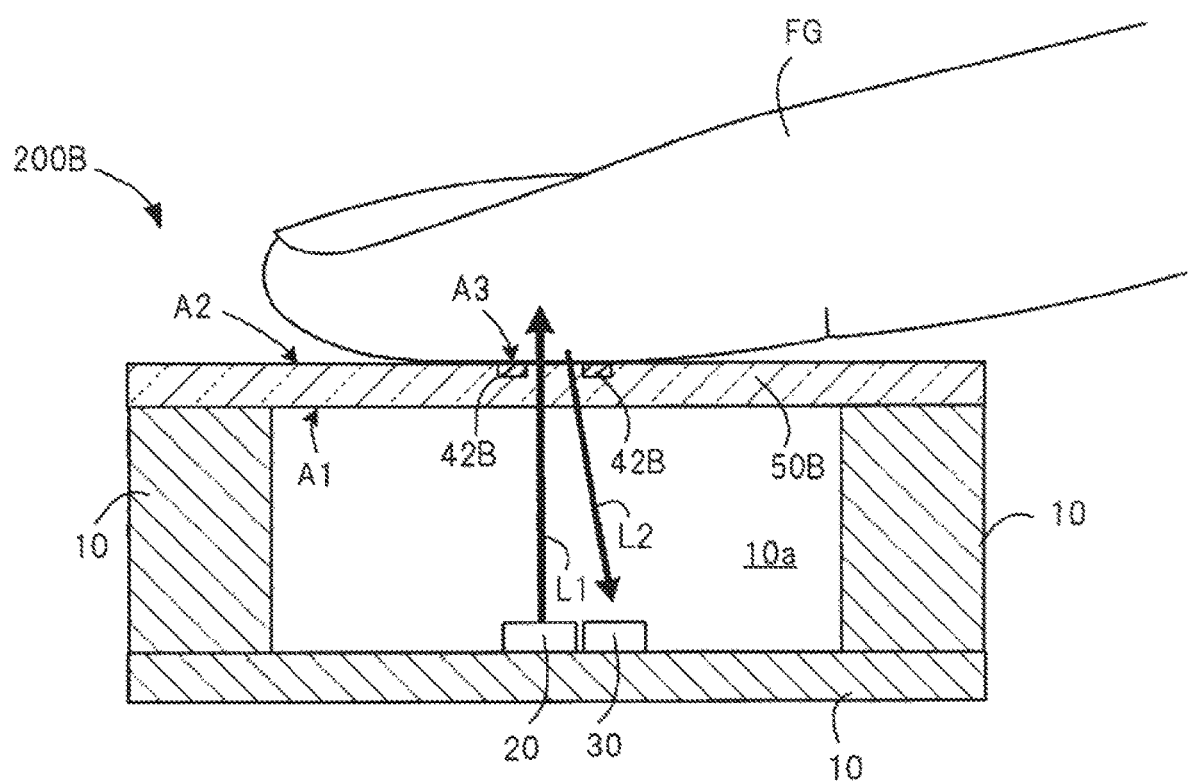
FIG. 24 is a cross-sectional view illustrating a configuration example of a blood flow volume sensor according to a third embodiment.

FIG. 24 is a cross-sectional view illustrating a configuration example of a blood flow volume sensor 200B according to the third embodiment. In FIG. 24, with respect to the same components as those of the first or second embodiment, the same reference sings are denoted thereto, and descriptions thereof will be omitted or will be simply described.

The blood flow volume sensor 200B is provided with the base 10, the VCSEL 20, the first photodiode 30, a strain gauge 42B, and an acrylic plate 50B. However, the blood flow volume sensor 200B is not provided with the protrusion on the second surface A2 of the acrylic plate 50B facing the finger FG.

Further, the strain gauge 42B is embedded in the acrylic plate 50B. A surface A3 which faces the finger FG of the strain gauge 42B is positioned on the same plane as the second surface A2 of the acrylic plate 50B.

That is, in the blood flow volume sensor 200B, the minute strain gauge 42B is embedded in the acrylic plate 50B, and the strain gauge 42B detects the deflection and the inclination caused by the finger FG. The contact pressure per unit area is derived from the deflection and the inclination. The strain gauge 42B contacts with the finger FG when measuring the blood flow volume, and the whole surface of the surface A3 can contact with the finger FG. That is, the contact area of the contact surface of the finger FG in contact with the acrylic plate 50B becomes equal to the area of the surface A3 of the strain gauge 42B, thereby keeping the contact area constant. As a result, the surface A3 of the strain gauge 42B becomes easily pressed by the equal load distribution, thereby improving the accuracy of the blood flow volume measurement.

Inside the strain gauge 42B, a metal resistor is included as a microbeam. The microbeam is displaced by the contact pressure, and the deflection is detected, that is, the pressure is measured. That is, the contact area of the finger FG with respect to the strain gauge 42B as a pressure sensor that determines the pressure is constant and a size of the strain gauge 42B is smaller than that of the finger FG.

As described above, according to the blood flow volume measuring device provided with the blood flow volume sensor 200B of the embodiment, even though the protrusion 60 is omitted and further, it is difficult for the finger FG to contact with the whole surface of the acrylic plate 50B, the contact area of the finger FG with respect to the strain gauge 42B relating to the pressure measurement can be kept constant. Therefore, the blood flow volume measuring device can be easily contacted with the equal load distribution and the accuracy of the blood flow volume measurement can be improved, whereby the reproducibility of the blood flow volume measurement becomes high.

Fourth Embodiment

In the first to third embodiments, the measurement of the blood flow volume of the living body such as the finger FG, the rat, and the like is described, however, in the fourth embodiment, measurement of a flow volume of a measuring object other than the blood flow volume of the living body will be described.

Figure 25A:
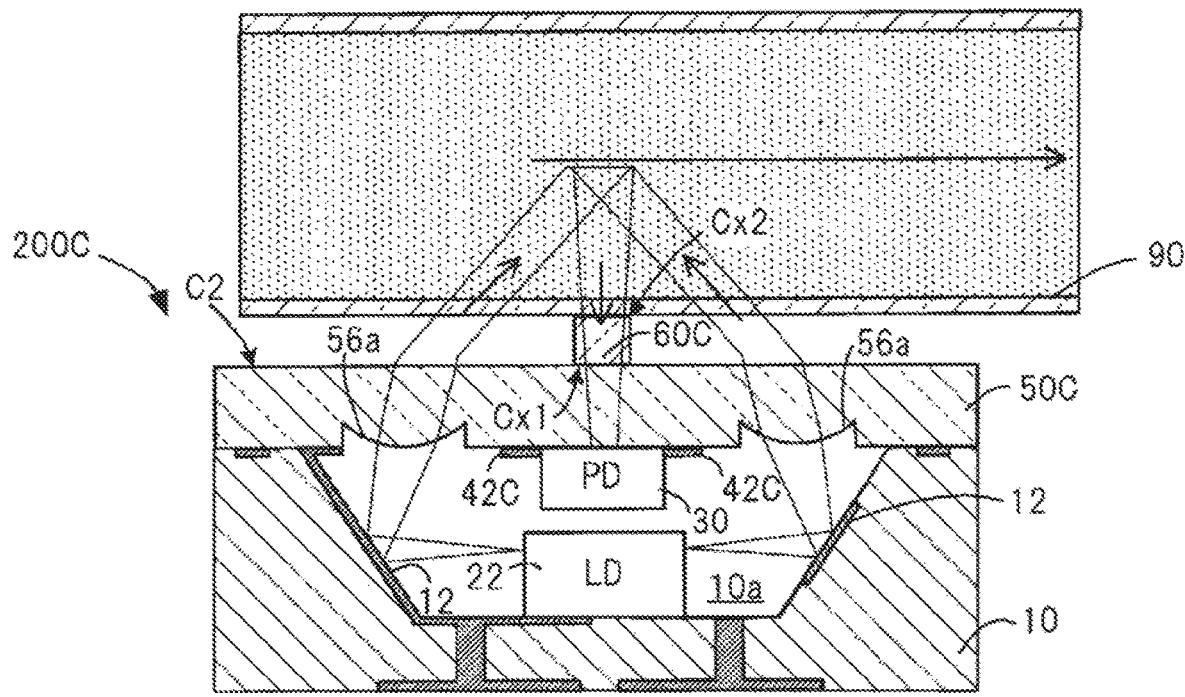
FIG. 25A is a cross-sectional side view illustrating a configuration example of a flow volume sensor according to a fourth embodiment.
Figure 25B:
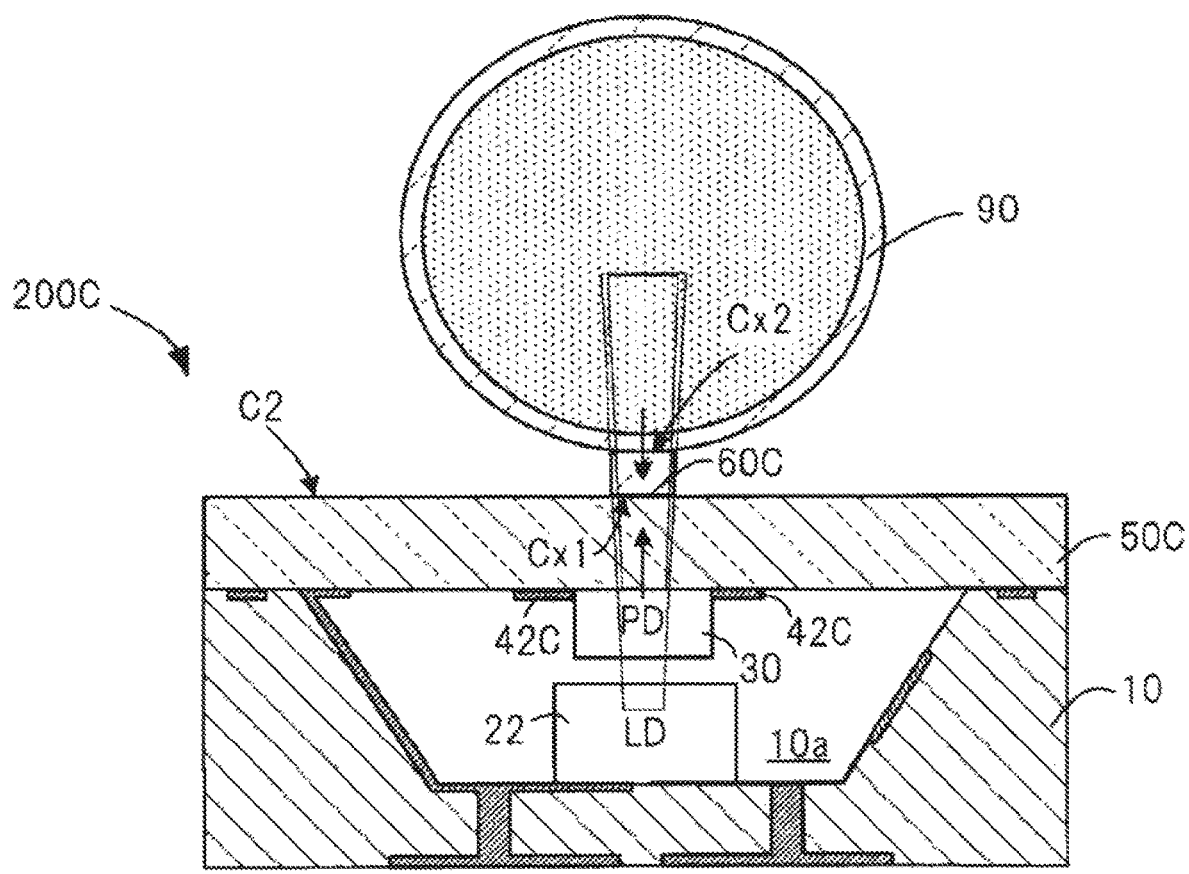
FIG. 25B is a cross-sectional front view illustrating the configuration example of the flow volume sensor according to the fourth embodiment.

FIG. 25A is a cross-sectional side view illustrating a flow volume sensor 200C according to the fourth embodiment. FIG. 25B is a cross-sectional front view illustrating the flow volume sensor 200C according to the fourth embodiment. In the flow volume sensor 200C, with respect to the same components as those of the first to third embodiments, the same reference sings are denoted thereto, and descriptions thereof will be omitted or will be simply described.

In FIGS. 25A and 25B, as one example, it is assumed that a flow volume of blood flowing through a tube 90 as a measuring-target region is measured. For example, the tube 90 is excellent in flexibility. The tube 90 is one example of a tubular member.

The flow volume sensor 200C is provided with the base 10, a laser diode (LD) 22, the first photodiode (PD) 30, a strain gauge 42C, a glass plate 50C, and a protrusion 60C.

The laser diode 22 emits the emitted light L1. The emitted light L1 is reflected by the mirror 12 disposed on the base 10, penetrates the glass plate 50C, and is directed toward the tube 90 as the measuring-target region. Further, instead of the laser diode 22, the VCSEL 20 described above may be provided.

The first photodiode 30 receives the scattered light L2 in which the emitted light L1 is scattered or reflected in the tube 90 through the protrusion 60 and the glass plate 50C.

That is, in FIGS. 25A and 25B, the emitted light L1 from the laser diode 22 is reflected by the mirror 12 of the base 10, penetrates the glass plate 50C, and is directed toward blood inside the tube 90. The glass plate 50C includes a protruding curved surface 56a and allows the emitted light L1 of the laser diode 22 to be concentrated at a preset position inside the tube 90 by the protruding curved surface 56a. The scattered light L2 scattered or reflected at the preset position penetrates the protrusion 60C and the glass plate 50C and is received by the first photodiode 30.

The glass plate 50C has transparency with respect to the wavelengths of the emitted light L1 and the scattered light L2. That is, the glass plate 50C is disposed between the laser diode 22 and the finger FG, and between the first photodiode 30 and the finger FG, and allows the emitted light L1 and the scattered light L2 to pass therethrough. Further, in FIGS. 25A and 25B, in the glass plate 50C, both ends of the glass plate 50C are fixed to the upper ends of the base 10. Therefore, the glass plate 50C becomes the doubly supported beam (the beam fixed at the both ends). The glass plate 50C is one example of a translucent member. Further, instead of the glass plate 50C, the aforementioned acrylic plate 50 may be provided.

The protrusion 60C is disposed on a second surface C2 facing the tube 90 of the glass plate 50C. The protrusion 60C is, for example, disposed at a center part of the glass plate 50C. The protrusion 60C has translucency with respect to the wavelengths of the emitted light L1 and the scattered light L2. That is, the protrusion 60C is disposed between the laser diode 22 and the tube 90, and between the first photodiode 30 and the tube 90, and allows the emitted light L1 and the scattered light L2 to pass therethrough.

The protrusion 60C is, for example, formed of glass. In this case, the material is the same as that of the glass plate 50C, a refractive index difference at a boundary between the glass plate 50C and the protrusion 60C becomes small, whereby light transmission properties become high. Additionally, the protrusion 60C may be formed of a member having translucency other than the acrylic material.

Further, a first surface Cx1 of the protrusion 60C in contact with the glass plate 50C is smaller than the second surface C2 of the glass plate 50C (an area is small). Further, the tube 90 can contact with a whole surface of a second surface Cx2 of the protrusion 60 in contact with the tube 90. That is, the second surface Cx2 of the protrusion 60 is smaller than the tube 90 in contact with the protrusion 60C. Therefore, when the protrusion 60C is pressed by the tube 90, the whole surface of the second surface Cx2 of the protrusion 60C receives the tube 90, whereby the contact pressure per unit area of the protrusion 60C becomes easy to be constant.

Thus, according to the flow volume measuring device provided with the flow volume sensor 200C of the embodiment, the tube 90 contacts with the protrusion 60C, such that the load applied to the protrusion is easy to be the equal load distribution, thereby making it possible to keep a deformation amount of the tube 90 constant. Therefore, the flow volume measuring device is not only capable of improving stability of the flow volume measurement, but also capable of improving the reproducibility of the measurement result.

Fifth Embodiment

In a fifth embodiment, a supporting member, which is provided around the protrusion, for supporting the finger FG will be described.

FIG. 26 is a cross-sectional view illustrating a configuration example of a blood flow volume sensor 200D according to the fifth embodiment. In FIG. 26, with respect to the same components as those of the first to fourth embodiments, the same reference sings are denoted thereto, and descriptions thereof will be omitted or will be simply described.

The blood flow volume sensor 200D is provided with the base 10, the VCSEL 20, the first photodiode 30, the second photodiode 40, an acrylic plate 50D, the mirror 52, a protrusion 60D, and a supporting member 62.

In FIG. 26, the acrylic plate 50D and the protrusion 60D are integrally formed, but may be formed as separate bodies. The protrusion 60D is formed of a translucent member such as the acrylic material, and the like in the same manner as those of the above-mentioned embodiments.

For example, the supporting member 62 is formed to include iron and SUS and may not have translucency. The supporting member 62 includes an opening 62a at the center part. An area of the opening 62a is larger than an area of the second surface Ax2 of the protrusion 60D. Since the opening 62a does not cover the second surface Ax2 of the protrusion 60D, the protrusion 60D is in a state of being exposed to the outside. Further, a surface of the opening 62a is positioned closer to a side of the acrylic plate 50D than the second surface of the protrusion 60D in a state where the protrusion 60D is not pressed down by the finger FG. That is, a part of the protrusion 60D protrudes from the opening 62a of the supporting member 62. Therefore, the finger FG can first contact with the protrusion 60D before contacting with the supporting member 62, and when the protrusion 60D is pressed down, the finger FG is supported by the supporting member 62, whereby the finger FG can be prevented from contacting with the acrylic plate 50D.

When the load is applied to the protrusion 60D by the finger FG, the supporting member 62 supports the finger FG apart from the acrylic plate 50D so as to prevent the finger FG from contacting with a portion other than the protrusion 60D in the acrylic plate 50D. Therefore, the supporting member 62 can prevent the finger FG from contacting with the acrylic plate 50D.

Accordingly, according to the blood flow volume measuring device provided with the blood flow volume sensor 200A of the embodiment, the blood flow volume sensor 200D is provided with the supporting member 62, thereby preventing the finger FG from contacting with the acrylic plate 50D.

Further, in the embodiment, the deflection amount, the inclination, the contact pressure, the load distribution, and the like are derived according to the light receiving amount by the scattered light L2. Additionally, a pressing force of the finger FG is received by being restricted at a preset position (a position facing the protrusion 60D) by the supporting member 62 in the acrylic plate 50D, and the pressing force thereof is prevented from being applied to other positions. Therefore, the deflection amount of the acrylic plate 50D is stabilized, and the light receiving amount of the scattered light L2 by the first photodiode 30 is stabilized. Accordingly, the blood flow volume measuring device is not only capable of improving the measurement accuracy of the blood flow volume measurement using the Doppler shift, but also capable of improving the reproducibility of the blood flow volume measurement.

Sixth Embodiment

In the first to fifth embodiments, as the doubly supported beam 65, the acrylic plate and the glass plate, both ends (two points) of which are fixed to the base 10, are described. In a sixth embodiment, the acrylic plate and the glass plate, in which all or a portion of peripheral ends (for example, four points at end parts of line segments orthogonal to each other) are fixed to the base 10, will be described.

Figure 27A:
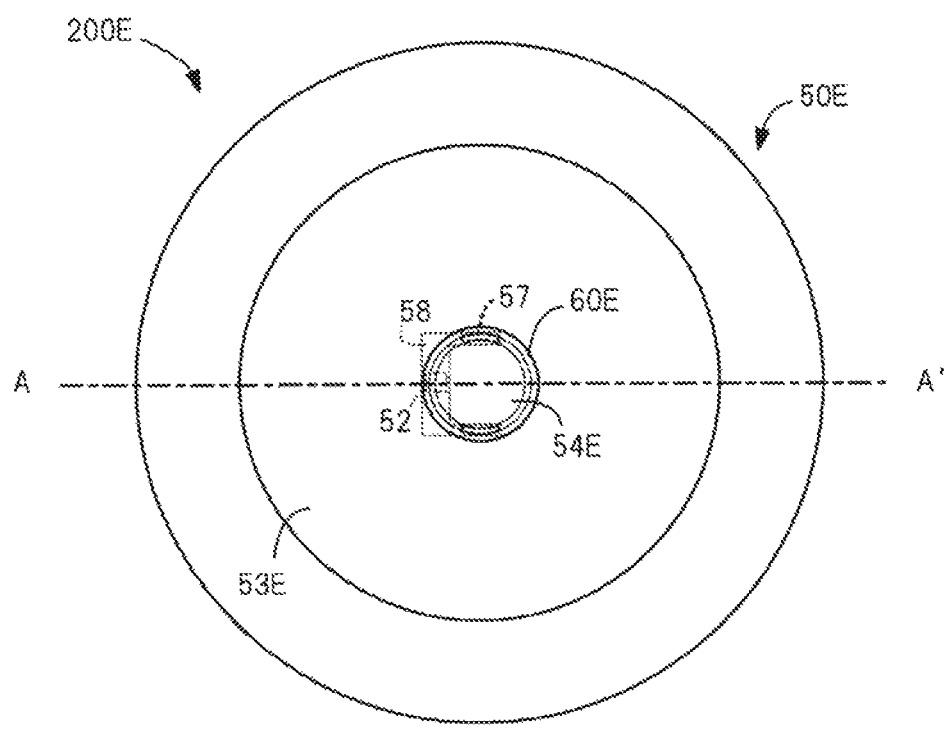
FIG. 27A is a plan view illustrating a first configuration example of a blood flow volume sensor according to a sixth embodiment.
Figure 27B:
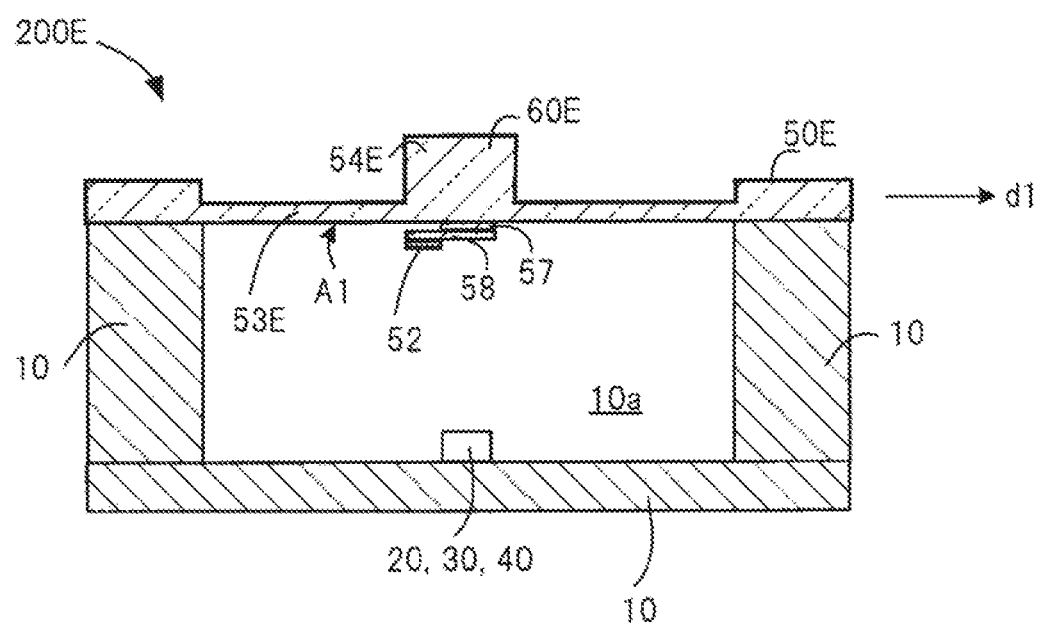
FIG. 27B is a cross-sectional view taken along the line A-A' of FIG. 27A.
Figure 28A:
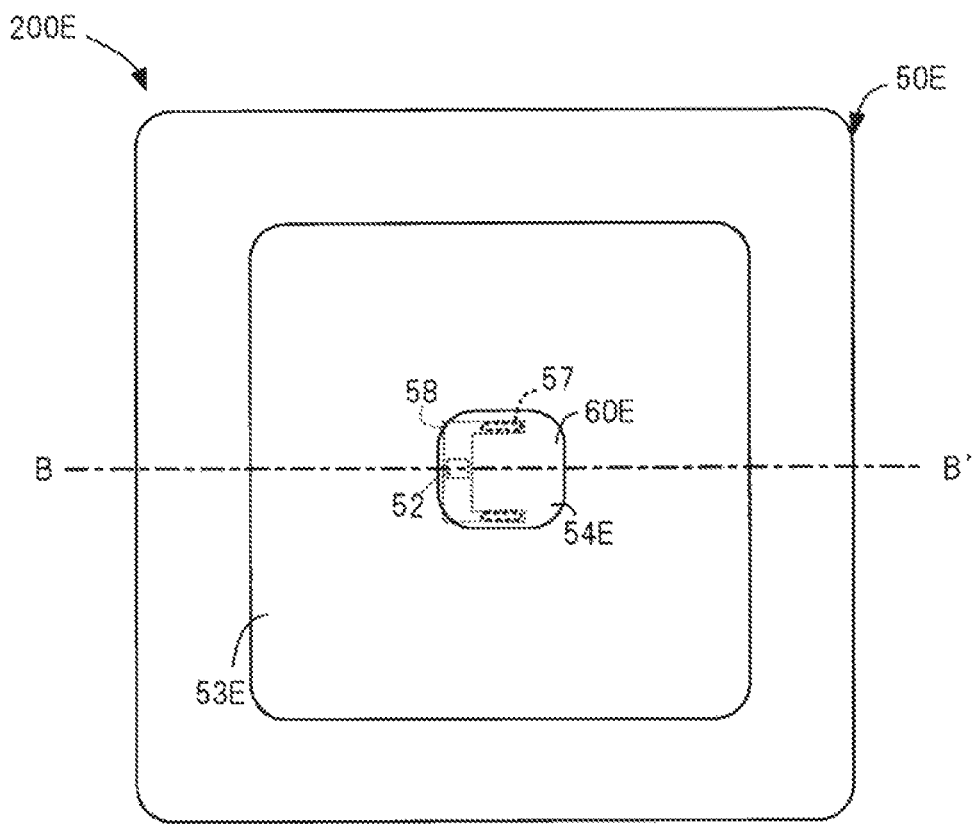
FIG. 28A is a plan view illustrating a second configuration example of the blood flow volume sensor according to the sixth embodiment.
Figure 28B:
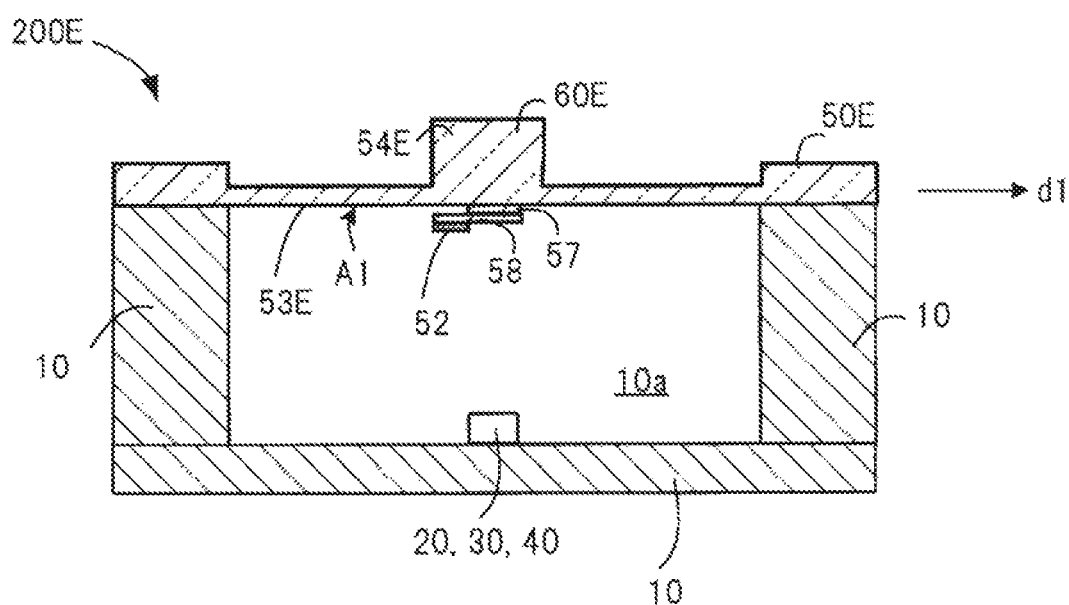
FIG. 28B is a cross-sectional view taken along the line B-B' of FIG. 28A.

FIG. 27A is a plan view illustrating a first configuration example of a blood flow volume sensor 200E. FIG. 27B is a cross-sectional view taken along the line A-A' of FIG. 27A. FIG. 28A is a plan view illustrating a second configuration example of the blood flow volume sensor 200E. FIG. 28B is a cross-sectional view taken along the line B-B' of FIG. 28A. In FIGS. 27A and 27B and FIGS. 28A and 28B, with respect to the same components as those of the first to fifth embodiments, the same reference sings are denoted thereto, and descriptions thereof will be omitted or will be simply described.

In FIGS. 27A and 27B, and FIGS. 28A and 28B, the blood flow volume sensor 200E is provided with the base 10, the VCSEL 20, the first photodiode 30, the second photodiode 40, an acrylic plate 50E, the mirror 52, a supporting protrusion 57, and a mirror holding member 58, and a protrusion E.

In FIGS. 27A and 27B, and FIGS. 28A and 28B, the acrylic plate 50E and the protrusion 60E are integrally formed, but may be formed as separate bodies. The protrusion 60E is formed of the translucent member such as the acrylic material, and the like in the same manner as those of the above-mentioned embodiments.

In FIGS. 27A and 27B, the acrylic plate 50E is formed in a circular shape in the plan view, but may be formed in other shapes (for example, an elliptical shape). In FIGS. 28A and 28B, the acrylic plate 50E is formed in an approximately square shape in the plan view, but may be formed in other shapes (for example, an approximately rectangular shape and an approximately polygonal shape other than an approximately quadrangular shape).

In FIGS. 27A and 27B, and FIGS. 28A and 28B, in the acrylic plate 50E, the peripheral ends of the acrylic plate 50E (also including a portion of the circumferential ends) are fixed to upper ends of the base 10. Therefore, the acrylic plate 50E becomes a peripheral end fixed beam.

In the acrylic plate 50E, a position of the acrylic plate 50E where the protrusion 60E is disposed becomes a thick part 54E. The acrylic plate 50E becomes a thin part 53E in a range other than positions fixed to the thick part 54E and the base 10. The thick part 54 and the thin part 53 may be formed of different materials. The thickness (height) of the thick part 54E is, for example, 2.3 mm. The thickness (height) of the thin part 53E is, for example, 0.3 mm.

The thick part 54E of the acrylic plate 50E includes a portion through which the emitted light L1 and the scattered light L2 pass. Since the thick part 54E has high rigidity, even though the load is applied to the protrusion 60E by the finger FG, the thick part 54E of the acrylic plate 50E is hardly deflected and is hardly inclined.

One or more (for example, two) supporting protrusions 57 are provided on the first surface A1 facing the VCSEL 20 of the acrylic plate 50E. The supporting protrusion 57 has translucency with respect to the wavelengths of the emitted light L1 and the scattered light L2 in the same manner as that of the acrylic plate 50E. The supporting protrusion 57 supports the mirror holding member 58.

The supporting protrusion 57 has translucency with respect to the wavelengths of the emitted light L1 and the scattered light L2 in the same manner as that of the acrylic plate 50E. In FIGS. 27A and 28A, the mirror holding member 58 includes a U-typed shape. Further, the mirror holding member 58 may have other shapes other than the U-typed shape. The mirror holding member 58 is provided (for example, stuck to) with the mirror 52 on a surface facing the VCSEL 20.

The mirror 52 reflects part of the emitted light L1 emitted from the VCSEL 20 and the reflected part of the emitted light L1 becomes reflected light L3. Further, in FIGS. 27A and 28A, the mirror 52 is stuck to a center part of the U-typed shape of the mirror holding member 58, but may be stuck to another position of the mirror holding member 58.

Accordingly, the mirror 52 is stuck to a lower part of the thick part 54E of the acrylic plate 50E. At the position of mirror 52, rigidity is high, and the acrylic plate 50E is hardly deflected, thereby being hard to be inclined. Thus, the light receiving amount of the reflected light L3 which is reflected by the mirror 52 and received by the second photodiode 40 is stabilized. Accordingly, the blood flow volume measuring device can stabilize the measurement accuracy of the displacement, the deflection amount, the inclination, the pressure, and the like of the acrylic plate 50E using the reflected light L3.

On the other hand, in the thin part 53E adjacent to the thick part 54E, since the acrylic plate 50E is easy to be deflected, the deflection amount becomes large. Therefore, the blood flow volume measuring device can surely obtain the displacement of the acrylic plate 50E based upon the light receiving amount of the reflected light L3, and can easily derive a blood flow volume signal.

Next, a case in which the periphery of the circular-shaped acrylic plate 50E is fixed to the base 10 in a plan view will be considered.

Figures 29A, 29B:
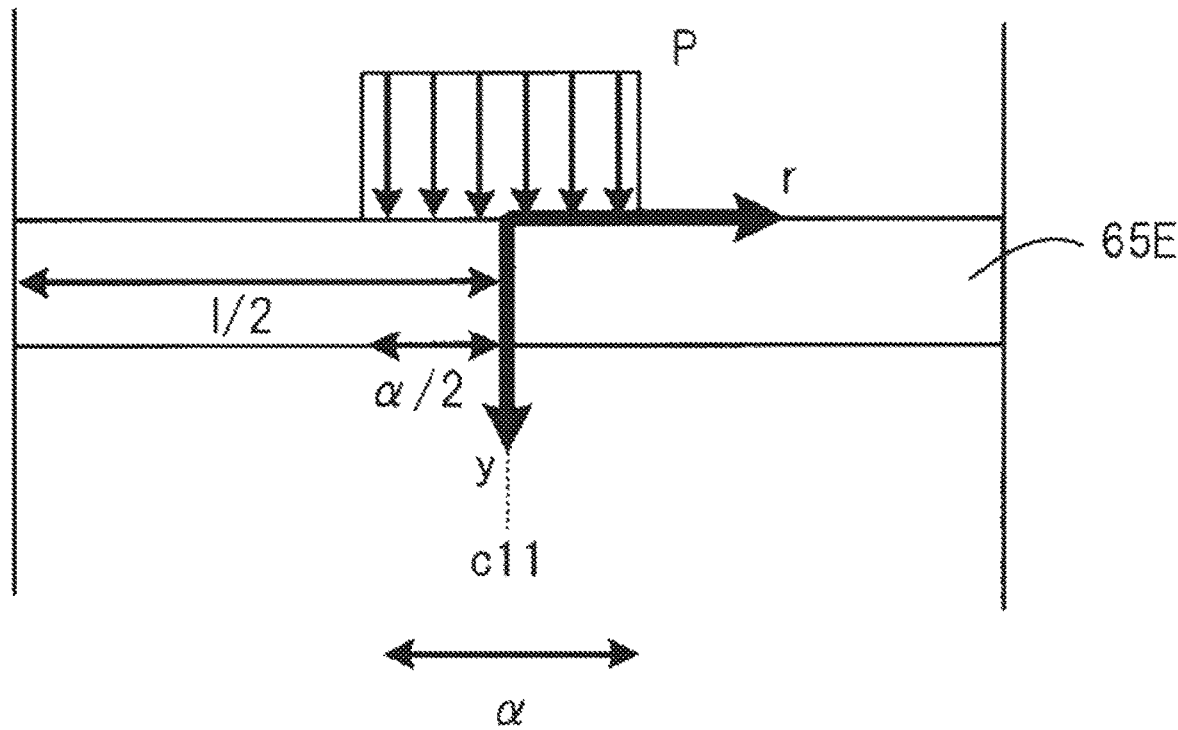
FIG. 29A is a schematic diagram illustrating one example of equal load distribution in a beam 65.
FIG. 29B is a schematic diagram illustrating one example of a parameter used for a third simulation.

FIG. 29A is a schematic diagram illustrating one example of the equal load distribution in a beam 65E (simply, referred to a beam). In the embodiment, each parameter is represented as follows. The beam 65E is the peripheral end fixed beam, the peripheral ends of which are fixed.

"q": load per unit area to the beam 65E

"α": length of the contact portion (diameter of the contract portion) where the beam 65E and the measuring-target region contact with each other "l": length of a diameter of the beam 65E "h": height of the beam 65E "E": Young's modulus of the beam 65E "D": deflection strength of the beam 65E A position in a diameter direction of the beam 65E (a distance from abase point (a center part of the beam 65E in FIG. 29A)) is represented by a variable r. A position in a height direction of the beam 65E (a distance from a base point (a top end of the beam 65E in FIG. 29A)) is represented as a variable y. The variable y corresponds to the deflection amount of the beam 65E.

The deflection amount (y) of the beam 65E is, for example, represented by Equation 11 as follows:

Equation 11

$$y = \frac{q\alpha^2}{16D}\left\{(\alpha^2 + 2r^2)\ln\frac{\alpha}{l} - \frac{3}{4}\alpha^2 + l^2 - \frac{r^2\alpha^2}{2l^2} + \frac{r^4}{4\alpha^2}\right\}$$ (Equation A relationship between a load q per unit area and a total load P is represented by Equation 12 as follows:

Equation 12

$$P = q \times \pi \times (\alpha/2)^2$$ (Equation

Therefore, a change rate (dy/dr) of the deflection amount (y) at each position in the diameter direction of the beam 65E is represented, for example, by Equation 13. The change rate corresponds to a change in the deflection amount with respect to a 25 minute change of the position in the diameter direction of the beam 65E.

Equation 13

$$\frac{dy}{dx} = \frac{q\alpha^4}{16D}\left\{4r\ln\frac{\alpha}{r} - \frac{r\alpha^2}{l^2} + \frac{r^3}{\alpha^2}\right\}$$ (Equation Further, the deflection amount of the beam 65E is proportional to the fourth power of the contact portion length a as shown in Equation 11. Therefore, when the contact portion length a changes and the contact area changes, the deflection amount of the beam 65E largely changes.

Further, in the embodiment, an example of the equation in the case of the wedge load distribution in the beam 65E is omitted, however, even in the case of the wedge load distribution, the deflection amount of the beam 65E is proportional to the fourth power of the contact portion length a. Therefore, when the contact portion length a changes and the contact area changes, the deflection amount of the beam 65E largely changes.

FIG. 29B is a schematic diagram illustrating one example of a parameter used for a third simulation. In the third simulation, the deflection y and the inclination θ of the beam 65E in the equal load distribution will be considered.

Figure 30A:
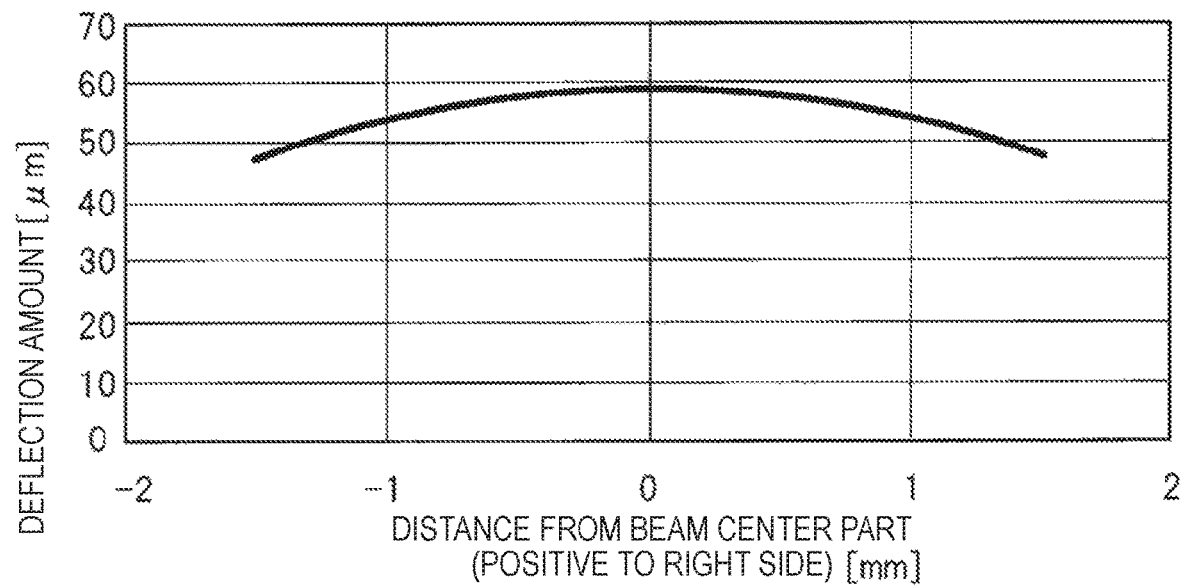
FIG. 30A is a graph illustrating one example of a relationship between a distance from a beam center part and a deflection amount of a beam in equal load distribution.
Figure 30B:
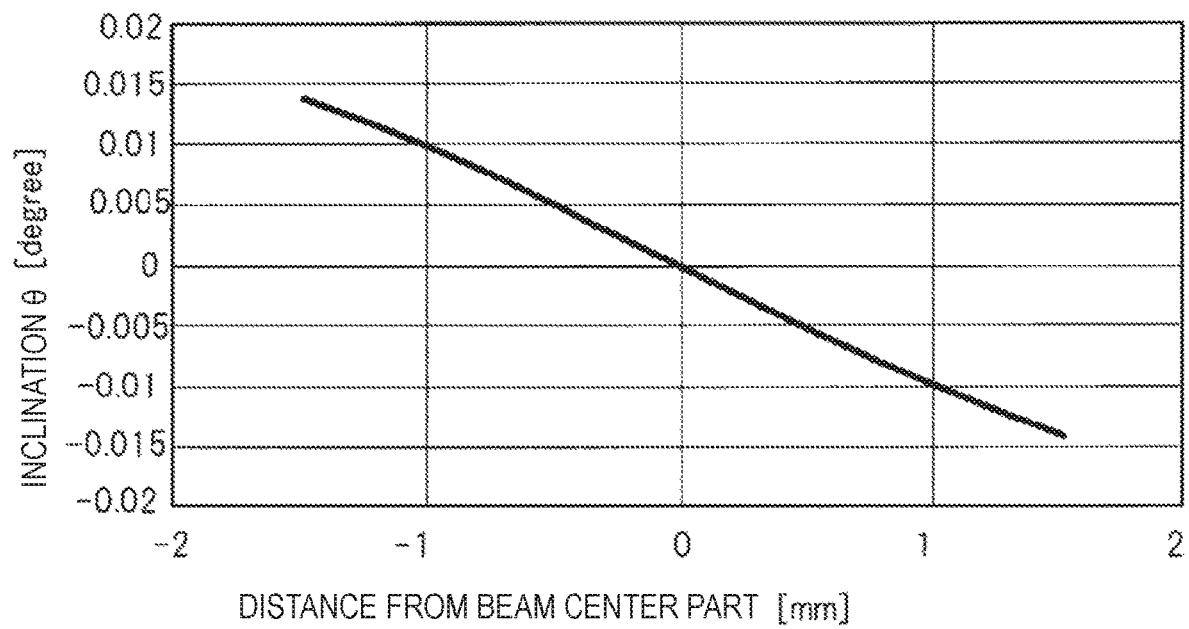
FIG. 30B is a graph illustrating one example of a relationship between the distance from the beam center part and an inclination of the beam in the equal load distribution.

FIG. 30A is a graph illustrating one example of a relationship between a distance from a beam center part c11 and a deflection amount of the beam E in the equal load distribution. FIG. 30B is a graph illustrating one example of a relationship between the distance from the beam center part c11 and the inclination θ of the beam 65E in the equal load distribution.

In the equal load distribution, the load is uniform at the contact part of the beam 65E with the measuring-target region. Therefore, as illustrated in FIG. 30A, the deflection amount y at the beam center part c11 becomes maximum. Therefore, as illustrated in FIG. 30B, at the beam center part c11 where the deflection amount y is maximum, it becomes parallel (for example, horizontal) to the extending direction of the beam 65E when no load is applied to the beam 65E, whereby a value of the inclination θ becomes zero.

Further, the value of the inclination θ corresponds to the value of the change rate (dy/dr) of the deflection amount (y) at each position in the diameter direction (a left-and-right direction in FIG. 29A) of the beam 65E.

Accordingly, the blood flow volume measuring device provided with the blood flow volume sensor 200E of the embodiment is provided with the acrylic plate 50E as the beam 65E (the peripheral end fixed beam). Even in this case, the contact area of the finger FG with respect to the blood flow volume measuring device can be easily kept constant by pressing down the protrusion 60E by the finger FG. Therefore, the blood flow volume measuring device 100 can easily keep the contact pressure per unit area constant and can prevent the variation in the measured value of the blood flow volume measurement, thereby improving the reproducibility of the blood flow volume measurement.

Additionally, in the embodiment, details of the deflection amount y and the inclination θ of the beam 65E in the wedge load distribution are omitted, however, in the same manner as that of the first embodiment, the deflection amount y becomes maximum at the position deviated from the beam center part c11, and the value of the inclination θ becomes zero or the value thereof becomes large at the beam center part c11. That is, as the load applied to the contact portion of the beam 65E with the measuring-target region approaches the equal load distribution, the deflection amount y at the beam center part c11 is small, and the inclination θ approaches 0 and easily becomes horizontal.

Further, the processor 310 may derive the inclination θ of the protrusion 60E and the acrylic plate 50E in the extending direction dl of the protrusion 60E and the acrylic plate 50E at the beam center part c1, based upon the detection information obtained by the second photodiode 40, and the like. The blood flow volume measuring device can determine whether to be the equal load distribution or the wedge load distribution, and determine a degree of the deviation of the load distribution from the value of the inclination θ.

Additionally, in the same manner as that of the first embodiment, when the inclination θ is larger than the threshold value th (for example, value is "0"), the display 330 may display the warning information such as "please, press the middle", and the like under the control of the processor 310.

Further, in the embodiment, the deflection amount y, the inclination θ, and the like of the beam 65E when the periphery of the circular-shaped acrylic plate 50E in the top plan view is fixed to the base 10 will be considered, and the same result is obtained even in the case of the acrylic plate 50E having an approximately square shape in the top plan view.

Seventh Embodiment

In the embodiment, measurement of the blood flow volume using an electrostatic capacitance sensor will be described.

Figure 31A:
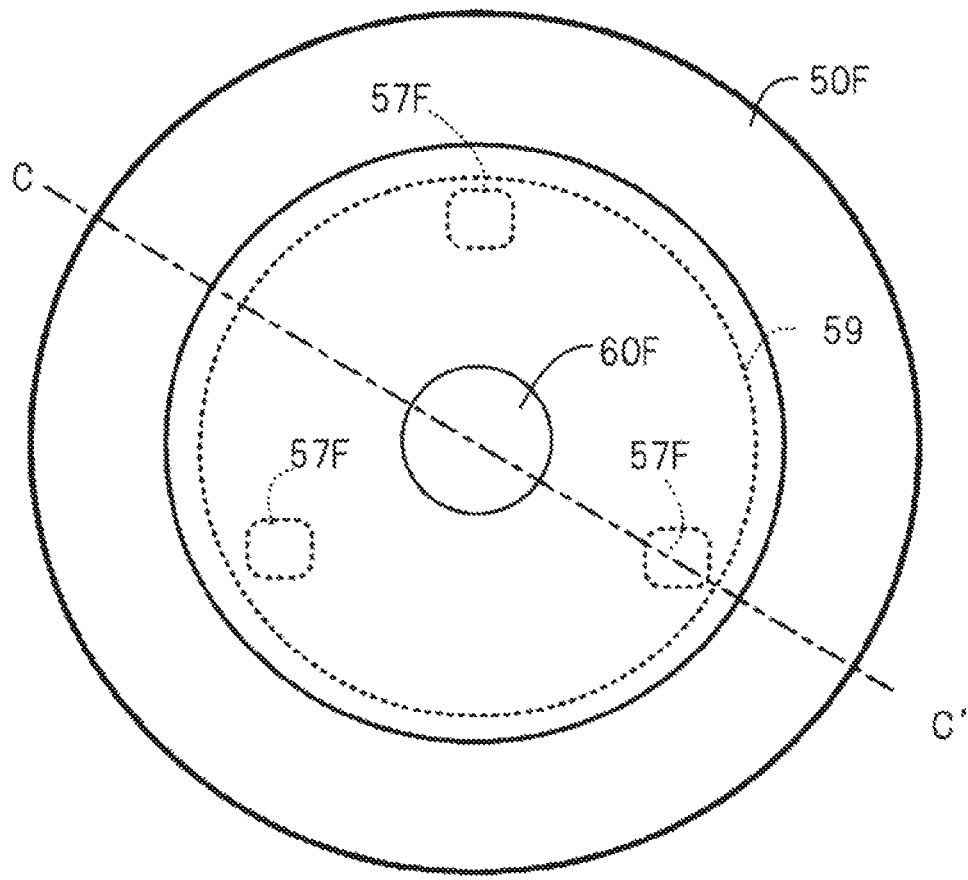
FIG. 31A is a plan view illustrating a configuration example of a blood flow volume sensor according to a seventh embodiment.
Figure 31B:
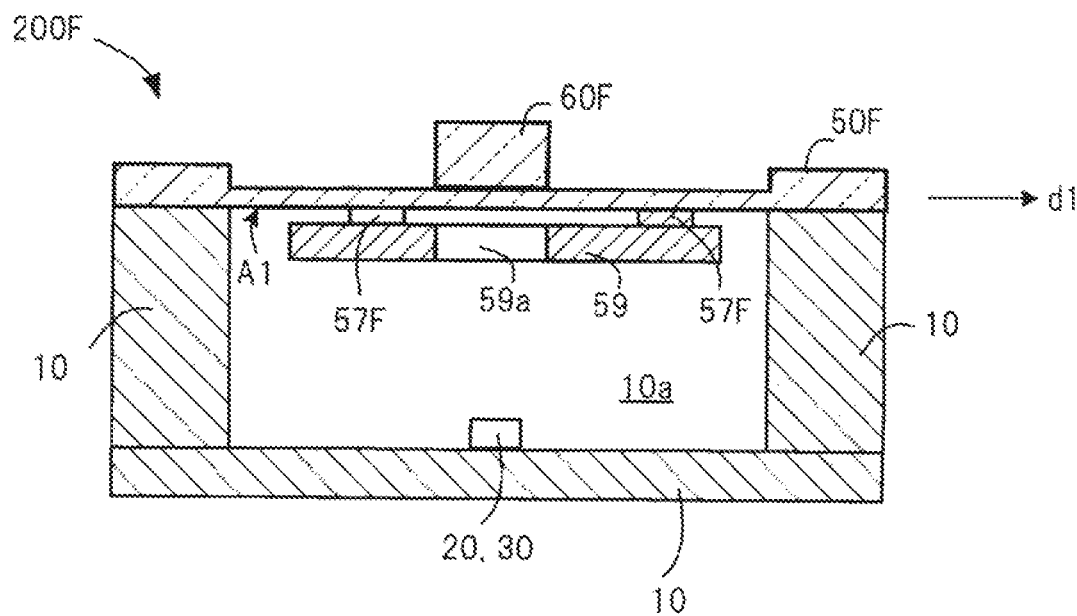
FIG. 31B is a cross-sectional view taken along the line C-C' of FIG. 31A.

FIG. 31A is a plan view illustrating a first configuration example of a blood flow volume sensor 200F. FIG. 31B is a cross-sectional view taken along the line C-C' of FIG. 31A. In FIGS. 31A and 31B, with respect to the same components as those of the first to sixth embodiments, the same reference sings are denoted thereto, and descriptions thereof will be omitted or will be simply described.

The blood flow volume sensor 200F is provided with the base 10, the VCSEL 20, the first photodiode 30, an acrylic plate 50F, a supporting protrusion 57F, an electrostatic capacitance sensor 59, and a protrusion 60F. That is, instead of the second photodiode 40, the electrostatic capacitance sensor 59 is provided.

In FIGS. 31A and 31B, the acrylic plate 50F and the protrusion 60F are separately formed, but may be integrally formed. The acrylic plate 50F and the protrusion 60F are formed of the translucent member such as the acrylic material, and the like in the same manner as those of the above-mentioned embodiments.

In FIGS. 31A and 31B, the acrylic plate 50F is formed in a circular shape in the plan view, but may be formed in other shapes (for example, an elliptical shape, an approximately square shape, an approximately polygonal shape other than an approximately square shape). Further, the acrylic plate 50F may be the doubly supported beam or the peripheral end fixed beam.

One or more supporting protrusions 57F (for example, three protrusions) are provided on the first surface A1 facing the VCSEL 20 of the acrylic plate 50F. The supporting protrusion 57F supports the electrostatic capacitance sensor 59.

In the electrostatic capacitance sensor 59, two conductors (not illustrated) are disposed in parallel with the acrylic plate 50F, and these conductors are electrically connected to each other. The electrostatic capacitance sensor 59 measures a distance between the two conductors by measuring the electrostatic capacitance between the two conductors. When the acrylic plate 50F is pressed down by the finger FG through the protrusion 60F, a position of one conductor is displaced through the supporting protrusion 7F, and the distance between the two conductors changes. In this case, the electrostatic capacitance sensor 59 detects that when the electrostatic capacitance between the two conductors becomes large, the distance between the two conductors becomes short. A change in the distance corresponds to a displacement amount of the acrylic plate 50F, that is, the deflection amount y of the acrylic plate 50F. That is, when the protrusion 60F is pressed down by the finger FG, the electrostatic capacitance sensor 59 detects the deflection amount of the acrylic plate 50F. The contact pressure against the protrusion 60F and the inclination of the acrylic plate 50F can be detected based upon the deflection amount of the acrylic plate 50F.

Further, an opening part 59a is provided at a center part of the electrostatic capacitance sensor 59, that is, a region through which the emitted light L1 and the scattered light L2 pass in the electrostatic capacitance sensor 59. The electrostatic capacitance sensor 59 includes the opening part 59a, thereby not only avoiding interruption of passage of the emitted light L1 and the scattered light L2, but also preventing deterioration of the measurement accuracy of the blood flow volume using the scattered light L2.

Accordingly, the blood flow volume measuring device provided with the blood flow volume sensor 200F of the embodiment is provided with the electrostatic capacitance sensor 59 for detecting the deflection amount y of the acrylic plate 50F. Even though the electrostatic capacitance sensor 59 does not have translucency, the electrostatic capacitance sensor 59 includes the opening part 59a at the center part, such that the emitted light L1 and the scattered light L2 can pass through the vicinity of the center part of the electrostatic capacitance sensor 59. Therefore, the progress of light between the VCSEL 20, the finger FG, and the first photodiode 30 is not impeded, and the blood flow volume measurement can be stably performed. Further, the blood flow volume sensor 200F is provided with the protrusion 60F, thereby not only easily keeping the contact pressure per unit area constant, but also preventing the variation of the measured value of the blood flow volume measurement, whereby the reproducibility of the blood flow volume measurement can be improved.

Eighth Embodiment

In the first embodiment, the reproducibility of the measurement result of the blood flow volume using the rat tail is described, whereas in the embodiment, the reproducibility of the measurement result of the blood flow volume using the finger FG of the person will be described.

A blood flow volume sensor 200G of the eighth embodiment may be either one of the blood flow volume sensors 200G, 200A, 200B, 200D to 200F of the first to seventh embodiments.

Figure 32A:
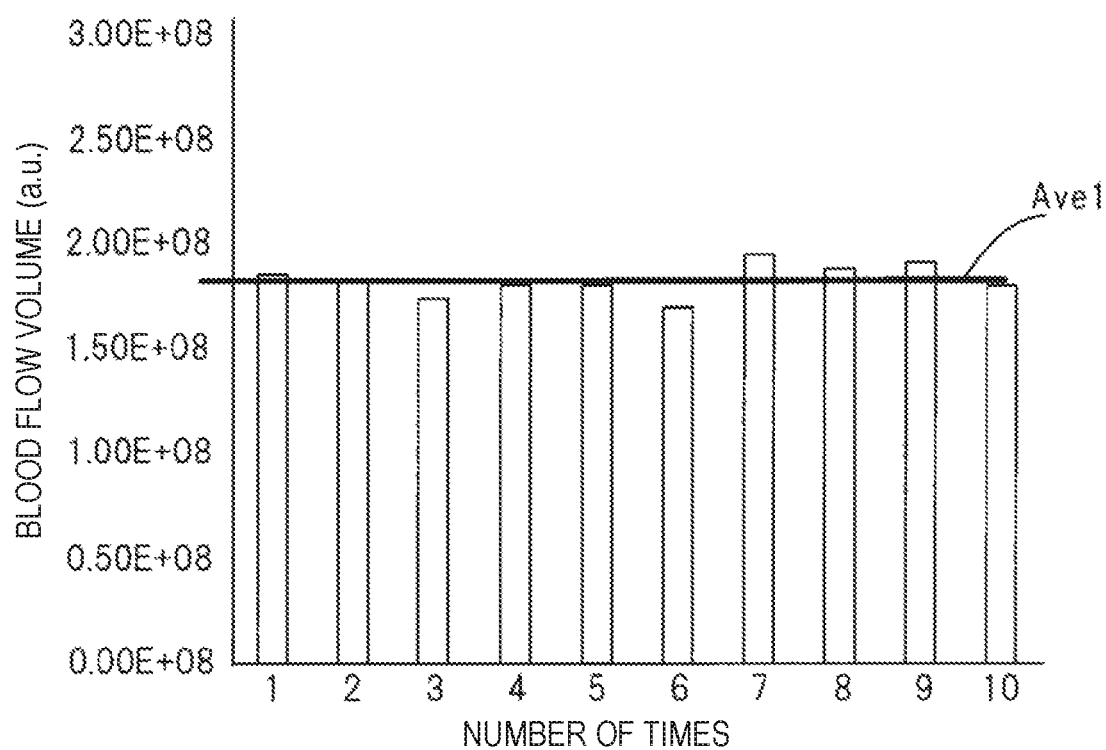
FIGS. 32A and 32B are schematic diagrams illustrating reproducibility of a blood flow volume measurement depending on presence of a protrusion.
Figure 32B:
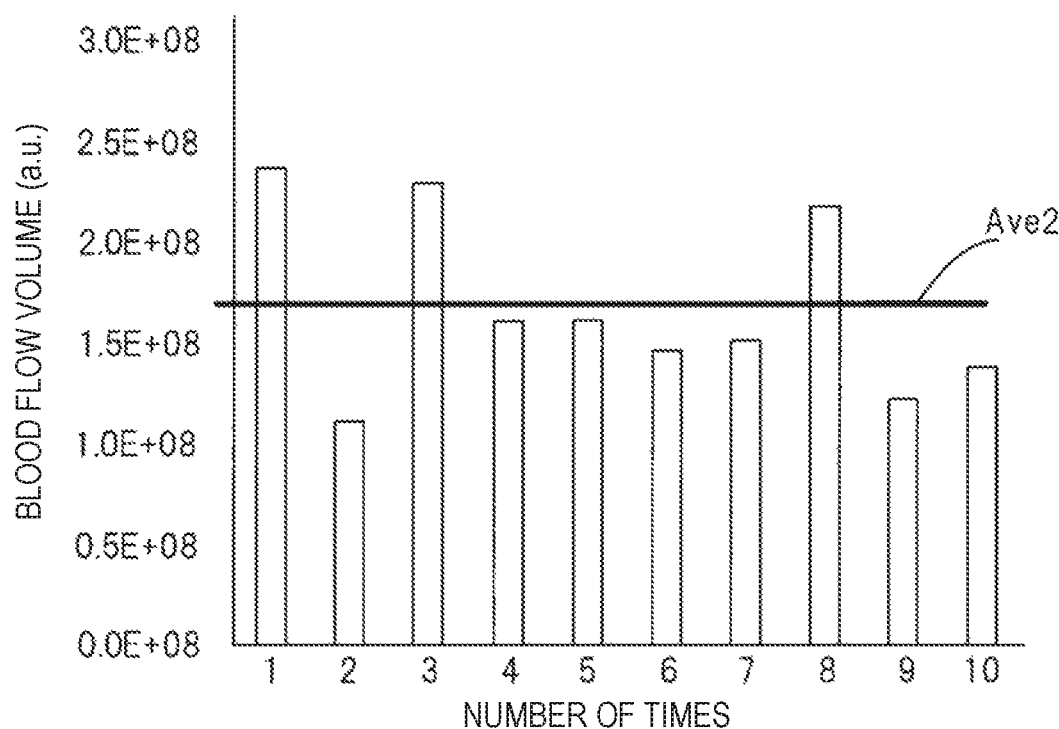

FIGS. 32A and 32B are schematic diagrams illustrating the reproducibility of the blood flow volume measurement according to the presence of the protrusion. FIG. 32A illustrates the measurement result of the blood flow volume using the finger FG of the person by the blood flow volume sensor 200G provided with the protrusion 60. FIG. 32B illustrates the measurement result of the blood flow volume using the finger FG of the person by the blood flow volume sensor not provided with the protrusion. Further, the configuration of the blood flow volume sensor not provided with the protrusion is the same as the configuration of the blood flow volume sensor 200G except for the protrusion. In FIGS. 32A and 32B, a horizontal axis of each graph indicates the number of trials of the blood flow volume measurement. Further, in FIGS. 32A and 32B, "E" of the blood flow volume in the vertical axis indicates an index of 10. For example, "3.00E+08" indicates "$3.00 \times 10^8$".

In the blood flow volume measurement using the finger FG of the person, as one example, a diameter of the protrusion 60 is defined as 4.5 mm, and a height of the protrusion 60 (a length in a thickness direction) is defined as 2 mm. In addition, a measuring portion of the blood flow volume is defined as the finger FG of the person, but a person's calf may be used.

Since the blood flow volume is influenced by the contact pressure, firstly, the blood flow volume is measured ten times with the contact pressure of 0.37 N by the blood flow volume sensor 200G provided with the protrusion 60. Results of the measurements of ten times are illustrated in FIG. 32A. After that, the contact pressure capable of obtaining almost the same blood flow volume as the measurement result of the blood flow volume sensor 200G provided with the protrusion 60 is derived by the blood flow volume sensor not provided with the protrusion, and the measurement is performed ten times with the contact pressure. The measurement results of ten times are illustrated in FIG. 32B.

Referring to FIG. 32A, it can be seen that an average value Ave1 of the measured values of the blood flow volume of ten times is approximately $1.80 \times 10^8$, and each measured value is within a range of approximately 1.70 to $2.00 \times 10^8$. Referring to FIG. 32B, it can be seen that an average value Ave2 of the measured values of the blood flow volume of ten times is approximately $1.60 \times 10^8$, and that each measured value is within a range of approximately 1.10 to $2.40 \times 10^8$. In other words, in the case where the protrusion is provided, it can be understood that the variation in the measured value of the blood flow volume is smaller in comparison with the case where the protrusion is not provided.

Accordingly, the blood flow volume measuring device provided with the blood flow volume sensor 200G of the embodiment is provided with the protrusion 60, such that the protrusion 60 serves as a guide of the contact place, thereby easily keeping the contact area of the finger FG of the person with the blood flow volume measuring device 100 constant. Therefore, the blood flow volume measuring device 100 makes it easy to keep the contact pressure per unit area constant, whereby it is possible not only to prevent the variation in the measured value of the blood flow volume measurement, but also to improve the reproducibility of the blood flow volume measurement.

Next, experimental results of the measurement of the blood flow volume of the measuring-target region (for example, the finger FG) in respective states of before exercise, during exercise, and after exercise of a person will be considered.

The purpose of this consideration is to compare changes of the measurement results of the blood flow volume measured by the blood flow volume sensor (for example, the blood flow volume sensor 200 of the first embodiment) of either one of the first to eighth embodiments according to heart rate and blood pressure rise in the respective states of before exercise, during exercise, and after exercise of the person.

Experiment in measuring the blood flow volume was conducted under the following conditions:
Experimental Location:
An indoor place in which a room temperature was kept constant by air conditioning (for example, a laboratory in which an aero bike (registered trademark) operated by a subject is installed)
Experimental Method:
(1) A cuff (not illustrated) of a sphygmomanometer was wrapped around the left upper arm of a subject (for example, a male in his twenties).
(2) The right index finger (for example, the finger FG) of the same subject was chosen as the measuring-target region, after which the blood flow volume was measured (measured at the same height as that of the heart), for example, by using the blood flow volume sensor 200 of the first embodiment, and a finger thermometer (not illustrated) was attached to the middle finger (for example, the finger FG) of the subject.
(3) The blood flow volume and finger temperature of the subject were respectively measured for the right hand as the object, and the room temperature and humidity of the experimental place were also recorded.
(4) Blood pressure of the same subject was measured for the left upper arm as the object.
The timing of performing the measurement is as follows:
(before exercise) calm state
(during exercise) 5 minutes after starting the exercise
(after exercise) 2 minutes after the end of the exercise
Exercise intensity is as follows.
The subject, for example, rides the aero bike (registered trademark), and rotates the aero bike at a moderate degree (that is, to the extent that the heart rate becomes 110 to 120 bpm) so that a rotation speed of a pedal becomes constant.

Figure 33:
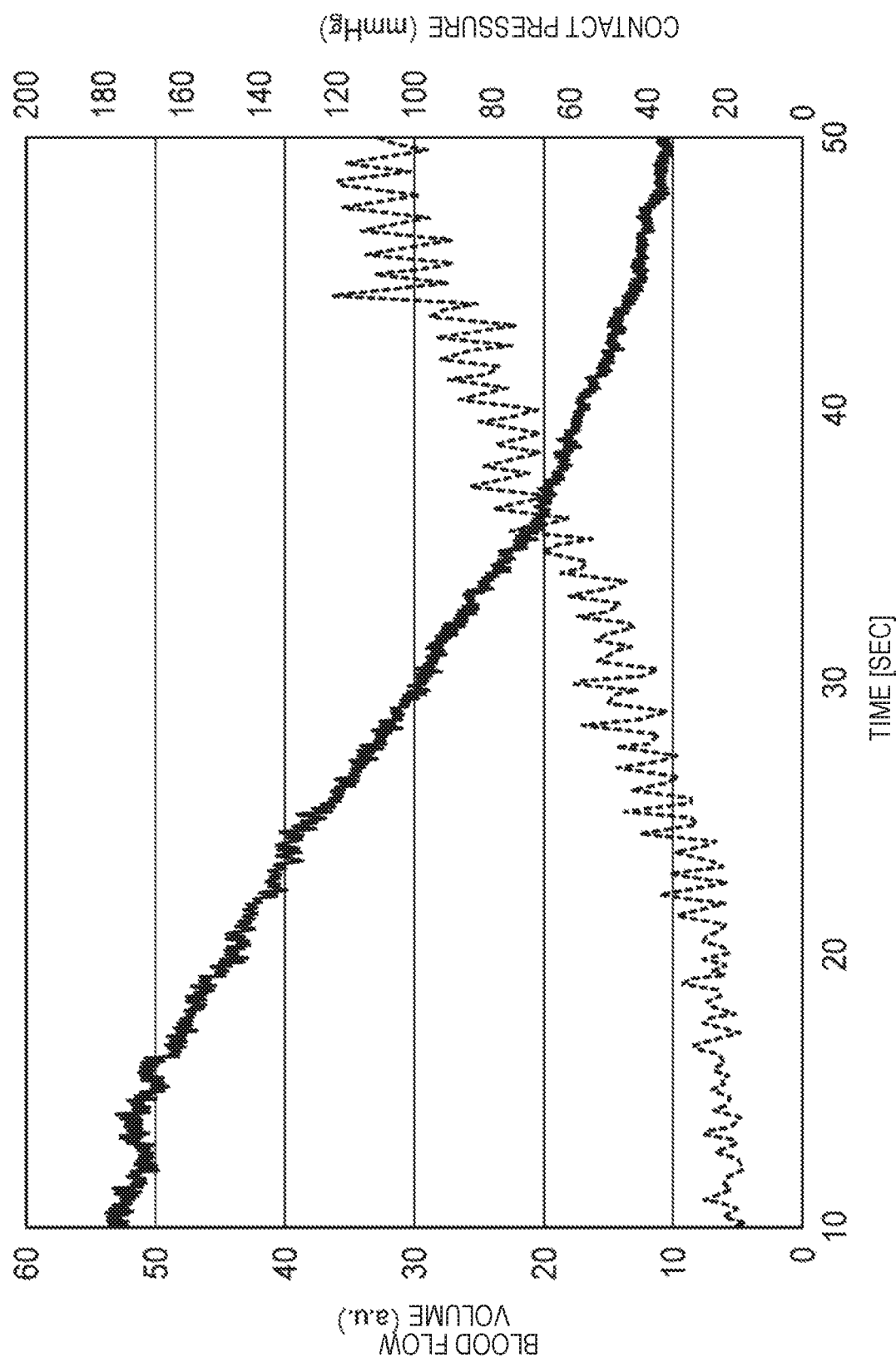
FIG. 33 is a graph illustrating a temporal change example of a blood flow volume in a finger of a subject when contact pressure against a protrusion of a blood flow volume sensor is gradually lowered before exercise (that is, calm state).
Figure 34:
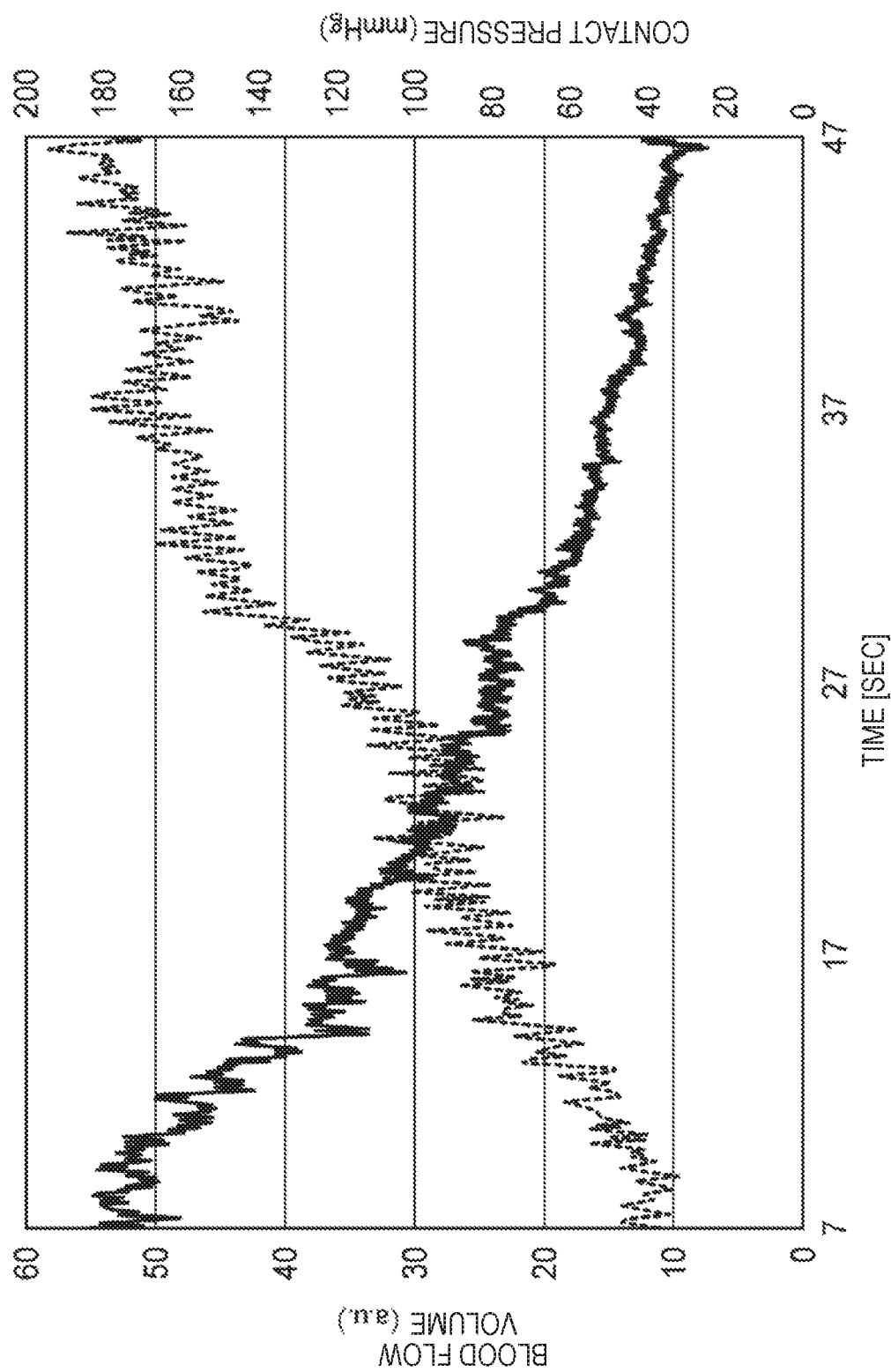
FIG. 34 is a graph illustrating a temporal change example of a blood flow volume in the finger of the subject when contact pressure against the protrusion of the blood flow volume sensor is gradually lowered during exercise.
Figure 35:
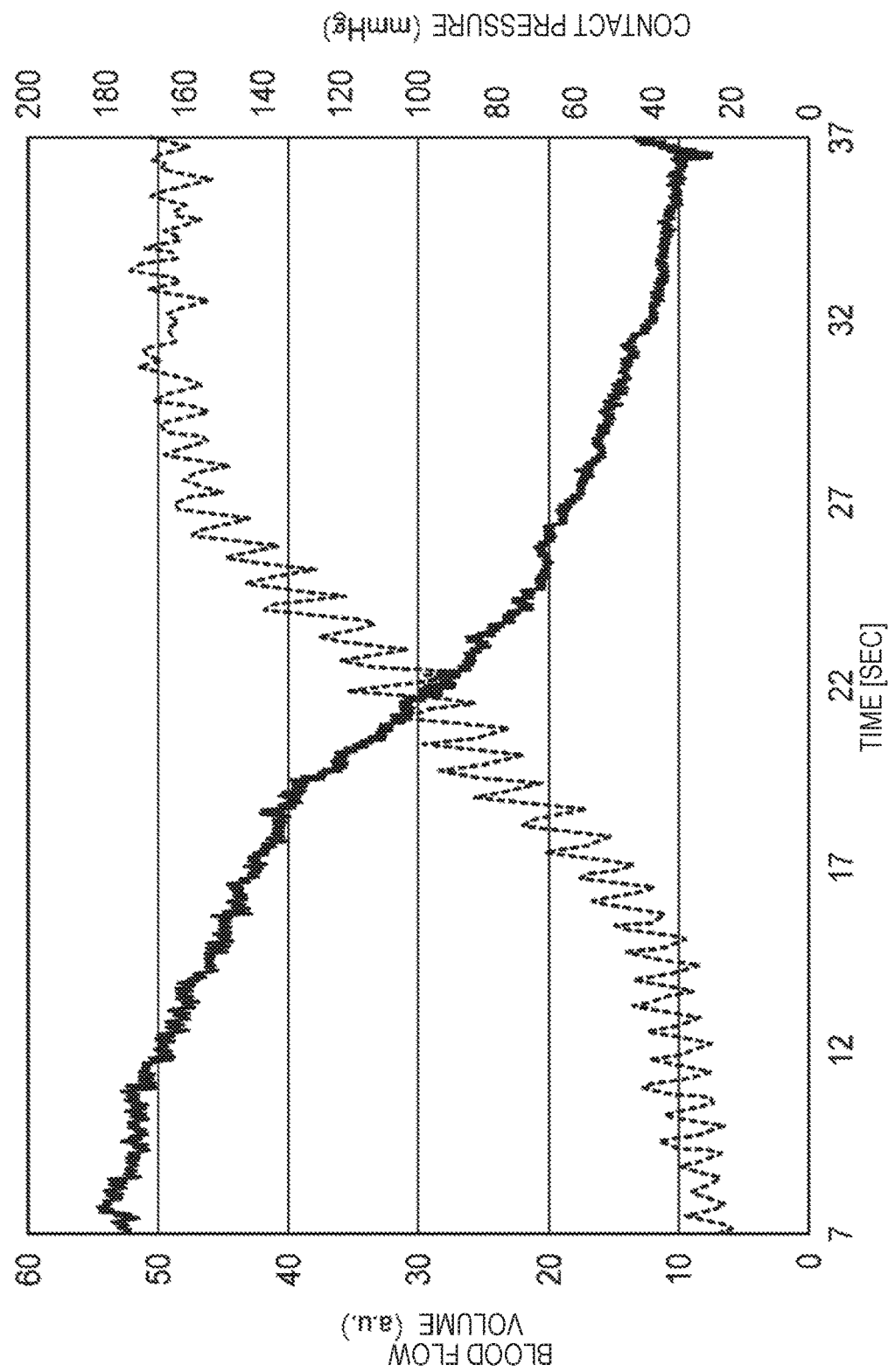
FIG. 35 is a graph illustrating a temporal change example of a blood flow volume in the finger of the subject when contact pressure against the protrusion of the blood flow volume sensor is gradually lowered after exercise.

FIG. 33 is a graph illustrating a temporal change example of the blood flow volume in the finger of the subject when the contact pressure against the protrusion 60 of the blood flow volume sensor 200 is gradually lowered before exercise (that is, calm state). FIG. 34 is a graph illustrating a temporal change example of the blood flow volume in the finger of the subject when the contact pressure against the protrusion 60 of the blood flow volume sensor 200 is gradually lowered during the exercise. FIG. 35 is a graph illustrating a temporal change example of the blood flow volume in the finger of the subject when the contact pressure against the protrusion 60 of the blood flow volume sensor 200 is gradually lowered after exercise.

As illustrated in FIG. 33, for example, a contact pressure sensor (not illustrated) provided in a frame (not illustrated) supporting the blood flow volume sensor 200 including the protrusion 60 on which the finger FG of the subject is placed is moved vertically upward and downward orthogonal to a floor surface (that is, a plane horizontal to the ground) of the experimental place by driving of an actuator (for example, not illustrated in FIG. 7) based upon the control of the processor 310. Accordingly, the contact pressure when the finger FG of the subject contacts with the protrusion 60 can be arbitrarily changed. In addition, the method of changing the contact pressure when the finger FG of the subject contacts with the protrusion 60 is not limited to the method described above.

Firstly, before exercise (that is, calm state), the measurement of the blood flow volume was performed with the finger FG of the subject as the measuring-target region by using the above-mentioned method of changing the contact pressure.

Data are obtained as measurement results as follows:
Maximum blood pressure: 132 mmHg
Minimum blood pressure: 75 mmHg
Heart rate: 79 bpm
Average blood pressure: 94 mmHg
Pulse: 57 mmHg
Fingertip temperature: 35.5° C.
Room temperature: 2° C.
Humidity: 53%
Results As illustrated in FIG. 33, the blood flow volume gradually increased as the contact pressure gradually decreased. With respect to the blood flow volume ranging from 10 seconds to 50 seconds after the measurement starts, the maximum value of blood flow volume was 36.36 (unit is omitted. The same applies hereinafter) and the minimum blood flow volume was 4.56, such that a difference therebetween became 31.80. An increase rate of the blood flow volume (in other words, an inclination representing a temporal change rate of the blood flow volume illustrated in FIG. 33) became 0.795.

Next, during the exercise, the measurement of the blood flow volume was performed with the finger FG of the subject as the measuring-target region. As illustrated in FIG. 34, in the same manner as the case of before exercise (that is, calm state), the blood flow volume gradually increased as the contact pressure gradually decreased.

Data are obtained as measurement results as follows:
Maximum blood pressure: 160 mmHg
Minimum blood pressure: 93 mmHg
Heart rate: 119 bpm
Average blood pressure: 115 mmHg
Pulse: 67 mmHg
Fingertip temperature: 36.2° C.
Room temperature: 20.9° C.
Humidity: 53%
Results According to effects of the exercise (for example, good blood circulation based upon a heavy exercise), the respective measured values relatively increased in comparison with those before exercise (that is, calm state). With respect to the blood flow volume ranging from 7 seconds to 45 seconds after the measurement starts, the maximum value of blood flow volume was 58.22 and the minimum blood flow volume was 9.86, such that a difference therebetween became 48.36. An increase rate of the blood flow volume (in other words, an inclination representing a temporal change rate of the blood flow volume illustrated in FIG. 34) became 1.209, which was increased in comparison with the case of before exercise (that is, calm state).

Finally, after exercise, the measurement of the blood flow volume was performed with the finger FG of the subject as the measuring-target region. As illustrated in FIG. 35, in the same manner as the cases of before exercise (that is, calm state) and during the exercise, as the contact pressure gradually decreased, on the contrary, the blood flow volume gradually increased.

Data are obtained as measurement results as follows:
Maximum blood pressure: 160 mmHg
Minimum blood pressure: 93 mmHg
Heart rate: 119 bpm
Average blood pressure: 115 mmHg
Pulse: 67 mmHg
Fingertip temperature: 36.2° C.
Room temperature: 20.9° C.
Humidity: 53%
Results Since the measurement was performed after exercise, some measured values decreased from the case of during the exercise. However, according to effects of the exercise (for example, good blood circulation based upon a heavy exercise), the increase rate of the blood flow volume (in other words, an inclination representing a temporal change rate of the blood flow volume illustrated in FIG. 35) increased in comparison with the cases of before exercise (that is, calm state) and during the exercise. With respect to the blood flow volume ranging from 7 seconds to 37 seconds after the measurement starts, the maximum value of blood flow volume was 52.00 and the minimum blood flow volume was 6.02, such that a difference therebetween became 45.98. An increase rate of the blood flow volume (in other words, the inclination representing the temporal change rate of the blood flow volume illustrated in FIG. 35) became 1.533, which was increased in comparison with the cases of before exercise (that is, calm state) and during the exercise.

Further, in this experiment, in addition to the subject described above, a total of three subjects including two subjects as the experiment subject in the same manner were also observed to determine whether there exist any differences between the subjects. The blood flow volume sensor of the present disclosure (for example, the blood flow volume sensor 200 of the first embodiment) can compute the blood flow volume per one heartbeat (that is, one stroke volume) by using the blood flow volume as the measured value. Here, in order to simplify the description, the blood flow volume sensor 200 of the first embodiment will be described as an example. Alternatively, even though a blood flow volume sensor of another embodiment is used, it goes without saying that one stroke volume can be measured in the same manner.

Specifically, based upon the temporal changes of the blood flow volume illustrated in FIGS. 33 to 35, the processor 310 as one example of a flow volume measurement part firstly computes a value (that is, refer to Equation 14), in which 60 is divided by time (t2−t1) required for one heartbeat (that is, corresponds to one cycle of the blood flow volume which repeats a cyclical fluctuation), as the heart rate bpm. Time t1 indicates the start time of one cycle of the blood flow volume of one heartbeat, and time t2 indicates the end time of one cycle of the blood flow volume of one heartbeat, respectively. Further, when the contact pressure applied to the finger FG is, for example, 80 mmHg, the processor 310 performs computation according to Equation 14.

Equation 14

$$\text{bpm} = \frac{60}{t2-t1}.$$ (Equation

Further, based upon the temporal changes of the blood flow volume illustrated in FIGS. 33 to 35, the processor 310 as one example of the flow volume measurement part computes one stroke volume S according to an average value (refer to Equation 15) of integrated values of the blood flow volume at time (t4−t1) required for a preset number of times (for example, 3 heartbeats). The time t4 indicates the end time of three cycles of the blood flow volume of three heartbeats with the time t1 as the start time. Further, the processor 310 performs computation according to Equation 15 when the contact pressure applied to the finger FG is, for example, 80 mmHg. In Equation 15, B indicates the blood flow volume at time t1 to t4 measured when the contact pressure applied to the finger FG is, for example, 80 mmHg.

Equation 15

$$S = \frac{\int_{t1}^{t4} B(= \text{Blood flow}) dt}{3}.$$

(Equation

Further, the processor 310 as one example of the flow volume measurement part computes a cardiac output SA according to Equation 16 by using the temporal changes of the blood flow volume illustrated in FIGS. 33 to 35 and computation results of Equations 14 and 15. Further, when the contact pressure applied to the finger FG is, for example, 80 mmHg, the processor 310 performs computation according to Equation 16.

Equation 16

$$SA = \frac{S}{1000} \times \text{bpm}$$

(Equation

Figure 36A:
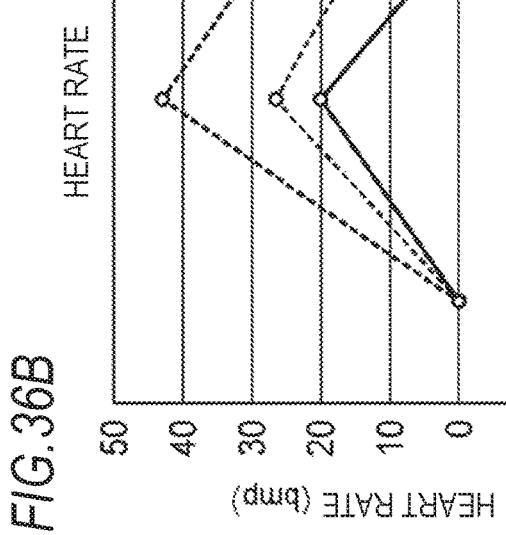
FIG. 36A is a graph illustrating respective examples of changes in average blood pressure of three subjects before exercise, during exercise, and after exercise.
Figure 36B:
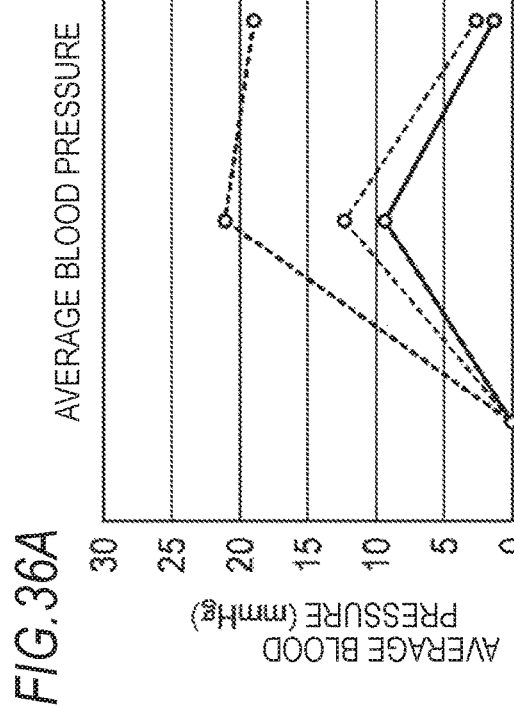
FIG. 36B is a graph illustrating respective examples of changes in heart rates of the three subjects before exercise, during exercise, and after exercise.
Figure 36C:
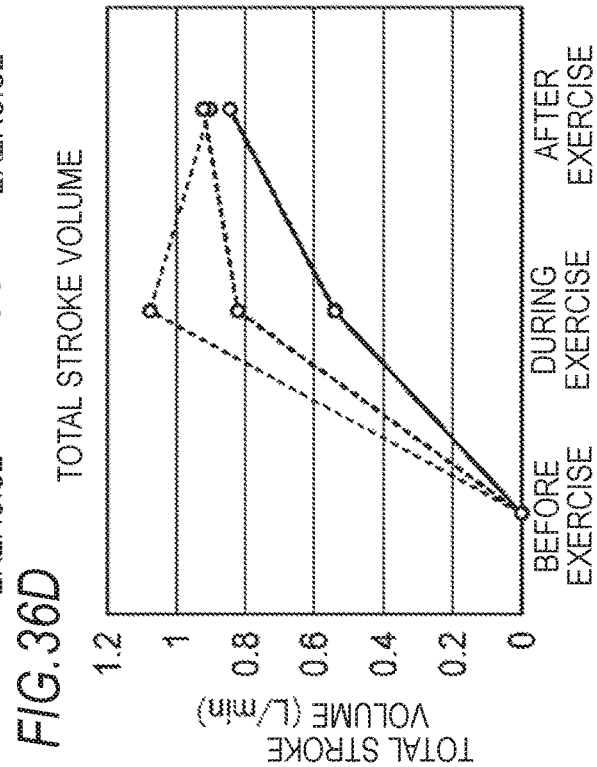
FIG. 36C is a graph illustrating respective examples of changes in a blood flow volume per one heartbeat of the three subjects before exercise, during exercise, and after exercise.
Figure 36D:
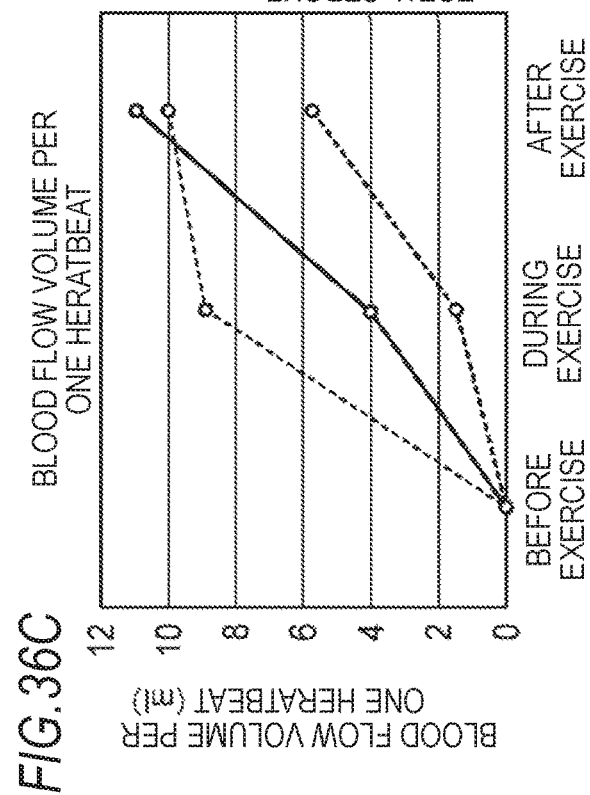
FIG. 36D is a graph illustrating respective examples of changes in total stroke volume of the three subjects before exercise, during exercise, and after exercise.

FIG. 36A is a graph illustrating respective examples of changes in average blood pressure of the three subjects before exercise, during the exercise, and after exercise. FIG. 36B is a graph illustrating respective examples of changes in the heart rates of the three subjects before exercise, during the exercise, and after the exercise. FIG. 36C is graph illustrating respective examples of changes in the blood flow volume per one heartbeat of the three subjects before exercise, during the exercise, and after exercise. FIG. 36D is a graph illustrating respective examples of changes in total stroke volume of the three subjects before exercise, during exercise, and after exercise.

In FIGS. 36A to 36D, a horizontal axis indicates the states of before exercise (that is, calm state), during exercise, and after exercise of the three subjects; a vertical axis respectively indicates the average blood pressure [mmHg], the heart rate [bpm], the blood flow volume [ml] per one heartbeat, and the total stroke volume [L/min]; and the states of before exercise of the three subjects are respectively prepared to be a reference value (for example, zero).

In FIGS. 36A and 36B, the average blood pressure and the heart rate of the three subjects are the lowest before exercise (that is, calm state), are the highest during exercise, and are lowered to the same degrees as those of before exercise (that is, calm state). In other words, it means that both the average blood pressure and the heart rate increase by exercise.

Meanwhile, as illustrated in FIG. 36C, the blood flow volume per one heartbeat of the three subjects (refer to Equation 15) is the lowest before exercise (that is, calm state), and as the time passes during exercise and after exercise, the blood flow volume per one heartbeat thereof gradually increases. It's assumed that in each of the three subjects, the blood flow volume per one heartbeat is increased by the exercise, and a flow of blood (that is, blood circulation) for allowing cells in the body to function normally is improved.

In FIG. 36D, the total stroke volume of the three subjects is the lowest before exercise (that is, calm state), is the highest during exercise, and is slightly lower than that of during exercise in the case of after exercise.

As described above, according to the blood flow volume sensor of the present disclosure (for example, the blood flow volume sensor 200 of the first embodiment), based upon the temporal change of the blood flow volume, when the contact pressure applied to the finger FG is a preset value (for example, 80 mmHg), it is possible to compute one stroke volume (that is, the blood flow volume per one heartbeat) by the average value (refer to Equation 15) of the integrated value of the blood flow volume, for example, at the time (t4−t1) required for three heartbeats. Accordingly, the blood flow volume sensor 200 can easily compute one stroke volume (that is, the blood flow volume per one heartbeat) as one example of an index for promoting health with high accuracy.

As described above, the embodiments are described with reference to the drawings, and it goes without saying that the present disclosure is not limited to such examples. It is apparent that those skilled in the art can come up with various kinds of modifications or corrections within the scope described in the scope of the patent claims, and it is understood that the modifications or the corrections also naturally belongs to the technical scope of the present disclosure.

In the embodiments, the acrylic plate or the glass plate is exemplified, but may be an acrylic film or a glass film may be used. Further, another plate-shaped member or film having translucency with respect to the emitted light L1 and the scattered light L2 may be used.

In the embodiments, the measuring-target region may be a finger FG or the tail of a living body (for example, a person, a cow, or a rat), or may be other portions (for example, a forehead, a wrist, an ankle, or another portion). Further, in the fourth embodiment, the measuring-target region is not limited to the tube 90, and may be a portion of another measuring object.

In the embodiments, the warning information is exemplified by being displayed on the display 330. Alternatively, the warning information may be outputted in another output mode. For example, the warning information may not be character information, and, for example, an LED (Light Emitting Diode) may be lit or blink with a color indicating the warning. Further, the warning information may be outputted with voice by a speaker (not illustrated), or may be vibrated with a vibration pattern indicating the warning information by a vibrator (not illustrated).

In the embodiments, one protrusion is provided as an example. Alternatively, a plurality of protrusions may be provided.

Overview of One Embodiment of Present Disclosure

A flow volume measuring device according to one embodiment of the present disclosure includes a light source which emits light to a measuring-target region; a light receiving element which receives light scattered at the measuring-target region from the light emitted from the light source; a contact member having translucency with respect to a wavelength of the emitted light and a wavelength of the scattered light, and including a surface which faces the measuring-target region and with which the measuring-target region is contactable over the entire surface; and a flow volume measuring unit which measures a flow volume of liquid flowing through the measuring-target region based upon the scattered light.

According to the configuration, the flow volume measuring device can keep a contact area of the measuring-target region with respect to the flow volume measuring device constant. Accordingly, the flow volume measuring device makes it easy to keep contact pressure per unit area constant, and can prevent a variation in a measured value of flow volume measurement, thereby improving reproducibility of the flow volume measurement.

The flow volume measuring device according to one embodiment of the present disclosure includes a translucent member which covers at least a part of the light source and the light receiving element and has translucency with respect to the wavelength of the emitted light and the wavelength of the scattered light, and the contact member is a protrusion disposed on a surface of the translucent member which faces the measuring-target region.

According to the configuration, even though a surface of the translucent member including a component relating to flow volume measurement is larger than the measuring-target region, that is, the flow volume measuring derive is larger than the measuring-target region, it is possible to keep the contact area of the measuring-target region with respect to the flow volume measuring device constant.

In the flow volume measuring device according to one embodiment of the present disclosure, the translucent member is formed such that a thickness thereof at first position facing the protrusion is thicker than the thickness at a second position not facing the protrusion in an extending direction of the translucent member.

According to the configuration, in the flow volume measuring device, the translucent member receiving the contact pressure from the measuring-target region through the protrusion is hardly deflected, thereby preventing deterioration of measurement accuracy of the flow volume measurement. Therefore, the flow volume measuring device can improve the reproducibility of the flow volume measurement.

The flow volume measuring device according to one embodiment of the present disclosure includes a supporting member which surrounds at least a part of the translucent member and supports part of the measuring-target region in a state where the measuring-target region contacts with the contact member. The supporting member includes an opening part facing a surface where the measuring-target region contacts with the contact member.

According to the configuration, the flow volume measuring device can prevent the measuring-target region from inadvertently contacting with the translucent member. Accordingly, in the flow volume measuring device, since the deflection amount of the translucent member is stabilized, the flow volume measuring device is not only capable of improving the measurement accuracy of the flow volume measurement based upon the deflection amount, but also capable of improving the reproducibility of the flow volume measurement.

In the flow volume measuring device according to one embodiment of the present disclosure includes a base which accommodates the light source and the light receiving element, and both ends of the translucent member are fixed to both ends of the base.

According to the configuration, even when the translucent member is operated as opposite end fixed beam, the flow volume measuring device is not only capable of improving the measurement accuracy of the flow volume measurement based upon the deflection amount, but also capable of improving the reproducibility of the flow volume measurement.

The flow volume measuring device according to one embodiment of the present disclosure includes the base that accommodates the light source and the light receiving element, and a peripheral end of the translucent member is fixed to a peripheral end of the base.

According to the configuration, even when the translucent member is operated as a peripheral end fixed beam, the flow volume measuring device is not only capable of improving the measurement accuracy of the flow volume measurement based upon the deflection amount, but also capable of improving the reproducibility of the flow volume measurement.

In the flow volume measuring device according to one embodiment of the present disclosure, the flow volume measuring unit measures contact pressure against the contact member and the flow volume of the liquid flowing through the measuring-target region based upon the scattered light.

According to the configuration, for example, the flow volume measuring device intentionally can change the contact pressure against the contact member to measure the blood flow volume while searching the contact pressure suitable for measuring the blood flow volume, thereby improving the measurement accuracy of the blood flow volume.

In the flow volume measuring device according to one embodiment of the present disclosure, when the contact pressure against the contact member is a preset contact pressure, the flow volume measuring unit measures the flow volume of the liquid flowing through the measuring-target region based upon the scattered light.

According to the configuration, the flow volume measuring device measures the flow volume of the liquid at a preset contact pressure at which a relatively large pulse wave amplitude can be measured, thereby making it possible to stably perform the blood flow volume measurement and to obtain the measured value of the blood flow volume with the high reproducibility.

The flow volume measuring device according to one embodiment of the present disclosure includes an output unit which outputs warning information when an inclination in a reference direction of the contact member is equal to or greater than a preset value.

According to the configuration, the pressure of the contact member by the measuring-target region can be provided to a user so that the pressure thereof becomes equal to the contact surface of the contact member, thereby making it possible to urge the user to set an equally distributed load.

In the flow volume measuring device according to one embodiment of the present disclosure, the flow volume of the liquid is a blood flow volume.

According to the configuration, the flow volume measuring device can prevent a variation in the measured value of the blood flow volume measurement and can improve the reproducibility of the blood flow volume measurement.

In the flow volume measuring device according to one embodiment of the present disclosure, the flow volume of the liquid is a flow volume of liquid flowing through a tubular member.

According to the configuration, for example, it is possible to prevent the variation in the measured value of the flow volume measurement of a drip-infusion fluid flowing through the tube at the time of drip infusion, thereby improving the reproducibility of the flow volume measurement of the drip-infusion fluid.

The flow volume measuring device according to one embodiment of the present disclosure further includes a dehydrated state identification unit that identifies a dehydrated state in the measuring-target region based upon the measured flow volume of the liquid flowing through the measuring-target region by the flow volume measuring unit.

According to the configuration, since the flow volume measuring device has high reliability of the blood flow volume measured based upon the stability of the contact pressure applied to the protrusion, it is possible to estimate the presence of the dehydrated state at the measuring-target region depending on the amount of the blood flow volume with high accuracy.

The flow volume measuring device according to one embodiment of the present disclosure computes one stroke volume indicating a blood flow volume per one heartbeat based upon a flow volume corresponding to a preset number of cycles of the liquid flowing through the measured measuring-target region.

According to the configuration, since the flow volume measuring device has high reliability of the blood flow volume measured based upon the stability of the contact pressure applied to the protrusion, it is possible to easily compute one stroke volume (that is, the blood flow volume per one heartbeat) as one example of an index for promoting health with high accuracy.

A flow volume measuring device according to one embodiment of the present disclosure includes a light source which emits light to a measuring-target region; a light receiving element which receives light scattered at the measuring-target region from the light emitted from the light source; a translucent member having translucency with respect to a wavelength of the emitted light and a wavelength of the scattered light; a pressure sensor embedded in the translucent member, including a surface which faces the measuring-target region and with which the measuring-target region is contactable over the entire surface, and detecting contact pressure caused by contact with the measuring-target region; and a flow volume measuring unit which measures a flow volume of liquid flowing through the measuring-target region based upon the scattered light.

According to the configuration, the flow volume measuring device can keep the contact area of the measuring-target region with respect to the pressure sensor embedded in the translucent member constant. Thus, the flow volume measuring device makes it easy to keep the contact pressure per unit area detected by the pressure sensor constant, whereby it is possible not only to prevent the variation in the measured value of the flow volume measurement, but also to improve the reproducibility of flow volume measurement.

A pressure measuring device according to one embodiment of the present disclosure includes a light source which emits light to a measuring-target region; a light receiving element which receives light scattered at the measuring-target region from the light emitted from the light source; a contact member having translucency with respect to a wavelength of the emitted light and a wavelength of the scattered light, and including a surface which faces the measuring-target region and with which the measuring-target region is contactable over the entire surface; a flow volume measuring unit which measures a flow volume of liquid flowing through the measuring-target region based upon the scattered light; and a pressure measuring unit which measures pressure of the liquid flowing through the measuring-target region based upon pulse wave amplitude of the flow volume of the measuring-target region.

According to the configuration, the pressure measuring device can keep the contact area of the measuring-target region with respect to the pressure measuring device constant. Accordingly, the pressure measuring device makes it easy to keep the contact pressure per unit area constant, whereby it is possible not only to prevent the variation in the measured value of the flow volume measurement, but also to improve the reproducibility of the flow volume measurement. Therefore, the pressure measuring device is not only capable of preventing the variation of the measured value of the pressure measurement derived based upon the measured value of the flow volume measurement, but also capable of improving the reproducibility of the pressure measurement.

A flow volume measuring method according to one embodiment of the present disclosure is a flow volume measuring method in the flow volume measuring device, the method including: emitting light to a measuring-target region; receiving light scattered at the measuring-target region from the emitted light; and measuring a flow volume of liquid flowing through the measuring-target region based upon the scattered light, wherein a contact member has translucency with respect to a wavelength of the emitted light and a wavelength of the scattered light, and includes a surface which faces the measuring-target region and with which the measuring-target region is contactable over the entire surface.

According to the method, the flow volume measuring device can keep a contact area of the measuring-target region with respect to the flow volume measuring device constant. Accordingly, the flow volume measuring device makes it easy to keep contact pressure per unit area constant, and can prevent the variation in the measured value of the flow volume measurement, thereby improving the reproducibility of the flow volume measurement.

A pressure measuring method according to one embodiment of the present disclosure is a pressure measuring method in a pressure measuring device, the method including: emitting light to a measuring-target region; receiving light scattered at the measuring-target region from the emitted light; measuring a flow volume of liquid flowing through the measuring-target region based upon the scattered light; and measuring pressure of the liquid flowing through the measuring-target region based upon pulse wave amplitude of the flow volume of the measuring-target region, wherein a contact member has translucency to a wavelength of the emitted light and a wavelength of the scattered light, and includes a surface which faces the measuring-target region and with which the measuring-target region is contactable over the entire surface.

According to the configuration, the pressure measuring device can keep the contact area of the measuring-target region with respect to the pressure measuring device constant. Accordingly, the pressure measuring device makes it easy to keep the contact pressure per unit area constant, whereby it is possible not only to prevent the variation in the measured value of the flow volume measurement, but also to improve the reproducibility of the flow volume measurement. Therefore, the pressure measuring device is not only capable of preventing the variation of the measured value of the pressure measurement derived based upon the measured value of the flow volume measurement, but also capable of improving the reproducibility of the pressure measurement.

Further, this application is based upon Japanese Patent Application No. 2016-109557, filed on May 31, 2016, the entire contents of which are incorporated herein by reference.

INDUSTRIAL APPLICABILITY

The present disclosure is useful for a flow volume measuring device, a flow volume measuring method, a pressure measuring device, a pressure measuring method, and the like, all of which are not only capable of improving measurement accuracy of a liquid flow volume, but also capable of improving reproducibility of a measured value.

The invention claimed is:

1. A flow volume measuring device comprising:
   a light source configured to emit first light to a measuring-target region;
   a light receiving element configured to receive second light, the second light being generated by scattering the first light from the light source at the measuring-target region;
   a base which accommodates the light source and the light receiving element therein, the base having a ledge at a periphery thereof;
   a deflection plate configured to be deflected by a pressure that is applied to the deflection plate, a periphery of the deflection plate being fixed at the ledge of the base;
   a contact member disposed at an interior area of the deflection plate in a plan view, the contact member having translucency with respect to a wavelength of the first light and a wavelength of the second light, the contact member including a surface which faces the measuring-target region, an entirety of the surface of the contact member contacting the measuring-target region when the measuring-target region abuts the contact member;
   a memory configured to store a program; and
   a processor configured to execute the program so as to:
     cause the light source to emit the first fight toward the measuring-target region when the measuring-target region abuts the contact member and downwardly deflects the deflection plate;
     cause the light receiving element to receive the second light; and
     measure a flow volume of liquid flowing through the measuring-target region based on the second light.

2. The flow volume measuring device according to claim 1, wherein the contact member is a protrusion disposed on the deflection plate.

3. The flow volume measuring device according to claim 1, wherein
   the deflection plate has a first portion facing the contact member and a second portion not facing the contact member, and
   the first portion is thicker than the second portion.

4. The flow volume measuring device according to claim 1,
   wherein the base has a recess, and the recess has a bottom and an opening opposite to each other to form an inner space between the bottom and the opening, and
   the light source and the light receiving element are housed in the inner space of the base.

5. The flow volume measuring device according to claim 1, wherein
   the processor is further configured to measure a value of the pressure applied to the deflection plate when the measuring-target region abuts the contact member.

6. The flow volume measuring device according to claim 5, wherein
   the processor is configured to measure the flow volume of the liquid flowing through the measuring-target region when the measured value of the pressure is a preset pressure.

7. The flow volume measuring device according to claim 1, further comprising:
   an output unit which outputs warning information when an inclination in a reference direction of the contact member is equal to or greater than a preset value.

8. The flow volume measuring device according to claim 1, wherein
   the flow volume of the liquid is a blood flow volume.

9. The flow volume measuring device according to claim 1, wherein
   the flow volume of the liquid is a flow volume of liquid flowing through a tubular member.

10. The flow volume measuring device according to claim 1,
    wherein the processor is further configured to identify a dehydrated state in the measuring-target region based upon the measured flow volume of the liquid flowing through the measuring-target region.

11. The flow volume measuring device according to claim 1, wherein
    the processor is further configured to compute one stroke volume indicating a blood flow volume per one heartbeat based upon the measured flow volume corresponding to a preset number of cycles of the liquid flowing through the measuring-target region.

12. A flow volume measuring device comprising:
    a light source configured to emit first light to a measuring-target region;
    a light receiving element configured to receive second light, the second light being generated by scattering the first light from the light source at the measuring-target region;
    a base which accommodates the light source and the light receiving element therein, the base having a ledge at a periphery thereof;
    a deflection plate configured to be deflected by a pressure that is applied to the deflection plate, a periphery of the deflection plate being fixed at the ledge of the base, the deflection plate having translucency with respect to a wavelength of the first light and a wavelength of the second light;
    a pressure sensor, part of the pressure sensor being embedded in the deflection plate, the part of the pressure sensor including a surface which faces the measuring-target region, an entirety of the surface of the part of the pressure sensor contacting the measuring-target region when the measuring-target region abuts the part of the pressure sensor, the pressure sensor being configured to detect a contact pressure when the measuring-target region abuts the part of the pressure sensor and downwardly deflects the deflection plate;
    a memory configured to store a program; and
    a processor configured to execute the program so as to:
      cause the light source to emit the first fight toward the measuring-target region when the measuring-target region abuts the part of the pressure sensor and downwardly deflects the deflection plate;
      cause the light receiving element to receive the second light; and
      measure a flow volume of liquid flowing through the measuring-target region based on the second light.

13. A pressure measuring device comprising:
    a light source configured to emit first light to a measuring-target region;
    a light receiving element configured to receive second light, the second light being generated by scattering the first light from the light source at the measuring-target region;
    a base which accommodates the light source and the light receiving element therein, the base having a ledge at a periphery thereof;

a deflection plate configured to be deflected by a pressure that is applied to the deflection plate, a periphery of the deflection plate being fixed at the ledge of the base;

a contact member disposed at an interior area of the deflection plate in a plan view, the contact member having translucency with respect to a wavelength of the first light and a wavelength of the second light, the contact member including a surface which faces the measuring-target region, an entirety of the surface of the contact member contacting the measuring-target region when the measuring-target region abuts the contact member;

a memory configured to store a program; and a processor configured to execute the program so as to:
cause the light source to emit the first fight toward the measuring-target region when the measuring-target region abuts the contact member and downwardly deflects the deflection plate;
cause the light receiving element to receive the second light;
measure a flow volume of liquid flowing through the measuring-target region based on the second light; and
measure a pressure of the liquid flowing through the measuring-target region based upon pulse wave amplitude of the flow volume of the measuring-target region.

14. A flow volume measuring device comprising:

a light source configured to emit first vertical cavity surface emitting laser light to a measuring-target region;

a light receiving element configured to receive second light, the second light being generated by scattering the first vertical cavity surface emitting laser light from the light source at the measuring-target region;

a base which accommodates the light source and the light receiving element therein, the base having a ledge at a periphery thereof;

a deflection plate configured to be deflected by a pressure that is applied to the deflection plate, a periphery of the deflection plate being fixed at the ledge of the base;

a contact member disposed at an interior area of the deflection plate in a plan view, the contact member having translucency with respect to a wavelength of the first vertical cavity surface emitting laser light and a wavelength of the second light, the contact member including a surface which faces the measuring-target region, an entirety of the surface of the contact member contacting the measuring-target region when the measuring-target region abuts the contact member;

a memory configured to store a program; and a processor configured to execute the program so as to:
cause the light source to emit the first vertical cavity surface emitting laser light toward the measuring-target region when the measuring-target region abuts the contact member and downwardly deflects the deflection plate;
cause the light receiving element to receive the second light; and
measure a flow volume of liquid flowing through the measuring-target region based on the second light.

* * * * *